United States Patent
Wang et al.

(10) Patent No.: US 11,447,760 B2
(45) Date of Patent: Sep. 20, 2022

(54) SPECIAL ENZYME FOR GALACTOOLIGOSACCHARIDE PRODUCTION AS WELL AS PREPARATION AND APPLICATION THEREOF

(71) Applicant: Tianjin University of Science and Technology, Tianjin (CN)

(72) Inventors: Zhengxiang Wang, Tianjin (CN); Dandan Niu, Tianjin (CN); Kangming Tian, Tianjin (CN)

(73) Assignee: Tianjin University of Science and Technology, Tianjin (CN)

( * ) Notice: Subject to any disclaimer, the term of this patent is extended or adjusted under 35 U.S.C. 154(b) by 0 days.

(21) Appl. No.: 17/476,433

(22) Filed: Sep. 15, 2021

(65) Prior Publication Data
US 2022/0098563 A1     Mar. 31, 2022

Related U.S. Application Data

(63) Continuation-in-part of application No. PCT/CN2020/127693, filed on Nov. 10, 2020.

(30) Foreign Application Priority Data

Sep. 29, 2020   (CN) .......................... 202011051056.1

(51) Int. Cl.
  *C12N 9/24* (2006.01)
  *C12N 15/75* (2006.01)
  *C12P 19/04* (2006.01)

(52) U.S. Cl.
  CPC .......... *C12N 9/2402* (2013.01); *C12N 15/75* (2013.01); *C12P 19/04* (2013.01); *C12Y 302/01108* (2013.01)

(58) Field of Classification Search
  None
  See application file for complete search history.

(56) References Cited

FOREIGN PATENT DOCUMENTS

| CN | 102250856 A | 11/2011 |
|---|---|---|
| CN | 104673769 A | 6/2015 |
| CN | 104630123 B | 9/2018 |

OTHER PUBLICATIONS

Jingyuan Song, et al., Causes of Production of Multiple Forms of β-Galactosidase by Bacillus circlulans, Biosci Biotechnol. Biochem., 2011, pp. 268-278, 75(2).
Zhao Jihua, et al., Establishment and preliminary application of a rapid screening method for lactase with high galactosyl transferase activity, Food and Fermentation Industries, 2020, pp. 17-20, 46(7).
Tian Kangming, et al., Molecular cloning and biochemical characterization of lactase with high transgalactosylation activity, Food and Fermentation Industries, 2020, pp. 8-13, 46(15).
Dandan Niu, et al., Development of a pair of bifunctional expression vectors for *Escherichia coli* and Bacillus licheniformis J Ind Microbiol Biotechnol, 2007, pp. 357-362, 34.
Shi Lu, Enhanced expression of protease by Bacillus licheniformis and its application in enzymolysis procedure of soybean peptide, A Thesis Submitted for the Degree of Master, 2017.
Thomas Rygus, et al., Inducible high-level expression of heterologous genes in Bacillus megaterium using the regulatory elements of the xylose-utilization operon, Appl Microbiol Biotechnol, 1991, pp. 594-599, 35.
Zhuge Jian, et al., Manual of Industrial Microbiology Experiment Technology, China Light Industry Press, 1994.
Willem P. C. Stemmer, Rapid evolution of a protein in vitro by DNA shuffling, J. Nature, 1994, pp. 389-391, vol. 370.
B.Rajendra Krishnan, et al. Direct and crossover PCR amplification to facilitate Tn5supF-based sequencing of lambda phage clones. Nucleic Acids Research, 1991, pp. 6177-6182, vol. 19 No. 22.
Xu Min, et al., Effect of High Osmolarity on Electrotransformation Efficiency of Bacteria, Journal of Wuxi University of Light Industry, 2004, pp. 98-100, vol. 23 No.4.
Dongbo Cai, et al., High-level Expression of nattokinase in Bacillus licheniformis by manipulating signal peptide and signal peptidase, J Appl Microbiol., 2016, pp. 704-712, 121.
GB/T 33409-2016, Determination of the activity of beta-galactosidase— Spectrophotometric method, 2016, The General Administration of Quality Supervision, Inspection and Quarantine of the People's Republic of China and the National Standardization Administration of the People's Republic of China.
GB/T 23527-2009, Protease preparations, 2009, The General Administration of Quality Supervision, Inspection and Quarantine of the People's Republic of China and the National Standardization Administration of the People's Republic of China.

(Continued)

*Primary Examiner* — Suzanne M Noakes
(74) *Attorney, Agent, or Firm* — Bayramoglu Law Offices LLC

(57) ABSTRACT

A method of using lactase for generating galactooligosaccharide as well as the preparation and an application of the lactase are provided. Lactase (BglD305 derived from *Bacillus circulans* B2301 and BglD derived from *Bacillus circulans* ATCC 31382) molecules from two sources are taken as the basis for molecular evolution, so as to obtain new lactase enzyme molecules with high galactooligosaccharide synthesis efficiency and good expression performance. The high-producing strain lactase is further constructed, the lactase can be efficiently synthesized during the submerged fermentation, and the enzyme molecule is secreted into the culture medium, the high-activity enzyme preparation is directly prepared from the fermentation supernatant, and the lactase expression level can achieve 2208 U/mL. As the result, the fermentation manufacturing cost of lactase is reduced, the fermentation manufacturing process is simplified, and the quality of the lactase preparation is improved.

18 Claims, 5 Drawing Sheets
Specification includes a Sequence Listing.

(56) References Cited

OTHER PUBLICATIONS

Marion M. Bradford, A Rapid and Sensitive Method for the Quantitation of Microgram Quantities of Protein Utilizing the Principle of Protein-Dye Binding, Analytical Biochemistry, 1976, pp. 248-254, 72.

GenBank: AB605256.1, Bacillus circulans bga gene for beta galactosidase, complete cds, strain: ATCC 31382, 2011.

SPECIAL ENZYME FOR GALACTOOLIGOSACCHARIDE PRODUCTION AS WELL AS PREPARATION AND APPLICATION THEREOF

CROSS REFERENCE TO THE RELATED APPLICATIONS

This application is a continuation-in-part of International Application No. PCT/CN2020/127693, filed on Nov. 10, 2020, which is based upon and claims priority to Chinese Patent Application No. 202011051056.1, filed on Sep. 29, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBRSMJ021-Sequence Listing.txt, created on 09/14/2021 and is 164,684 bytes in size.

TECHNICAL FIELD

The invention belongs to the technical field of enzyme engineering, and specifically relates to a lactase for producing galactooligosaccharides and its preparation and application.

BACKGROUND

Oligosaccharides, also known as oligose, refers to linear or branched carbohydrates with a degree of polymerization of 2-10 connected by monosaccharide molecules through glycosidic bonds. They can be simply divided into functional oligosaccharides and ordinary oligosaccharides. Among them, functional oligosaccharides refer to the polymerization of 2-10 identical or different monosaccharides with glycosidic bonds; it has the sweet taste and sensory characteristics shared by sugars, and can directly replace sucrose as a sweet ingredient. It is not degraded by human gastric acid and gastric enzymes, not absorbed in the small intestine, and can reach the large intestine; and has physiological properties such as promoting the proliferation of probiotics in the human body. Among the functional oligosaccharides, the glycosidic bond is not easily hydrolyzed and digested by hydrolytic enzymes in the human intestines and stomach due to the anomeric carbon atom (C1 or C2) configuration of the monosaccharide, which is also called non-digestible sugar.

Naturally occurring functional oligosaccharides, such as galactooligosaccharides (GOS) present in human milk, cow milk, goat milk, etc., is an important prebiotic and plays an important role in human health. In the 1950s, there have been reports on the use of β-galactosidase to catalyze the industrialization of lactose to produce galactooligosaccharides. Internationally, GOS products were successfully marketed in 1988.

In the production of galactooligosaccharides, lactose is mainly used as the raw material, and oligosaccharides with a low degree of polymerization containing one glucose or all galactose molecules are synthesized during the hydrolysis of lactose by the transglycosylation of lactase, which can be expressed as Gal-(Gal)$_n$-Glc/Gal (n is 1-4). The lactase (a type of β-galactosidase, EC3.2.1.23) used in the production of galactooligosaccharides can generate GOS through its transgalactosylation, which is a kind of enzyme very commercial value in the dairy industry. Commercially, *Aspergillus niger* (*A. niger*), *Aspergillus oryzae* (*A. oryzae*), *Kluyveromyces lactis* (*K. lactis*), *K. fragilis* (*K. fragilis*), *Cryptococcus laurentii* (*C. laurentii*), *Bacillus circulans* and other strains are generally chosen, through the submerged fermentation method to prepare lactase products. The source of lactase and the production process of GOS are different. Although there are certain differences in the composition of enzyme activity and transglycosylation activity, the catalyzed synthesis of galactooligosaccharides is mainly composed of β-1,3, β-1,4, and β-1,6 glycosidic bonds connection, of which β-1,4 glycosidic bond is the main one. In addition, in view of the thermotolerant of enzymes, some new types of high thermotolerant lactases have been researched and developed. Lactases derived from microorganisms such as *Sulfolobus solfataricus*, *Saccharopolyspora rectivirgula*, *Pyrococcus furiosus* and *Thermotoga maritima* can be used to catalyze synthesis of GOS at temperature of 70° C.-80° C. The existing commercial lactases generally form 5%-50% galactooligosaccharides from lactose as a raw material. The lactase (such as Biolacta®) produced by *B. circulans* ATCC 31382 is the lactase with the strongest ability to synthesize GOS so far. This enzyme has four different forms in enzyme preparation products (Song J, Abe K, Imanaka H, Imamura K, Minoda M, Yamaguchi S, and Nakanishi K, *Biosci. Biotechnol. Biochem.*, 2011; 75, 268-278), among which β-Gal-C and β-Gal-D are considered the most valuable for GOS production. In addition, the lactase identified from *B. circulans* B2301 can catalyze lactose to form 54.5% GOS at a high temperature above 60° C. It is the lactase with the best GOS synthesis performance among all reported lactases (Zhao Jihua, et al., *Food and Fermentation Industries*, 2020). The complete open reading frame size of the *B. circulans* B2301 lactase encoding gene is 5133 bp, encoding 1710 amino acid residues, with no typical bacterial signal peptide sequences, and the highest similarity with the previously reported β-galactosidase is 93.6%; this enzyme shows the highest catalytic activity at 60° C. and pH 6.0-6.5. $Zn^{2+}$, $Fe^{2+}$, $Cu^{2+}$, EDTA and SDS show different degrees of inhibition on the enzyme. The $V_{max}$ of catalyzing the synthesis of galactooligosaccharide is 2.47 g/(L·h), $K_m$ is 14.37 g/L (Tian Kangming, et al., *Food and Fermentation Industries*, 2020).

However, the current fermentation of *B. circulans* to produce lactase is very uneconomical and requires a long fermentation time, usually 96 h-200 h; the level of enzyme production is also relatively low, usually only 2-5 U/mL of lactase can be produced (Zhao Jihua, et al., *Food and Fermentation Industries*, 2020). The process for the enzyme preparation is complex, most of the enzyme activity of lactase exists in the cells, and it needs to be released through complex cell disruption methods, and the quality of enzyme products is therefore greatly affected.

The coding gene of *B. circulans* lactase or its mutants was expressed in a variety of host cells to understand the expression level of lactase. For example, when expressed in *Escherichia coli*, the expression level of lactase is 1 to 3 U/mL, and it is hard to secrete lactase into the fermentation broth, which increases the difficulty of lactase preparations. When expressed in *Pichia pastoris* GS115, the expression level of shake flask fermentation can reach 70 U/mL, but it is also difficult to realize the secretory expression of lactase, and the separation and purification of the enzyme is also difficult.

SUMMARY

The purpose of the present invention is to obtain a novel strain with good performance of large-scale fermentation production and ideal lactase synthesis and secretion capabilities on the basis of obtaining excellent special enzyme molecules for galactooligosaccharide, which can significantly reduce manufacturing cost of the fermentation of lactase, simplify the fermentation manufacturing process of lactase, and significantly improved the quality of lactase preparations.

In order to achieve the above objectives, one of the technical solutions of the present invention is to provide a variety of lactase mutants, namely BglD305, BglD305-C, BglD305-D, BglD, BglD-C, BglD-D, BcBG168, BcBG168-C, BcBG168-D;

Among them, BglD305 is from *B. circulans* B2301 screened and isolated by the inventor (Zhao Jihua, et al., Establishment and preliminary application of a rapid screening method for high transglycosylation activity lactase, *Food and Fermentation Industries*, 2020), and the amino acid sequence is shown in the sequence table SEQ ID NO: 2; BglD305-C and BglD305-D are truncated sequences of BglD305 respectively, and the amino acid sequences are shown in SEQ ID NO: 4 and SEQ ID NO: 6 in the sequence listing;

Among them, BglD is from *B. circulans* ATCC 31382, and the amino acid sequence is shown in SEQ ID NO: 8; BglD-C and BglD-D are truncated sequences of BglD, respectively, and the amino acid sequences are shown in SEQ ID NO: 10 and SEQ ID NO: 12;

Among them, BcBG168 is obtained by DNA shuffling modification of BglD305 and BglD, BcBG168-C and BcBG168-D are obtained by further deleting the partial amino acid sequence of the C-terminal on the basis of BcBG168; The amino acid sequences of BcBG168, BcBG168-C and BcBG168-D are shown in SEQ ID NOS. 14, 16 and 18, respectively.

The second technical solution provided by the present invention is a recombinant vector or a recombinant strain containing the aforementioned lactase encoding gene;

Preferably, the expression vector used in the recombinant vector includes but is not limited to pHY-WZX (Niu, et al., 2007), pBL-WZX (Niu, et al., 2007), pHY300plk, pUB110, pE194, pHT1469 (MoBiTec), pWH1520 (Rygus and Hillen, 1991);

Preferably, the expression vector used in the recombinant vector includes, but is not limited to, pHSE-001, pHSE-002, pHSE-003, pHSE-004, pHSE-005, pHSE-006, pHSE-007, pHSE-008, pHSE-009, PHSE-010, pHSE-011, pHSE-012, pHSE-013, pHSE-014, pHSE-015, pHSE-016, pHSE-017, pHSE-018;

More preferably, the expression vector used in the recombinant vector is the pHSE-008 plasmid, which is based on the backbone of the expression vector pHY-WZX, and integrates the amylase promoter $P_{amyL}$ (SEQ ID NO: 20) derived from *Bacillus licheniformis* and signal peptide $S_{aprE}$ (SEQ ID NO: 23) of the alkali protease aprE;

Preferably, the expression host adopted by the recombinant strain includes but is not limited to *Bacillus subtilis, B. circulans, Bacillus megaterium, Bacillus pumilus, Bacillus amyloliquefaciens, Corynebacterium glutamicum, B. licheniformis*, and so on.

More preferably, the expression host used in the recombinant strain is the mutant strain BCBT0529, which is obtained by knocking out aprE, vpr; wpr lacR, lacA, lacA2, yesZ genes (The GenBank accession numbers corresponding to its gene sequence are: MT885340, MT885341, MT885342, MT885336, MT885337, MT885338, MT885339, respectively) from the genome of *B. licheniformis* CBB3008 (numbered CCTCC NO: M208236).

Preferably, the present invention provides a recombinant strain with high lactase production-*B. licheniformis* BCBTBc168D, which is obtained by integrating the BcBG168-D coding gene into the pHSE-008 plasmid and expressing it in the host cell mutant strain BCBT0529; The expression level of lactase BcBG168-D prepared by fermentation of *B. licheniformis* BCBTBc168D can reach 2208 U/mL.

The present invention also provides a method for fermentation and production of lactase using the above-mentioned recombinant strain:

(1) Shake flask fermentation to produce lactase: inoculating recombinant strain to shake flask culture medium, culturing at 30-45° C. and 120-270 r/min for 2-3 days;

Shake flask culture medium: yeast extract 0.5-1.5%, peptone 1.2-3.6%, glucose 8-20%; pH 7.0.

(2) Fermentation tank fermentation to produce lactase: inoculating the strain to the fermentation tank culture medium according to the inoculation amount of 5%-10%; during the fermentation process, the fermentation temperature is 33-45° C., the dissolved oxygen is controlled to 0.1%-20%, and the pH is 6.0-7.8, adding 30%-60% (w/w) maltose syrup and maintain the reducing sugar content at 0.1%-5%; fermentation lasts for 90-120 h, sampling and analyzing regularly during the fermentation process, the end of the fermentation is controlled as the increase value of fermentation enzyme activity less than 5-20 U/(mL·h).

The culture medium of the fermentation tank is composed of: 1%-5% of maltose syrup, 0%-5% of cottonseed powder, 0%-4% of corn syrup, 0.5-5% of soybean meal powder, 0.1-5% of ammonium sulfate, and pH 6.0-8.0.

After fermentation, the lactase activity of the fermentation broth in the shake flask fermentation can reach 25-54 U/mL; the lactase activity in the fermentation tank can reach 826-2208 U/mL.

Further, after the fermentation is completed, the strains are removed by simply filtration, and then filtered by an ultra-filtration system to obtain an enzyme solution.

The present invention also provides the application of the above-mentioned lactase in the production of galactooligosaccharides.

Beneficial Effects

The special enzyme preparation for the production of galactooligosaccharides in the present invention is a lactase with extremely high activity of catalyzing lactose to produce galactooligosaccharides obtained through gene cloning and artificial evolution; the lactase high-yielding strain of the present invention is recombinant strain by microorganisms breeding, which can efficiently synthesize lactase during submerged fermentation and secrete enzyme molecules into the culture medium, directly prepare high-activity enzyme preparations from the fermentation broth, and apply them to the high-efficiency production of galactooligosaccharides.

With the high-efficiency preparation method of lactase of the present invention, the expression level of lactase can reach 2208 U/mL under the lactase high-producing strain and fermentation process provided by the present invention. The invention helps to reduce the fermentation manufacturing cost of lactase, simplify the fermentation manufacturing process and improve the quality of the lactase enzyme preparation.

Figure 2:
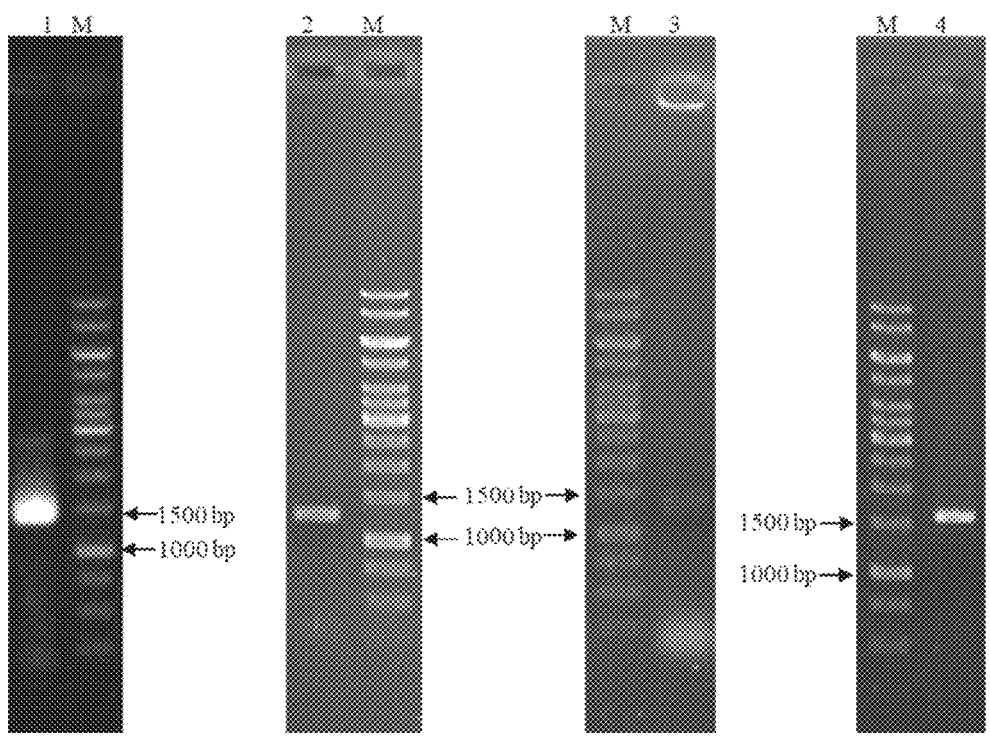

Lane M is the 1 kb molecular weight standard; Lane 1 is the mutant strain with the correct genome verification after the aprE gene is deleted, and the PCR amplification size is 1.5 kb; Lane 2 is the mutant strain with the correct genome verification after the protease wpr gene is deleted, and the PCR amplification size is 1.3 kb; Lane 3 is the mutant strain verified by the correct genome of the protease vpr deletion strain, and the PCR amplification size is 1.3 kb;

FIG. 2. is a validation map of knockout of coding genes such as endogenous lactase.

Figures 3A, 3B:
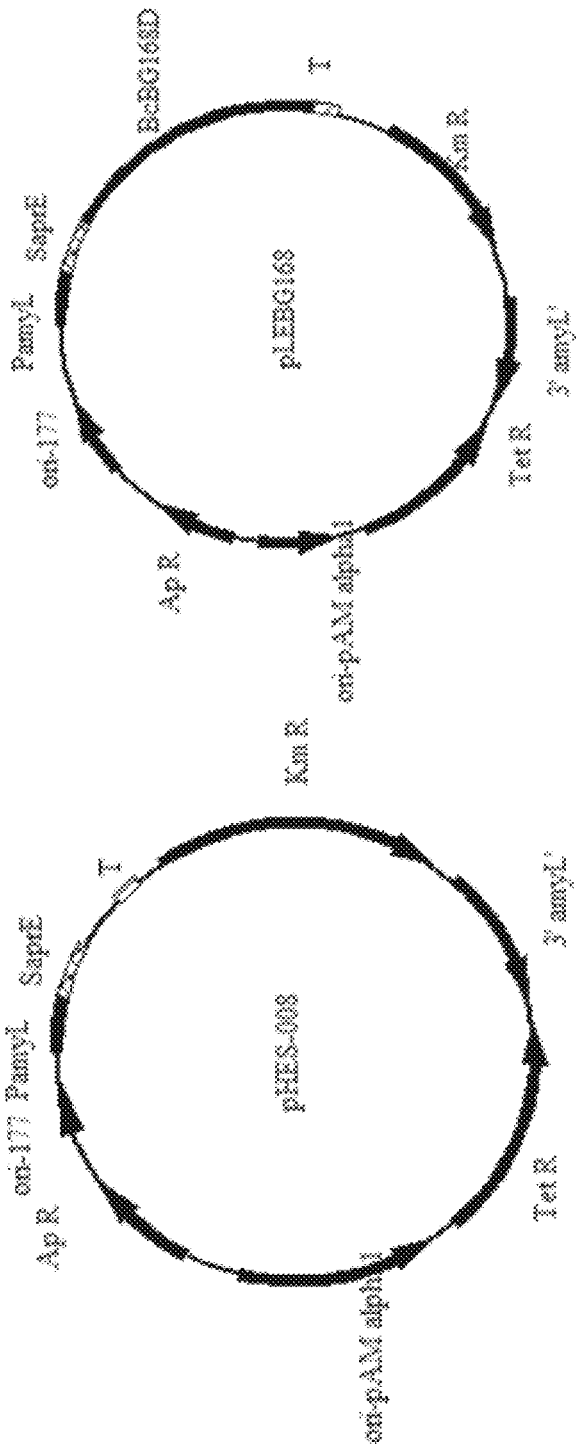
Figure 4:
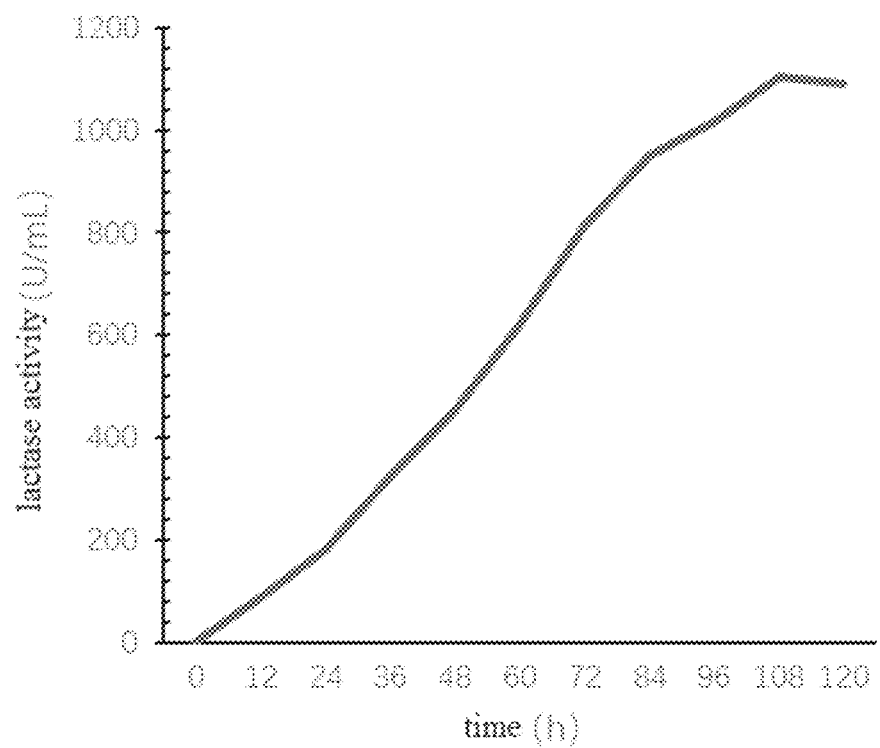

Lane M is the 1 kb molecular weight standard; Lane 1 is the electrophoretic pattern confirmed by PCR after the gene lacR is successfully knocked out, the size is 1.3 kb; Lane 2 is the electrophoretic pattern confirmed by PCR after the gene lacA is successfully knocked out, the size is 1.2 kb; Lane 3 is the electrophoretic pattern confirmed by PCR after the gene lacA2 is successfully knocked out, the size is 1.2 kb; Lane 4 is the electrophoretic pattern confirmed by the PCR after the gene yesZ is successfully knocked out, the size is 1.6 kb;

FIGS. 3A-3B show physical maps of expression vectors. FIG. 3A shows the optimized expression vector pHES-008; FIG. 3B shows the lactase expression plasmid pLEBG168;

FIG. 4. is an enzyme production curve of lactase fermentation.

Figure 5:
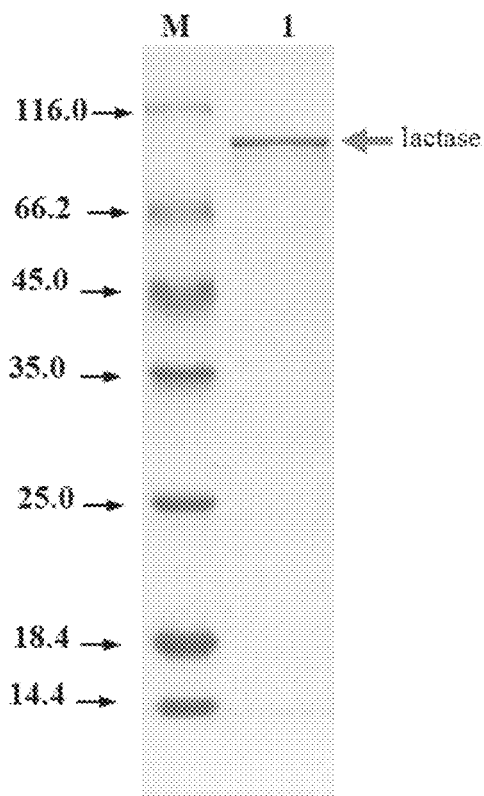

FIG. 5. is a protein electrophoresis pattern of fermentation broth.

Figure 6:
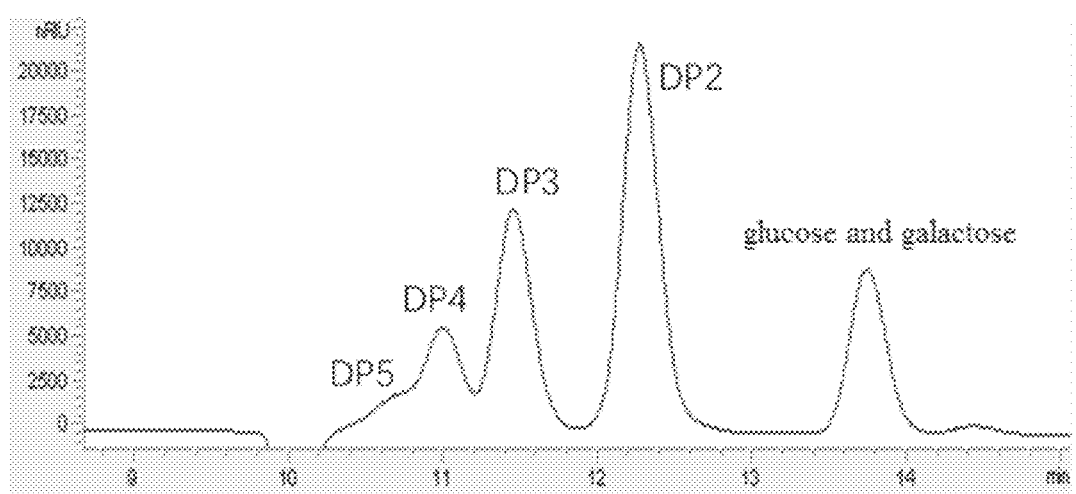

Lane M is the protein molecular weight standard; Lane 1 is the result of direct electrophoresis of the fermentation broth, and the arrow mark is the lactase in the fermentation broth;

FIG. 6. is a HPLC sugar spectrum of galactooligosaccharides produced by lactase from lactose DP2: galactobiose or lactose, DP3: glucosylgalactobiose or galactotriose; DP4: glucosylgalactotriose or galactotetraose; DP5: glucosylgalactotetraose or half lactopentaose.

DETAILED DESCRIPTION OF THE EMBODIMENTS

In order to make the purpose, technical solutions and advantages of this patent clearer, the following will further describe this patent in detail with reference to specific embodiments. It should be understood that the specific embodiments described here are only used to explain the patent, and not used to limit the present invention.

The plasmid pHY-WZX used in the present invention is the prior art, and its construction method has been disclosed in Niu D D and Wang Z X. Development of a pair of bifunctional expression vectors for *Escherichia coli* and *Bacillus licheniformis*. *J Ind Microbiol Biotechnol* (2007) 34:357-362. DOI 10.1007/s10295-0204-x. The public can also obtain it through the Biocatalysis and Biotransformation Laboratory of the College of Chemical Engineering and Materials Science, Tianjin University of Science and Technology.

The *B. licheniformis* CBB3008 used in the present invention has been deposited in the China Center for Type Culture Collection (CCTCC), the preservation date is Nov. 25, 2008, and the preservation number is CCTCC NO: M208236.

The present invention is based on two sources of lactase (BglD305 derived from *B. circulans* B2301 and BglD derived from *B. circulans* ATCC 31382) as the basis for molecular evolution, which are used to obtain new lactases (BglD305-C, BglD305-D, BglD-C, BglD-D, BcBG168, BcBG168-C, BcBG168-D), which have high efficiency in synthesis of galactooligosaccharides and good expression performance;

In the present invention, a host cell *B. licheniformis* CBB3008, has been deposited in the Chinese Type Culture Collection, and the preservation number is CCTCC NO: M208236, which is further genetically modified, multiple genes (alkaline protease coding gene aprE, minor serine protease coding gene vpr, cell wall protease coding gene wpr, regulatory protein coding gene lacR, β-galactosidase coding gene lacA, β-galactosidase coding gene lacA2, β-galactosidase encoding gene yesZ) affecting the expression of lactase are knocked out, to obtain a new host strain suitable for high-efficiency expression of lactase;

The present invention constructs and optimizes an expression vector suitable for secretion and expression of lactase, which is optimized on the basis of pHY-WZX. The expression vector contains a preferred promoter for guiding high expression of lactase and a signal peptide that efficiently mediates secretion and expression of lactase;

In the present invention, the coding genes of *B. circulans* lactase (corresponding to SEQ ID NOS. 1, 3, 5, 7, 9, 11, 13, 15, 17) or their respective mutants (corresponding to SEQ ID NOS. 2, 4, 6, 8, 10, 12, 14, 16, 18) are cloned into the expression vector constructed in the present invention, genetically transformed into *B. licheniformis* host strains to obtain lactase-producing recombinant strain. The fermentation conditions and process are established and optimized. A new process of enzyme separation, purification and refining are developed to produce lactase products for the industrial manufacturing of GOS.

The method for constructing a new strain with high lactase yield of the present invention is to clone an expression vector by molecular cloning technology and obtain an expression plasmid for lactase, and transform it into a new host strain of *B. licheniformis* to obtain recombinants to realize lactase high-efficiency secretion and expression. The enzyme synthesis and secretion system is optimized to reach high-efficiency secretion of the synthesized lactase into the medium. And through the fermentation process, lactase is recovered and refined from the fermentation broth to obtain lactase products.

The main experimental methods used in the present invention are as follows:

1. Gene Cloning, Molecular Evolution and Construction of Expression Plasmid

Conventional molecular cloning operations were carried out with reference methods (Sambrook et al. Molecular Cloning: A Laboratory Manual, 1989). The coding gene of *B. circulans* lactase or its mutants was used as the target gene in the present invention; the basic expression vector was pHY-WZX (The pHY-WZX sequence was shown in SEQ ID NO: 72; Niu & Wang. *J Ind Microbiol Biotechnol,* 2007).

2. Chromosomal DNA Extraction

The chromosomal DNA extraction method was carried out according to the literature (Zhuge Jian and Wang Zhengxiang. Manual of Industrial Microbiology Experiment Technology, China Light Industry Press, 1994).

3. Plasmid DNA Extraction

The plasmid DNA was extracted using a certain concentration of lysozyme to lyse the cell wall and using Sigma's plasmid small extraction kit.

4. Gene Amplification

DNA amplification was performed in 0.2 mL PCR thin-walled tubes. The PCR amplification conditions are: 1×(95° C., 5 min); 30×(94° C., 10 s; 58° C., 30 s, 72° C., 30-300 s); 1×(72° C. 10 min). Depending on the length of the amplification, the extension temperature and time of the PCR reaction were different. Unless otherwise specified, all PCR reactions were performed with Pfu DNA polymerase.

5. Artificial Evolution of Enzyme Molecules

The molecular evolution of lactase was carried out using DNA shuffling according to the literature method (Stemmer W P C, et al., Rapid evolution of a protein in vitro by DNA shuffling [J]. *Nature,* 1994, 370(6488): 389-391). Firstly, the lactase gene was partially digested with DNase, and the 100-200 bp fragments were recovered by the density gradient method. After mixing, the gene amplification was performed for 15-25 cycles without primers, and then specific primers at both ends were added to amplify the full-length gene; PCR product purification kit (Sigma) was used for purification, the purified DNA was cloned into the expression vector pHY-WZX, $CaCl_2$) method was used (Zhuge Jian and Wang Zhengxiang. Industrial Microbiology Experimental Technology Manual, China Light Industry Press, 1994) to transform into *E. coli* JM109; the lactase activity was measured and compared.

6. Overlap PCR

Refer to the literature (Krishnan B R, et al. Direct and crossover PCR amplification to facilitate Tn5supF-based sequencing of lambda phage clones. *Nucleic Acids Research,* 1991, 22: 6177-82). The general steps were: using the primers of fragment F1 and fragment F2 (P1+P2; P3+P4, primers P2 and P3 were reverse complementary sequences) to mediate PCR amplification to obtain gene fragments; gel recovery and purification of amplified fragment F1 And F2; the purified two fragments F1 and F2 were diluted by an appropriate multiple, and mixed with a 1:1 molar ratio as a template, and primers P1+P4 were used to mediate a new PCR reaction to obtain a full-length sequence.

7. *B. licheniformis* Genetic Transformation

Refer to the method introduced in the literature (Xu Min, Ma Junshuang, Wang Zhengxiang. The effect of high osmotic pressure on the electrical conversion rate of bacteria. *Journal of Wuxi University of Light Industry,* 2004(04): 98-100). The main steps were as follows: fresh single colony was inoculated into liquid LB medium, and cultivated overnight at 37° C. at 200 r/min, then 5% inoculation amount was transferred to new LB medium and continued to cultivate until the OD600 was 0.75-0.90. The cells were collected by centrifugation at 6000 r/min at 40° C. for 10 min after ice bath for 10 min. The cells were repeatedly washed 4 times with pre-cooled electroporation washing solution (0.5 mol/L sorbitol, 0.5 mol/L mannitol and 10% glycerol). The cell pellet was suspended in 1 mL of pre-cooled electroporation washing solution to complete the preparation of competent cells. 1 μL of plasmid DNA and about 100 μL of competent cells were taken to mix, and were immediately electroporated (1800 v, 5 ms), then electroporation resuscitation solution (LB medium containing 0.65 mol/L sorbitol and 0.45 mol/L mannitol) was added, after recovery at 37° C., 160 r/min, the system was then spread on the corresponding resistant LB plate and cultivated at the appropriate temperature until a single colony grew. The correct transformants were verified by colony PCR verification, plasmid extraction, enzyme digestion, and fermentation verification methods.

8. Deletion of Specific Genes in *B. licheniformis*

Reference method (Cai D, et al High-level expression of nattokinase in *B. licheniformis* by manipulating signal peptide and signal peptidase. *J Appl Microbiol.* 2016, 121: 704-712) was performed. The deletion of aprE gene in *B. licheniformis* CCTCC NO: M208236 was taken as an example, the general procedure was as follows: *B. licheniformis* genomic DNA was used as a template, apr-up1 (SEQ ID NO: 30) and apr-up2 (SEQ ID NO: 31) and primer apr-dn1 (SEQ ID NO: 32) and apr-dn2 (SEQ ID NO: 33) were primers to amplify the upper and lower homology arm fragments respectively to obtain the correct size PCR products and then gel recovery was used to purify them, and gel recovery product DNA was used as a template to overlap by PCR, the deletion mutation box ΔaprE was obtained. The mutant cassette was purified and digested with Xba I and cloned into the Sma I and Xba I locus of the plasmid pT2$^{ts}$ (pT2$^{ts}$ is based on T2(2)-ori (Chen Shouwen, etc., Chinese invention patent, ZL201310562150.7) as the starting plasmid, after reverse amplification of primers T2-1 (SEQ ID NO: 28), T2-2 (SEQ ID NO: 29) was performed, the PCR product was self-circularized and ligated to obtain the new plasmid pT2$^{ts}$), and was transformed into *E. coli* JM109 competent cells, and cultured on LB plate with 20 μg/mL kanamycin to obtain the correct deletion plasmid pT2-ΔaprE. According to the steps described in the genetic transformation method of *B. licheniformis*, the deletion plasmid pT2-ΔaprE was transformed into *B. licheniformis* host cells. After two homologous recombination, the primers apr-F: (SEQ ID NO: 34) and apr-R (SEQ ID NO: 35) were designed on both sides of the homology arm, and colony PCR was performed with these primers to verify the transformants (other genes for deletion, refer to the above method, design and replace primers according to the deleted gene sequence).

9. Fermentation Test

Shake flask fermentation to produce lactase: 30 mL fermentation medium (yeast extract 0.5-1.5%, peptone 1.2-3.6%, glucose 8-20%; pH 7.0) were added in a 250 mL Erlenmeyer flask, the recombinant strain was inoculated and incubated at 30-45° C., under 120-270 r/min for 2 to 3 days.

Fermentation tank to produce lactase: the composition of the fermentation medium was: 1% to 5% of maltose syrup, 0% to 5% of cottonseed meal, 0% to 4% of corn syrup, 0.5 to 5% of soybean meal, and 0.1 to 5% of ammonium sulfate, pH 6.0-8.0; fermentation was carried out in a 50 L-10 ton fermentation tank, with an inoculum amount of 5%-10%; during the fermentation process, the fermentation temperature was 33-45° C., the dissolved oxygen was controlled at 0.1%-20%, and the pH was 6.0-7.8. 30%-60% (w/w) maltose syrup was added, and the reducing sugar content was maintained at 0.1%-5%; fermentation was lasted for 90-120 h, sampling and analysis were performed during the fermentation process, the end of the fermentation was controlled when the increased value of the enzyme activity is less than 5-20 U/(mL·h).

10. Preparation Method of Lactase Preparation

After the fermentation, the strains were removed by filtration, and then filtered by an ultrafiltration system to obtain the enzyme solution.

11. Lactase Activity Determination

The enzyme activity determination of lactase is improved in accordance with the Chinese National Standard GB/T 33409-2016. The general process is that the reaction is carried out at pH 5.0 and 40° C. with lactose as the substrate. A biosensor was used to determine the amount of glucose released.

The enzyme activity of lactase is defined as the amount of enzyme required to decompose lactose to produce 1 micromole of glucose per minute at pH 5.0 and 40° C., which is defined as one unit (U), expressed in U/mL or U/g.

12. Synthesis and Product Analysis of Galactooligosaccharides

Using 300 g/L-800 g/L lactose as the substrate, adding 5 U/g-20 U/g lactase, the reaction is carried out at 50° C.-70° C., and sampling is done regularly. For the analysis of the formation and content of reaction raw materials and galactooligosaccharides, the characteristics and formation of enzymatic products were analyzed by HPLC. The chromatographic conditions were: the mobile phase was 65% acetonitrile, the flow rate was 1.0 mL/min; the TSK-GEL G3000PWXL-CP (7.8 mm×300 mm, 7 μm) chromatographic column, the column temperature was 25° C.; the evaporative light scattering detector, the drift tube temperature was 90° C., the carrier gas flow rate was 2.2 mL/min.

13. Other Analysis Methods

Protease activity determination was carried out in accordance with the Chinese National Standard method (GB/T 23527-2009);

Gene and amino acid sequence comparison, DNAMAN software was used;

The nucleotide sequence determination was carried out by the Sanger method;

Sequence protein content was carried out according to literature method (Bradford. *Anal Chem*, 1976);

Glucose content was determined by enzyme electrode method (SBA-90, Shandong);

The cell density was measured with a spectrophotometer (UV-2000, USA) at 600 nm;

Protein electrophoresis was carried out according to the literature method (Zhuge Jian and Wang Zhengxiang. Manual of Industrial Microbiology Experiment Technology, China Light Industry Press, 1994).

The following will further explain the present invention through specific embodiments.

Example 1: Molecular Evolution of Lactase

The BglD305 and BglD coding genes shown in SEQ ID NO: 1 and SEQ ID NO: 7 in the sequence table was used as a template, DNA shuffling was used to carry out molecular evolution. After the enzyme activity screening, the lactase enzyme molecule BcBG168 (nucleotide sequence SEQ ID NO: 13) with significantly increased enzyme activity level was obtained, and its amino acid sequence (amino acid sequence SEQ ID NO: 14) was obtained.

By truncating the coding genes of BglD305, BglD and BcBG168 with varying degrees, and efficiently expressing the modified sequences and the original sequence, the corresponding gene sequences were amplified by PCR amplification technology and cloned into the expression vector pHY-WZX to obtain lactase expression plasmid pHY-Bgl-1, pHY-Bgl-2, pHY-Bgl-3, pHY-Bgl-4, pHY-Bgl-5, pHY-Bgl-6, pHY-Bgl-7, pHY-Bgl-8, pHY-Bgl-9, pHY-Bgl-10, pHY-Bgl-11, pHY-Bgl-12. The above recombinant plasmids were transformed into *B. licheniformis* CCTCC NO: M208236 by the above-mentioned *B. licheniformis* genetic transformation method, and corresponding transformants CBB-Bgl-1, CBB-Bgl-2, CBB-Bgl-3, CBB-Bgl-4, CBB-Bgl-5, CBB-Bgl-6, CBB-Bgl-7, CBB-Bgl-8, CBB-Bgl-9, CBB-Bgl-10, CBB-Bgl-11, CBB-Bgl-12 were obtained, shake flask fermentation and analysis of enzyme production (enzyme activity determination on the supernatant of the fermentation broth) were further carried out, the main content and enzyme production results are shown in Table 1.

Under the same conditions, the expressed enzyme activity of BcBG168 was 103.2% of BglD305 and 109.8% of BglD, respectively.

The C-terminal truncated lactase of lactase showed an upward trend under the same expression conditions. Compared with the original gene sequence, the enzyme activity increased by 40%, 78%; 35%, 69% and 31%, 70%.

TABLE 1

Expression efficiency of lactase from different sources and C-terminal truncation

| Strains | Lactase expression and its sequence (nucleotide sequence is shown first, then amino acid sequence) | | Enzyme activity (U/mL) |
|---|---|---|---|
| CBB-Bgl-1 | BglD305 | SEQ ID NO: 1 (SEQ ID NO: 2) | 3.21 ± 0.15 |
| CBB-Bgl-2 | BglD305-C | SEQ ID NO: 3 (SEQ ID NO: 4) | 4.52 ± 0.17 |
| CBB-Bgl-3 | BglD305-D | SEQ ID NO: 5 (SEQ ID NO: 6) | 5.74 ± 0.21 |
| CBB-Bgl-7 | BglD | SEQ ID NO: 7 (SEQ ID NO: 8) | 3.56 ± 0.11 |
| CBB-Bgl-8 | BglD-C | SEQ ID NO: 9 (SEQ ID NO: 10) | 4.82 ± 0.14 |
| CBB-Bgl-9 | BglD-D | SEQ ID NO: 11 (SEQ ID NO: 12) | 6.03 ± 0.20 |
| CBB-Bgl-10 | BcBG168 | SEQ ID NO: 13 (SEQ ID NO: 14) | 3.82 ± 0.16 |
| CBB-Bgl-11 | BcBG168-C | SEQ ID NO: 15 (SEQ ID NO: 16) | 5.02 ± 0.17 |
| CBB-Bgl-12 | BcBG168-D | SEQ ID NO: 17 (SEQ ID NO: 18) | 6.48 ± 0.22 |

Example 2: Genetic Modification of Expression Host Cells

Figure 1:
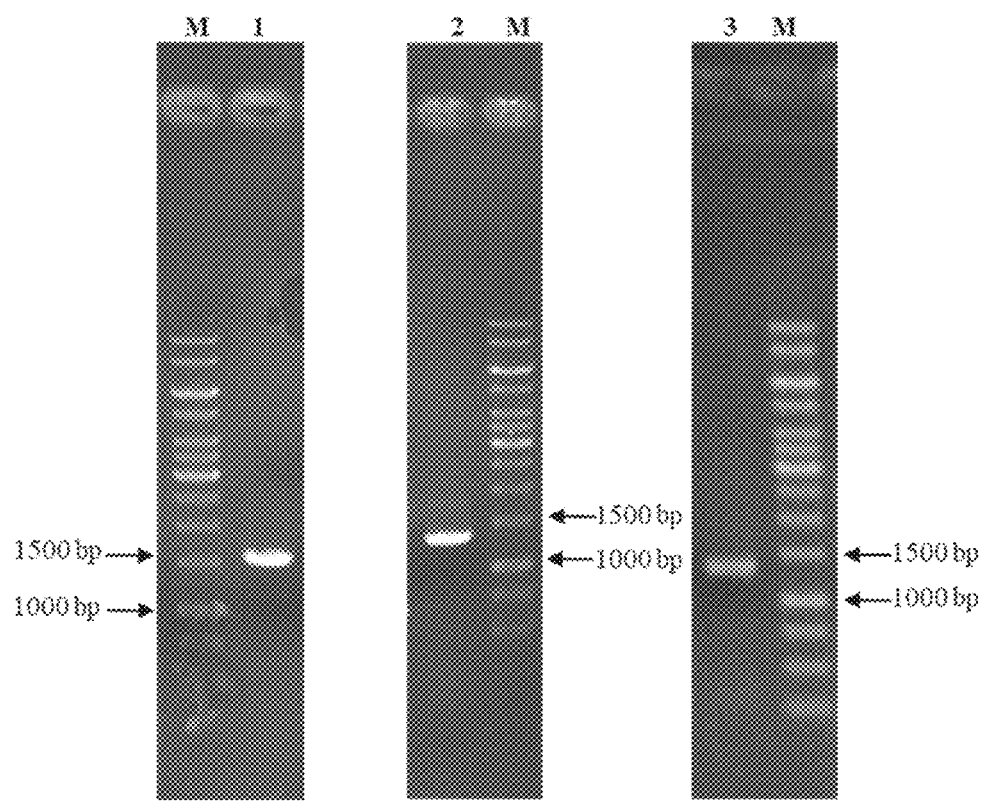
FIG. 1. is a validation map of protease-encoding gene knockout.

Deletion of aprE gene in *B. licheniformis* CCTCC NO: M208236. *B. licheniformis* CCTCC NO: M208236 genomic DNA was used as a template, apr-up1 (SEQ ID NO: 30) and apr-up2 (SEQ ID NO: 31) and primers apr-dn1 (SEQ ID NO: 32) and apr-dn2 (SEQ ID NO: 33) were used as primers, the upper and lower homology arm fragments were respectively amplified, the sizes were 667 bp and 495 bp, respectively. After obtaining the PCR products of the correct size, they were purified by gel recovery, and overlap PCR was performed using the gel recovered product DNA as a template to obtain a deletion mutation box ΔaprE with a size of ~1.2 kb. The mutant box was purified and digested with Xba I, cloned into the Sma I and Xba I sites of plasmid pT2$^{ts}$, transformed into *E. coli* JM109 competent cells, and cultured on LB plates containing 20 μg/mL kanamycin to obtain the correct deletion plasmid pT2-ΔaprE. Following the steps described in the "Genetic transformation of *B. licheniformis*" method, the deletion plasmid pT2-ΔaprE was transformed into the *B. licheniformis* CCTCC NO: M208236. After two homologous recombination, the primers apr-F (SEQ ID NO: 34) and apr-R (SEQ ID NO: 35) were designed on both sides of the homology arm, and colony PCR was performed with these primers to verify that the correct transformant BCBT01 was obtained, the size of the PCR product for correct transformant is ~1.5 kb (FIG. 1, lane 1).

*B. licheniformis* CCTCC NO: M208236 β-galactosidase encoding gene lacA deletion. The method similar to the above aprE gene deletion was used. *B. licheniformis* CCTCC NO: M208236 genomic DNA was used as template, lacA-up1 and lacA-up2 (SEQ ID NO: 36 and SEQ ID NO: 37, respectively) and primers lacA-dn1 and lacA-dn2 (SEQ ID NO: 38 and SEQ ID NO: 39, respectively) were used as primers to respectively amplify the upper and lower homology arm fragments, 486 bp and 500 bp in size, respectively. After obtaining the PCR products of the correct size, they were purified by gel recovery, and overlap PCR was performed using the gel recovered product DNA as a template to obtain a deletion mutation box ΔlacA with a size of 936 bp. The mutant box was purified and digested with Xba I, cloned into the Sma I and Xba I sites of plasmid pT2$^{ts}$, transformed into E. coli JM109 competent cells, and cultured on LB plates containing 20 μg/mL kanamycin to obtain the correct deletion plasmid pT2-ΔLacA. The deletion plasmid pT2-ΔLacA was transformed into B. licheniformis according to the steps described in the "Genetic Transformation of B. licheniformis" method. After two homologous recombination, using the primers lacA-F and lacA-R (SEQ ID NOS: 40 and 41, respectively) on both sides of the homology arm to verify the correct transformant by colony PCR. The PCR product size of the correct transformant was ~1.2 kb (FIG. 2, lane 2).

Using the above-mentioned similar method, the vpr; wpr; lacR, lacA2 and yesZ genes in the genome of B. licheniformis CCTCC NO: M208236 were deleted in different combinations, where vpr corresponds to the homology primers and the verification primers are SEQ ID NOS: 42-47; wpr corresponds to the homology primers and the verification primers are SEQ ID NOS: 48-53; lacR corresponds to the homology primers and verification primers are the SEQ ID NOS: 54-59; lacA2 corresponds to the homology primers and verification primers are the SEQ ID NOS: 60-65; yesZ corresponds to the homology primers and verification primers are SEQ ID NOS: 66-71, and different defective mutants were obtained. Among them, mutant BCBT03-15, renamed BCBT0529, its genetic background was (CBB3008, ΔaprE, Δvpr, Δwpr, ΔlacR, ΔlacA, ΔlacA2, ΔyesZ).

Example 3 the Effect of Knocking Out Some Genes on Host Cell Expression (1) The Effect of Partial Proteases Knockout on Extracellular Protease Activity The different mutant strains obtained in Example 2 were subjected to a shake flask fermentation test, and their extracellular protease activity was analyzed. As shown in Table 2, after deleting the alkaline protease encoding gene aprE, the total enzyme activity of proteolytic enzymes in the medium was reduced by 80%. After further deleting the two proteases encoding gene vpr and wpr, the total enzyme activity of proteolytic enzymes in the medium drops to 10% of the wild type.

TABLE 2

Determination of alkaline protease activity of mutant strains

| Strains | Genotype | Extracellular protease activity (U/mL) |
|---|---|---|
| CCTCC NO: M208236 | Original strain | 560 ± 20 |
| BCBT01 | ΔaprE | 112 ± 12 |
| BCBT02 | ΔaprEΔvpr | 82 ± 9 |
| BCBT03 | ΔaprEΔvprΔwpr | 58 ± 7 |

(2) The Effect of Partial Proteases Knockout on the Expression of Lactase

The expression plasmid pHY-bgl-12 carried in the recombinant CBB-Bgl-12 with the highest enzyme-producing activity obtained in Example 1 was transformed into the host with the proteolytic enzyme gene deleted obtained in Example 2 to obtain the corresponding recombinants, with CCTCC NO: M208236 as a control. The results of recombinants in shake flask fermentation are shown in Table 3. After deleting the alkaline protease gene aprE, the lactase activity in the fermentation broth increased significantly, reaching 10.68 U/mL, an increase of 41.08%; after deleting the other two proteolytic enzyme genes vpr and wpr, the lactase activity in the fermentation broth further increased (12.12 U/mL), which was 60% higher than the original strain.

TABLE 3

The expression level of lactase after deleting the proteases

| Host | Strains | Lactase activity (U/mL) |
|---|---|---|
| CCTCC NO: M208236 | / | 0.15 ± 0.03 |
| CCTCC NO: M208236 | CBB-Bgl-12 | 7.57 ± 0.24 |
| BCBT01 | BCBT01-Bgl-12 | 10.68 ± 0.44 |
| BCBT02 | BCBT02-Bgl-12 | 11.72 ± 0.18 |
| BCBT03 | BCBT03-Bgl-12 | 12.12 ± 0.28 |

(3) The Effect of Specific Gene Knockout on the Expression of Lactase

Table 4 shows the changes in lactase activity of the host cell after their endogenous lactase-related genes are mutated under shaking flask fermentation conditions. It can be seen that after the deletion of the alkaline protease encoding gene aprE and the lactose operon repressor protein encoding gene lacR, the lactase activity in the fermentation broth has increased. After further deletion of the related endogenous lactase structural genes, the lactase activity in the fermentation broth is too low to be measured according to existing methods.

TABLE 4

Lactase enzyme activity of endogenous lactase gene mutant strain

| Strains | Genes | Lactase activity (U/mL) |
|---|---|---|
| CCTCC NO: M208236 | Parent strain | 0.15 ± 0.03 |
| BCBT03 | ΔaprEΔvprΔwpr | 0.14 ± 0.05 |
| BCBT03-1 | ΔaprE ΔvprΔwprΔlacR | 2.86 ± 0.09 |
| BCBT03-2 | ΔaprE ΔvprΔwprΔlacA | n.d.* |
| BCBT03-3 | ΔaprEΔvprΔwprΔlacA2 | 0.12 ± 0.02 |
| BCBT03-4 | ΔaprE ΔvprΔwprΔyesZ | 0.13 ± 0.02 |
| BCBT03-5 | ΔaprEΔvprΔwprΔlacRΔlacA | n.d.* |
| BCBT03-6 | ΔaprEΔvprΔwprΔlacRΔlacA2 | 2.61 ± 0.02 |
| BCBT03-7 | ΔaprE ΔvprΔwprΔlacR ΔyesZ | 2.60 ± 0.04 |
| BCBT03-8 | ΔaprE ΔvprΔwprΔlacA ΔlacA2 | n.d.* |
| BCBT03-9 | ΔaprEΔvprΔwprΔlacAΔyesZ | n.d.* |
| BCBT03-10 | ΔaprE ΔvprΔwprΔlacA2ΔyesZ | 2.72 ± 0.03 |
| BCBT03-11 | ΔaprE ΔvprΔwprΔlacRΔlacAΔlacA2 | n.d.* |
| BCBT03-12 | ΔaprE ΔvprΔwprΔlacRΔlacAΔyesZ | n.d.* |
| BCBT03-13 | ΔaprEΔvprΔwprΔlacRΔlacA2ΔyesZ | 2.58 ± 0.04 |
| BCBT03-14 | ΔaprE ΔvprΔwprΔlacAΔlacA2ΔyesZ | n.d.* |
| BCBT03-15 | ΔaprE ΔvprΔwprΔlacRΔlacAΔlacA2ΔyesZΔlacA | n.d.* |

*n.d.: Enzyme activity is not detected

Example 4: Efficient Expression of Lactase

The plasmid pHY-bgl-12 was transformed into the strains with different endogenous lactase genes deletion obtained in Example 2, and the recombinants were constructed and subjected to shake flask fermentation. The lactase activity in the fermentation broth was determined. The results are shown in Table 5. After the endogenous lactase-related genes of the host cell were deleted, it was found that the expression level of lactase of the present invention was greatly increased. Among them, BCBT03-15 had the highest enzyme activity when BCBT0529 was used as the host cell, and was 4.47 times of the enzyme activity when strain CCTCC NO: M208236 was used as the host cell.

TABLE 5

The expression level of lactase after deletion of endogenous lactase

| Host | Strains | Lactase activity (U/mL) |
| --- | --- | --- |
| CCTCC NO: M208236 | CBB-Bgl-12 | 7.57 ± 0.24 |
| BCBT03-1 | BCBT03-1-Bgl-12 | 13.63 ± 0.38 |
| BCBT03-2 | BCBT03-2-Bgl-12 | 28.25 ± 2.42 |
| BCBT03-3 | BCBT03-3-Bgl-12 | 7.87 ± 0.34 |
| BCBT03-4 | BCBT03-4-Bgl-12 | 7.02 ± 0.46 |
| BCBT03-5 | BCBT03-5-Bgl-12 | 30.56 ± 1.46 |
| BCBT03-6 | BCBT03-6-Bgl-12 | 12.27 ± 0.32 |
| BCBT03-7 | BCBT 03-7-Bgl-12 | 12.89 ± 0.53 |
| BCBT03-8 | BCBT03-8-Bgl-12 | 32.25 ± 1.79 |
| BCBT03-9 | BCBT03-9-Bgl-12 | 31.37 ± 1.43 |
| BCBT03-10 | BCBT03-10-Bgl-12 | 11.76 ± 0.29 |
| BCBT03-11 | BCBT03-11-Bgl-12 | 32.68 ± 1.54 |
| BCBT03-12 | BCBT03-12-Bgl-12 | 32.83 ± 2.96 |
| BCBT03-13 | BCBT03-13-Bgl-12 | 15.65 ± 0.78 |
| BCBT03-14 | BCBT03-14-Bgl-12 | 32.92 ± 1.87 |
| BCBT03-15 (BCBT0529) | BCBT03-15-Bgl-12 | 33.87 ± 2.65 |

*n.d.: Enzyme activity is not detected.

On the basis of determining the optimal host cell, the expression element was further optimized, and the expression vector was modified by the combination of different promoters and different signal peptides to increase the expression level of lactase.

Based on the plasmid pHY-WZX as the backbone of the expression vector, three different constitutive promoters were selected, which were $P_{cry}$ (SEQ ID NO: 19, *Bacillus thuringiensis* insecticidal protein gene promoter), $P_{amyL}$ (SEQ ID NO: 20, *Bacillus licheniformis* amylase gene promoter), $P_{43}$ (SEQ ID NO: 21, *Bacillus subtilis* cytidine deaminase gene promoter) and 6 different signal peptides were selected, which were $S_{amyL}$ (SEQ ID NO: 22, *Bacillus licheniformis* amylase gene signal peptide), $S_{aprE}$ (SEQ ID NO: 23, *Bacillus licheniformis* alkaline protease signal peptide), $S_{amyQ}$ (SEQ ID NO: 24, *Bacillus amyloliquefaciens* amylase gene signal peptide), $S_{amyE}$ (SEQ ID NO: 25, *Bacillus subtilis* amylase gene signal peptide), $S_{nprE}$ (SEQ ID NO: 26, *Bacillus licheniformis* neutral protease gene signal peptide), $S_{chi}$ (SEQ ID NO: 27, *Bacillus licheniformis* chitinase gene signal peptide), replacing the original promoter and signal peptide on pHY-WZX with different combinations to construct 18 species new expression vectors pHSE-001-018 (see Table 6 for details). The BcBG168-D coding gene was cloned into the above 18 species new expression vectors and transformed into *B. licheniformis* BCBT0529 to obtain a series of recombinants, which were subjected to shake flask fermentation and determined enzyme activity. The results are summarized in Table 6. The tested 18 combinations of promoters and signal peptides can all mediate the secretion and expression of lactase BcBG168-D in *B. licheniformis*. Among them, the expression plasmid pHSE-008 (FIG. 3A), which is composed of a combination of the amylase promoter $P_{amyL}$ derived from the *B. licheniformis* and the signal peptide of the alkaline protease aprE, can mediate the highest enzyme expression, and the obtained lactase expression plasmid is pLEBG168 (The BcBG168-D coding gene was cloned into the expression plasmid pHSE-008, FIG. 3B); the obtained strain BCBTBc168D (The BcBG168-D coding gene sequence was cloned into the expression plasmid pHSE-008 and then transformed into *Bacillus* licheniformis host cell BCBT0529) expresses lactase activity of 53.79 U/mL in shake flask fermentation, more than 20 times of the enzyme production level of the wild strain, and more than 7 times that of the host cell before genetic modification and signal peptide optimization.

TABLE 6

The effect of different promoter and signal peptide combinations on the expression of lactase BcBGL68-D

| Host | Expression plasmid | Expression element assembly | | Lactase activity (U/mL) |
| --- | --- | --- | --- | --- |
| | | Promoter | Signal peptide | |
| B2301 | / | / | / | 2.5 U/mL |
| CCTCC NO: M208236 | pHY-WZX | $P_{amyL}$ | $S_{amyL}$ | 7.57 ± 0.24 |
| BCBT0529 | pHSE-001 | $P_{cry}$ | $S_{amyL}$ | 23.35 ± 1.82 |
| | pHSE-002 | | $S_{aprE}$ | 26.93 ± 2.15 |
| | pHSE-003 | | $S_{amyQ}$ | 20.36 ± 1.27 |
| | pHSE-004 | | $S_{amyE}$ | 23.78 ± 1.93 |
| | pHSE-005 | | $S_{vprE}$ | 17.85 ± 1.62 |
| | pHSE-006 | | $S_{chi}$ | 19.46 ± 1.35 |
| | pHSE-007 (pHY-WZX) | $P_{amyL}$ | $S_{amyL}$ | 33.26 ± 2.12 |
| | pHSE-008 | | $S_{aprE}$ | 53.79 ± 3.24 |
| | pHSE-009 | | $S_{amyQ}$ | 28.36 ± 2.17 |
| | pHSE-010 | | $S_{amyE}$ | 25.58 ± 1.97 |
| | pHSE-011 | | $S_{vprE}$ | 20.67 ± 1.23 |
| | pHSE-012 | | $S_{chi}$ | 16.39 ± 1.17 |
| | pHSE-013 | $P_{43}$ | $S_{amyL}$ | 30.68 ± 2.17 |
| | pHSE-014 | | $S_{aprE}$ | 38.56 ± 2.78 |
| | pHSE-015 | | $S_{amyQ}$ | 29.32 ± 1.18 |
| | pHSE-016 | | $S_{amyE}$ | 23.93 ± 1.69 |
| | pHSE-017 | | $S_{vprE}$ | 12.15 ± 0.57 |
| | pHSE-018 | | $S_{chi}$ | 19.56 ± 1.18 |

Example 5: Lactase Fermentation Production Process Under 50 L Fermentation System The lactase high-producing strain BCBTBc168D was cultured at 37° C. for 20-40 h, and 2-3 single colonies were picked and inoculated into 2 bottles of 5 L Erlenmeyer flasks containing 1000 mL LB liquid medium at 37° C., 230 r/min, and cultured on a shaker for 16 h, as seed liquid. Seed liquid was inoculated into a 50 L automatic fermentation tank containing 30 L fermentation medium (maltose syrup 4%, cottonseed powder 2.5%, soybean meal powder 3.5%, ammonium sulfate 0.5%, pH 6.5) according to the inoculum amount of 5%. The fermentation volume was 30 L. During the process, the dissolved oxygen was maintained at 0.1%-20% by adjusting the rotation speed and aeration, the fermentation temperature was 40-42° C., and the pH was controlled to 6.5±0.5, and 60% (w/w) maltose syrup was added as a carbon source, and the reducing sugar content was maintained at 0.5-5%. Regular sampling and analysis of the amount of residual sugar and enzyme activity were carried out, fermentation was performed to 120 hours, when the enzyme activity increase rate was less than 5 U/(mL·h), the fermentation was stopped for preparing the enzyme preparation.

The typical production process curve of lactase is shown in FIG. 4. The enzyme protein in the fermentation broth was the most important protein molecules (FIG. 5), and the highest lactase activity in fermentation broth reached 1131 U/mL (at 108 h), which was approximately 21 times of shake flask fermentation.

Similarly, BglD305-D and BglD-D were expressed in *B. licheniformis* BCBT0529 using pHSE-008 as the expression vector under the mediated combination of the *Bacillus licheniformis* amylase promoter $P_{amyL}$ and the signal peptide $S_{aprE}$ of the alkaline protease AprE, the lactase high-producing strains BCBT305D and BCBTatccD obtained respectively, under the above fermentation conditions, the lactase production levels reached 820 U/mL and 870 U/mL, respectively.

Example 6: Fermentation Production and Preparation of Lactase

According to the process of the 50 L fermentor in Example 5, the BCBTBc168D strain was used to prepare lactase under a 10-ton fermentation system after adjusting the operation process accordingly. After the fermentation, the lactase activity in the fermentation broth reached 2208 U/mL.

After the fermentation is finished, biological flocculant (polyacrylamide: basic aluminum chloride=8:1) was added to the fermentation broth according to 1.0%, 2% diatomite TS-20 # was added after the flocculation was completed, and then plate and frame filtration was carried out for sterilization. The membrane material with a molecular weight cutoff of 30 kDa was selected for ultrafiltration and concentration, and the operating pressure was 0.05 MPa at 40° C. for 2 h.

After ultrafiltration, 1% sodium benzoate, 1% potassium sorbate, 2% sodium chloride, 10% sorbitol, and 10% glycerin were added as a stabilizer for the liquid dosage form to obtain a liquid dosage form product.

The 10% glycerin in the above liquid dosage form stabilizer was replaced with 3% lactose and 2% sodium sulfate, and other components remain unchanged, and a solid dosage form product was prepared by spray drying.

The above percentages (%) are all w/v.

Example 7: Application of Lactase in the Preparation of Galactooligosaccharides A lactose solution with a concentration of 600 g/L was used as a substrate, and the lactase BcBG168-D prepared by the invention was used to catalyze the preparation of galactooligosaccharides, and the total volume of the reaction system was about 30 L. The enzyme was added according to the substrate concentration of 20 U/g, the pH was adjusted to 6.0, the reaction system was stirred and reacted for 10 h in the reactor at 65° C. at a stirring speed of 50 r/min.

The content of galactooligosaccharides in the reaction product reached more than 50%. FIG. 6 is a typical result of the sugar profile analysis of the galactooligosaccharides produced above by the HPLC detection method.

The above-mentioned embodiments only express several implementation modes of the present invention, and the description is relatively specific and detailed, but it should not be understood as a limitation on the scope of the patent. It should be noted that for those of ordinary skill in the art, without departing from the concept of the patent, the above-mentioned embodiments can be modified, combined, and improved, which belong to the scope of protection of the patent. Therefore, the scope of protection of this patent should be subject to the claims.

What is claimed is:

1. A lactase consisting of SEQ ID NO: 4, 6, 10 or 12, or comprising SEQ ID NOS: 14, 16 or 18.

2. An encoding gene of the lactase of claim 1, wherein the encoding gene consists of SEQ ID NO: 3, 5, 9 or 11 or comprises SEQ ID NOS: 13, 15 or 17.

3. A recombinant vector, wherein said vector harbors any one of the encoding genes of claim 2.

4. The recombinant vector of claim 3, wherein, the recombinant vector is selected from the group consisting of: pHY-WZX, pBL-WZX, pHY300plk, pUB110, pE194, pHT1469, pWH1520, pHSE-001, pHSE-002, pHSE-003, pHSE-004, pHSE-005, pHSE-006, pHSE-007, pHSE-008, pHSE-009, pHSE-010, pHSE-011, pHSE-012, pHSE-013, pHSE-014, pHSE-015, pHSE-016, pHSE-017, and pHSE-018.

5. The recombinant vector of claim 3, comprising pHSE-018 wherein said vector comprises an amylase promoter $P_{amyL}$ derived from *Bacillus licheniformis* comprising SEQ ID NO: 20, and a signal peptide of alkaline protease aprE comprising SEQ ID NO: 23.

6. A recombinant host cell comprising the recombinant vector of claim 3, wherein, the recombinant host cell is selected from *Bacillus subtilis, Bacillus circulans, Bacillus megaterium, Bacillus pumilus, Bacillus amyloliquefaciens, Corynebacterium glutamicum,* or *Bacillus licheniformis.*

7. The recombinant host cell of claim 6, having knock-outs of the aprE, vpr, wpr, lack, lacA, lacA2, and yesZ genes.

8. The recombinant host cell of claim 7, wherein, the recombinant host cell is a *B. licheniformis.*

9. A method for fermentation and production of lactase by the recombinant host cell according to claim 6, comprising the steps of:
   performing a shaking flask fermentation to produce the lactase by inoculating the recombinant host cell to a shake flask culture medium, cultivating for 2 to 3 days at 30-45° C. and 120-270 r/min;
   wherein a composition of the shaking flask culture medium comprises yeast extract 0.5-1.5%, peptone 1.2-3.6%, glucose 8-20%; and a pH of the shaking flask culture medium is 7.0.

10. A method for fermentation and production of lactase by the recombinant host cell according to claim 6, comprising the steps of:
    inoculating the recombinant host cell to a fermentation tank culture medium according to an inoculum amount of 5%-10%, wherein a fermentation temperature is 33-45° C. during the fermentation;
    controlling dissolved oxygen at 0.1%-20%, pH at 6.0-7.8;
    adding 30%-60% maltose syrup and maintaining a reducing sugar content at 0.1%-5%;
    wherein the fermentation lasts for 90-120 h, an end of the fermentation is controlled so that an increased value of fermentation enzyme activity is less than 5-20 U/(mL-h);
    wherein the fermentation tank culture medium comprises: 1% to 5% of the maltose syrup, 0% to 5% of cottonseed powder, 0% to 5% of corn syrup, 0.5 to 5% of soybean meal powder, 0.1 to 5% of ammonium sulfate, and a pH of the fermentation tank culture medium is 6.0 to 8.0.

11. The method according to claim 9, wherein, after the fermentation is finished, the recombinant strain is removed by a plate and frame filtration, and then an enzyme solution is obtained after a filtration through an ultrafiltration system.

12. The method according to claim 10, wherein, after the fermentation is finished, the recombinant strain is removed by a plate and frame filtration, and then an enzyme solution is obtained after a filtration through an ultrafiltration system.

13. A method of producing lactase, comprising expressing any of the encoding genes of claim 2 from a recombinant vector or in a recombinant host cell.

14. A method of producing galactooligosaccharides, comprising the step of contacting lactose with the lactase of claim 1 to produce galactooligosaccharides.

15. A method of producing galactooligosaccharides, comprising the steps of expressing the genes claim 2 to produce the encoded lactases and contacting said lactases with lactose to produce galactooligosaccharides.

16. A recombinant host cell which harbors any one of the encoding genes of claim 2.

17. A recombinant vector comprising a gene encoding a lactase, wherein said gene comprises SEQ ID NO: 1, 3, 5, 7, 9, 11, 13, 15 or 17 and is operably linked to a heterologous promoter.

18. A recombinant host cell comprising the vector of claim 17.

* * * * *

SEQUENCE LISTING

<160> NUMBER OF SEQ ID NOS: 72

<210> SEQ ID NO 1
<211> LENGTH: 5133
<212> TYPE: DNA
<213> ORGANISM: B. circulans B2301

<400> SEQUENCE: 1

```
atgaaaagca cgacgagcgc cgccggcaaa agcgtcagct ataacgacgg cgaacgccgc      60
gtcaactttg aaaactggcg ctttcagcgc gaaacgaacg gcagcatcgc cggcgcccag     120
aacccgggct tgacgacag cagctggcgc aaactgaacc tgccgcatga atggagcatc     180
gacctggact taacaaaaa cagcctggcc acgcatgaag gcggctatct ggacggcggc     240
atcggctgga accgcaaaac gtttacgatc ccggaaagca tgaaaggcaa acgctttagc     300
ctggacatcg acggcgtcta tatgtatagc acgacgtatc tgaacgcctt tgtcctgggc     360
acgtatccgt ttggctataa cggcgaaagc tatgacatca gcgacaaact gtataaagac     420
ggccgcgcca acgtcctggt cgtcaaagtc aacacgaacc agccgagcgg ccgctggtat     480
agcggcagca gcatctatcg caacgtctat ctgacggtca cggacccgat ccatgtcgcc     540
cgctatggca cgtttgtcac gacgccgaac ctggaaaaaa gcatcaaaga agaccgcgac     600
gccgtcaaca tcaaaacgaa aatcagcaac gccgaagcca acaggtcaa aatcgccgac     660 aaaagcacga tctatgacgg cgccggcaac acggtccaga cggtcgaaac ggaagaaaaa     720
```

-continued

```
acggccgccg gcgccacggt cacgccgttt gaacagaaca cggtcatcaa acagccgaaa    780
ctgtggagca tcgacaaacc gtatcgctat aacctggtca cggaagtcat cgtcggcggc    840
cagacggtcg acacgtatga aacgaaattt ggcgtccgct attttaaatt tgacgaaaac    900
gaaggctata gcctgaacgg cgaatttatg aaactgcatg cgtcagcat gcatcatgac    960
ctggccggcg cgccgccct gacgaacgcc cgcggcgtcg aacgccagat gcagatcatg   1020
aaagacgtcg cgtcaacgc catccgcgtc acgcataacc cggccagccc ggaactgggc   1080
ctggaatttg ccgccaacaa actgctgatc atcgaagaag cctttgacag ctgggcccag   1140
agcaaaaaac cgtatgacta tggccgcttt tttaacgcct gggccgaaca tgacatcaaa   1200
gaaatggtcg accgcggcaa aaacgaaccg gccatcatca tgtggagcat cggcaacgaa   1260
atctatgaca cgacgaacgc cgccggcgtc gaaacggccc gcaacctggt cggctgggtc   1320
aaagaaatcg acacgacgcc gcgcgccacg atcggcgaag acaaaacgcg cggcgacaac   1380
gtcacgccga tcaacagcta tatcaaagaa atctttaaca tcgtcgacgt cgtcggcctg   1440
aactatagcg aaaacaacta tgacggctat cataaacaga acccgagctg gaaactgtat   1500
ggcagcgaaa cgagcagcgc cacgcgcagc cgcggcgtct atacgcagcc gtatcagtat   1560
aaccatgaca cgaaatatgc cgacctgcag cagagcagct atgacaacga ctatgtcggc   1620
tggggccgca cggcccagga cgcctggaaa tatgaccgcg acctgaaaca tatcgccggc   1680
cagtttatct ggacgggctt tgactatatc ggcgaaccga cgccgtatta aacagctat   1740
ccggccaaaa gcagctattt tggcgccgtc gacacggccg gctttccgaa agacatcttt   1800
tattattatc agagccagtg gaaaaaagaa ccgatggtcc atctgctgcc gcattggaac   1860
tggaaagaag cgaaaaagt ccgcgtcctg gcctatacga acgccagcaa agtcgaactg   1920
gtcctgaacg gcgaaagcct gggcaacgaa aaatatgaca caaacagac gagctggggc   1980
gccccgtata agaaacgaa agacggcaaa acgtatctgg aatgggccgt caaaccgctg   2040
aaaccgggca atttgacga agccgtcgcc gaaaacggca agtcatcgc ccgcgaccag   2100
gtcgtcacgg ccggcgaacc ggccagcgtc cgcctgacgg ccgaccgcaa agtcgtcaaa   2160
gccgacggca cggaccatag ctttatcacg gccgacatcg tcgacagcaa aggcatcgtc   2220
gtcccggacg ccgaccatct gatcacgttt aacgtcacgg ccagggcga actggccggc   2280
gtcgacaacg caacgccag cagcgtcgaa cgctataaag acaacaaacg caaagccttt   2340
agcggcaaag ccctggccat cgtccagagc agcaaactga gcggcaaaat cacggtccat   2400
gccagcgtcg ccggcctgag cagcgacagc acgagcgtct ttacggtcac gccggccgac   2460
catgacaaaa aaatcgtcgc cggcatcgac gacgtcaacc tgacggtcga cgtcaacgaa   2520
gccccgaaac tgccgagcga aatcaaagtc tattatagcg acgaaagcgc cgccgccaaa   2580
aacgtcacgt gggacgaagt cgacccgaaa cagtatagca cggtcggcga atttacggtc   2640
gaaggcagcg tcgaaggcac gagcctgaaa gccaaagcct ttgtcatcgt caaaggcatc   2700
gtcgccgtca accgtatag cacggccacg aaagtcggcg tccagccggt cctgccggaa   2760
aaagccacgc tgctgtatag cgacggcacg acgaaaggcg ccacggtcac gtgggacgaa   2820
ctgccggaag acaaactggc caagaaggc cgctttacgg tcgaaggcag cgtcgaaggc   2880
acggacctga agccaacgt ctatgtccgc gtcacgaacg aagtcaaaag cgtcaacatc   2940
atgctgcaga acagggcag cgcctatccg aaactggaag ccacgtttac gaacccggcc   3000
gacaacctgc agcatctgaa cgacggcatc aaaagctata cgaacaacca ggtcaaccgc   3060
```

```
tggacgaact ggacgcgcac gccgcgcgac gccggcgaca gcatcacggt caactttggc    3120
aaaaaacatg tcatcaacaa cctggacctg tttgtcttta cggacagcgg cacggtcgtc    3180
ccggaaaaag ccgaagtcca gtattgggac ggcacggccg tcaaagacgt cgaaaacctg    3240
acgcagccga gcccgtatgt cgtcgaaaaa acgaactga cgtttgacgc cgtcgccacg    3300
gaaaaactga atttcatct gacgccgagc gtcaaaggca atttctggc cctgacggaa     3360
gccgaagtct atgccgacca gatcgtcgac ggcgaaacgg ccaaactgca gagcatcacg    3420
gtcaacggca aagccctgga aggctttgac catgccaaaa aaaactatga actggtcctg    3480
ccgtatggca cgaactgcc gaaaatcgaa gccgccgccg ccgacaacgc cacggtcacg     3540
atcctgccgg cctttagcta tccgggcacg gccaaactgt ttgtcacgag cgaagacggc    3600
aaagtcacga cggaatatag catcggcgtc agcacggaag aaccgaaact ggtcagcgcc    3660
gaactgagcg ccgacaaaac gaacgtcatg gaagacgaca tcatcgacct gaaagtcatc    3720
ggcctgtttg aaagcaaaga aaaaatcgac gtcacggaca gccagccgac gtatgaattt    3780
gaccagcaga tcatcaaaat cgaaggcaac aaactgtatg ccctggaaac gggcaacgtc    3840
aaagtcaaag tcacggtcac gtataaaggc gtcagcgtca cgacgccggc cctggaattt    3900
acgatcgcca acatccggc cccgaaatat atcacgagcc tggaaccggt cacggtcgtc    3960
gtcaaaaaag gcgaagcccc ggaactgccg gccacggtcg tcgcccatta taaccgcggc    4020
atcccgcgcg acgtcaaagt caaatgggaa cgcatccatc cgagcaaata tcagcagctg    4080
ggcgaattta cggtcagcgg catggtcgaa ggcacggaca tcaaagccca ggccaaagtc    4140
gccgtcaaag gcgccgtcat cgtcgaagac atccgcatgg ccgtcctgct gaaacagatg    4200
ccgcagctgc cgggcaaagt cacggtctat tatagcgacg cgccgaaga cagcgcgcc     4260
gtcaaatggg aagaaatccc gcaggaagaa ctggaaaag tcggcgaatt taaagtcaac    4320
ggcgacgtca acggcgtcaa actgaaagcc acggccacga tccgcgtcac ggacgaagtc    4380
ggcgccgaac agaacatcag ccgcgccaaa acggctatg aatatccgaa agccgaagcc     4440
agctttacga acgacggccc gggcagcagc gaccgcatcg aagccatcaa cgacgacgtc    4500
atcagctatg aagccaaccc gcataaccgc tggacgaact ggcagccggc cccgcgcgtc    4560
ggcgacctgg tctttacgac gtttggcgac tatgaaccga cggaatatga cgtcgacagc    4620
atggaaatcc attggtttgc cgaccatggc acgagctatc cggaacgctt tcagatcgaa    4680
tataaaagcg gcgacagctg gaaagaagtc acgagcctga aaagcgaccc ggccagcccg    4740
gccctgggca aagccaacgt ctatagcttt gaccgcgtca aaacgagcgc catccgcgtc    4800
aaaatgacgg cccaggccgg caaaagcctg gccatcacgg aactgaaagt ctttagcaaa    4860
tggccgaaag ccggcacgga accggacgtc acggacatca agtcggcgg caaaagcatc    4920
ctggaagaat ttgaacagga aggcgaccat tatgaagcca cgatcgacgt cggcgacgcc    4980
aacgtcatgc cgaaaatcta tgtcaaagcc aaagaccaga cgagcatcag catcgtcccg    5040
gccgtcacga gcgtcagcac ggccaaagtc atcgccgaag acggcgacgg caaaaaagtc    5100
aaagtctata gcatccataa aagctataaa taa                                5133
```

<210> SEQ ID NO 2
<211> LENGTH: 1710
<212> TYPE: PRT
<213> ORGANISM: B. circulans B2301

<400> SEQUENCE: 2

Met Lys Ser Thr Thr Ser Ala Ala Gly Lys Ser Val Ser Tyr Asn Asp

```
  1               5                  10                  15
Gly Glu Arg Arg Val Asn Phe Glu Asn Trp Arg Phe Gln Arg Glu Thr
                 20                  25                  30

Asn Gly Ser Ile Ala Gly Ala Gln Asn Pro Gly Phe Asp Asp Ser Ser
                 35                  40                  45

Trp Arg Lys Leu Asn Leu Pro His Glu Trp Ser Ile Asp Leu Asp Phe
 50                  55                  60

Asn Lys Asn Ser Leu Ala Thr His Glu Gly Gly Tyr Leu Asp Gly Gly
 65                  70                  75                  80

Ile Gly Trp Asn Arg Lys Thr Phe Thr Ile Pro Glu Ser Met Lys Gly
                 85                  90                  95

Lys Arg Phe Ser Leu Asp Ile Asp Gly Val Tyr Met Tyr Ser Thr Thr
                 100                 105                 110

Tyr Leu Asn Ala Phe Val Leu Gly Thr Tyr Pro Phe Gly Tyr Asn Gly
                 115                 120                 125

Glu Ser Tyr Asp Ile Ser Asp Lys Leu Tyr Lys Asp Gly Arg Ala Asn
         130                 135                 140

Val Leu Val Val Lys Val Asn Thr Asn Gln Pro Ser Gly Arg Trp Tyr
145                 150                 155                 160

Ser Gly Ser Ser Ile Tyr Arg Asn Val Tyr Leu Thr Val Thr Asp Pro
                 165                 170                 175

Ile His Val Ala Arg Tyr Gly Thr Phe Val Thr Thr Pro Asn Leu Glu
                 180                 185                 190

Lys Ser Ile Lys Glu Asp Arg Asp Ala Val Asn Ile Lys Thr Lys Ile
                 195                 200                 205

Ser Asn Ala Glu Ala Lys Gln Val Lys Ile Ala Asp Lys Ser Thr Ile
         210                 215                 220

Tyr Asp Gly Ala Gly Asn Thr Val Gln Thr Val Glu Thr Glu Glu Lys
225                 230                 235                 240

Thr Ala Ala Gly Ala Thr Val Thr Pro Phe Glu Gln Asn Thr Val Ile
                 245                 250                 255

Lys Gln Pro Lys Leu Trp Ser Ile Asp Lys Pro Tyr Arg Tyr Asn Leu
                 260                 265                 270

Val Thr Glu Val Ile Val Gly Gly Gln Thr Val Asp Thr Tyr Glu Thr
                 275                 280                 285

Lys Phe Gly Val Arg Tyr Phe Lys Phe Asp Glu Asn Glu Gly Tyr Ser
                 290                 295                 300

Leu Asn Gly Glu Phe Met Lys Leu His Gly Val Ser Met His His Asp
305                 310                 315                 320

Leu Ala Gly Gly Ala Ala Leu Thr Asn Ala Arg Gly Val Glu Arg Gln
                 325                 330                 335

Met Gln Ile Met Lys Asp Val Gly Val Asn Ala Ile Arg Val Thr His
                 340                 345                 350

Asn Pro Ala Ser Pro Glu Leu Gly Leu Glu Phe Ala Ala Asn Lys Leu
                 355                 360                 365

Leu Ile Ile Glu Glu Ala Phe Asp Ser Trp Ala Gln Ser Lys Lys Pro
                 370                 375                 380

Tyr Asp Tyr Gly Arg Phe Phe Asn Ala Trp Ala Glu His Asp Ile Lys
385                 390                 395                 400

Glu Met Val Asp Arg Gly Lys Asn Glu Pro Ala Ile Ile Met Trp Ser
                 405                 410                 415

Ile Gly Asn Glu Ile Tyr Asp Thr Thr Asn Ala Ala Gly Val Glu Thr
                 420                 425                 430
```

```
Ala Arg Asn Leu Val Gly Trp Val Lys Glu Ile Asp Thr Thr Pro Arg
            435                 440                 445

Ala Thr Ile Gly Glu Asp Lys Thr Arg Gly Asp Asn Val Thr Pro Ile
        450                 455                 460

Asn Ser Tyr Ile Lys Glu Ile Phe Asn Ile Val Asp Val Val Gly Leu
465                 470                 475                 480

Asn Tyr Ser Glu Asn Asn Tyr Asp Gly Tyr His Lys Gln Asn Pro Ser
                485                 490                 495

Trp Lys Leu Tyr Gly Ser Glu Thr Ser Ser Ala Thr Arg Ser Arg Gly
            500                 505                 510

Val Tyr Thr Gln Pro Tyr Gln Tyr Asn His Asp Thr Lys Tyr Ala Asp
        515                 520                 525

Leu Gln Gln Ser Ser Tyr Asp Asn Asp Tyr Val Gly Trp Gly Arg Thr
530                 535                 540

Ala Gln Asp Ala Trp Lys Tyr Asp Arg Asp Leu Lys His Ile Ala Gly
545                 550                 555                 560

Gln Phe Ile Trp Thr Gly Phe Asp Tyr Ile Gly Glu Pro Thr Pro Tyr
                565                 570                 575

Tyr Asn Ser Tyr Pro Ala Lys Ser Ser Tyr Phe Gly Ala Val Asp Thr
            580                 585                 590

Ala Gly Phe Pro Lys Asp Ile Phe Tyr Tyr Gln Ser Gln Trp Lys
        595                 600                 605

Lys Glu Pro Met Val His Leu Leu Pro His Trp Asn Trp Lys Glu Gly
610                 615                 620

Glu Lys Val Arg Val Leu Ala Tyr Thr Asn Ala Ser Lys Val Glu Leu
625                 630                 635                 640

Val Leu Asn Gly Glu Ser Leu Gly Asn Glu Lys Tyr Asp Asn Lys Gln
                645                 650                 655

Thr Ser Trp Gly Ala Pro Tyr Lys Glu Thr Lys Asp Gly Lys Thr Tyr
            660                 665                 670

Leu Glu Trp Ala Val Lys Pro Leu Lys Pro Gly Lys Phe Asp Glu Ala
        675                 680                 685

Val Ala Glu Asn Gly Lys Val Ile Ala Arg Asp Gln Val Val Thr Ala
    690                 695                 700

Gly Glu Pro Ala Ser Val Arg Leu Thr Ala Asp Arg Lys Val Val Lys
705                 710                 715                 720

Ala Asp Gly Thr Asp His Ser Phe Ile Thr Ala Asp Ile Val Asp Ser
                725                 730                 735

Lys Gly Ile Val Val Pro Asp Ala Asp His Leu Ile Thr Phe Asn Val
            740                 745                 750

Thr Gly Gln Gly Glu Leu Ala Gly Val Asp Asn Gly Asn Ala Ser Ser
        755                 760                 765

Val Glu Arg Tyr Lys Asp Asn Lys Arg Lys Ala Phe Ser Gly Lys Ala
    770                 775                 780

Leu Ala Ile Val Gln Ser Ser Lys Leu Ser Gly Lys Ile Thr Val His
785                 790                 795                 800

Ala Ser Val Ala Gly Leu Ser Ser Asp Ser Thr Ser Val Phe Thr Val
                805                 810                 815

Thr Pro Ala Asp His Asp Lys Lys Ile Val Ala Gly Ile Asp Asp Val
            820                 825                 830

Asn Leu Thr Val Asp Val Asn Glu Ala Pro Lys Leu Pro Ser Glu Ile
        835                 840                 845
```

-continued

```
Lys Val Tyr Tyr Ser Asp Glu Ser Ala Ala Ala Lys Asn Val Thr Trp
850                 855                 860

Asp Glu Val Asp Pro Lys Gln Tyr Ser Thr Val Gly Glu Phe Thr Val
865                 870                 875                 880

Glu Gly Ser Val Glu Gly Thr Ser Leu Lys Ala Lys Ala Phe Val Ile
            885                 890                 895

Val Lys Gly Ile Val Ala Val Lys Pro Tyr Ser Thr Ala Thr Lys Val
                900                 905                 910

Gly Val Gln Pro Val Leu Pro Glu Lys Ala Thr Leu Leu Tyr Ser Asp
            915                 920                 925

Gly Thr Thr Lys Gly Ala Thr Val Thr Trp Asp Glu Leu Pro Glu Asp
930                 935                 940

Lys Leu Ala Lys Glu Gly Arg Phe Thr Val Glu Gly Ser Val Glu Gly
945                 950                 955                 960

Thr Asp Leu Lys Ala Asn Val Tyr Val Arg Val Thr Asn Glu Val Lys
            965                 970                 975

Ser Val Asn Ile Met Leu Gln Glu Gln Gly Ser Ala Tyr Pro Lys Leu
            980                 985                 990

Glu Ala Thr Phe Thr Asn Pro Ala Asp Asn Leu Gln His Leu Asn Asp
            995                 1000                1005

Gly Ile Lys Ser Tyr Thr Asn Asn Gln Val Asn Arg Trp Thr Asn
    1010                1015                1020

Trp Thr Arg Thr Pro Arg Asp Ala Gly Asp Ser Ile Thr Val Asn
    1025                1030                1035

Phe Gly Lys Lys His Val Ile Asn Asn Leu Asp Leu Phe Val Phe
    1040                1045                1050

Thr Asp Ser Gly Thr Val Val Pro Glu Lys Ala Glu Val Gln Tyr
    1055                1060                1065

Trp Asp Gly Thr Ala Val Lys Asp Val Glu Asn Leu Thr Gln Pro
    1070                1075                1080

Ser Pro Tyr Val Val Glu Lys Asn Glu Leu Thr Phe Asp Ala Val
    1085                1090                1095

Ala Thr Glu Lys Leu Lys Phe His Leu Thr Pro Ser Val Lys Gly
    1100                1105                1110

Lys Phe Leu Ala Leu Thr Glu Ala Glu Val Tyr Ala Asp Gln Ile
    1115                1120                1125

Val Asp Gly Glu Thr Ala Lys Leu Gln Ser Ile Thr Val Asn Gly
    1130                1135                1140

Lys Ala Leu Glu Gly Phe Asp His Ala Lys Lys Asn Tyr Glu Leu
    1145                1150                1155

Val Leu Pro Tyr Gly Ser Glu Leu Pro Lys Ile Glu Ala Ala Ala
    1160                1165                1170

Ala Asp Asn Ala Thr Val Thr Ile Leu Pro Ala Phe Ser Tyr Pro
    1175                1180                1185

Gly Thr Ala Lys Leu Phe Val Thr Ser Glu Asp Gly Lys Val Thr
    1190                1195                1200

Thr Glu Tyr Ser Ile Gly Val Ser Thr Glu Glu Pro Lys Leu Val
    1205                1210                1215

Ser Ala Glu Leu Ser Ala Asp Lys Thr Asn Val Met Glu Asp Asp
    1220                1225                1230

Ile Ile Asp Leu Lys Val Ile Gly Leu Phe Glu Ser Lys Glu Lys
    1235                1240                1245

Ile Asp Val Thr Asp Ser Gln Pro Thr Tyr Glu Phe Asp Gln Gln
```

```
                1250                1255                1260
Ile Ile Lys Ile Glu Gly Asn Lys Leu Tyr Ala Leu Glu Thr Gly
                1265                1270                1275
Asn Val Lys Val Lys Val Thr Val Thr Tyr Lys Gly Val Ser Val
                1280                1285                1290
Thr Thr Pro Ala Leu Glu Phe Thr Ile Ala Lys His Pro Ala Pro
                1295                1300                1305
Lys Tyr Ile Thr Ser Leu Glu Pro Val Thr Val Val Lys Lys
                1310                1315                1320
Gly Glu Ala Pro Glu Leu Pro Ala Thr Val Val Ala His Tyr Asn
                1325                1330                1335
Arg Gly Ile Pro Arg Asp Val Lys Val Lys Trp Glu Arg Ile His
                1340                1345                1350
Pro Ser Lys Tyr Gln Gln Leu Gly Glu Phe Thr Val Ser Gly Met
                1355                1360                1365
Val Glu Gly Thr Asp Ile Lys Ala Gln Ala Lys Val Ala Val Lys
                1370                1375                1380
Gly Ala Val Ile Val Glu Asp Ile Arg Met Ala Val Leu Leu Lys
                1385                1390                1395
Gln Met Pro Gln Leu Pro Gly Lys Val Thr Val Tyr Tyr Ser Asp
                1400                1405                1410
Gly Ala Glu Glu Gln Arg Ala Val Lys Trp Glu Ile Pro Gln
                1415                1420                1425
Glu Glu Leu Glu Lys Val Gly Glu Phe Lys Val Asn Gly Asp Val
                1430                1435                1440
Asn Gly Val Lys Leu Lys Ala Thr Ala Thr Ile Arg Val Thr Asp
                1445                1450                1455
Glu Val Gly Ala Glu Gln Asn Ile Ser Arg Ala Lys Asn Gly Tyr
                1460                1465                1470
Glu Tyr Pro Lys Ala Glu Ala Ser Phe Thr Asn Asp Gly Pro Gly
                1475                1480                1485
Ser Ser Asp Arg Ile Glu Ala Ile Asn Asp Val Ile Ser Tyr
                1490                1495                1500
Glu Ala Asn Pro His Asn Arg Trp Thr Asn Trp Gln Pro Ala Pro
                1505                1510                1515
Arg Val Gly Asp Leu Val Phe Thr Thr Phe Gly Asp Tyr Glu Pro
                1520                1525                1530
Thr Glu Tyr Asp Val Asp Ser Met Glu Ile His Trp Phe Ala Asp
                1535                1540                1545
His Gly Thr Ser Tyr Pro Glu Arg Phe Gln Ile Glu Tyr Lys Ser
                1550                1555                1560
Gly Asp Ser Trp Lys Glu Val Thr Ser Leu Lys Ser Asp Pro Ala
                1565                1570                1575
Ser Pro Ala Leu Gly Lys Ala Asn Val Tyr Ser Phe Asp Arg Val
                1580                1585                1590
Lys Thr Ser Ala Ile Arg Val Lys Met Thr Ala Gln Ala Gly Lys
                1595                1600                1605
Ser Leu Ala Ile Thr Glu Leu Lys Val Phe Ser Lys Trp Pro Lys
                1610                1615                1620
Ala Gly Thr Glu Pro Asp Val Thr Asp Ile Lys Val Gly Gly Lys
                1625                1630                1635
Ser Ile Leu Glu Glu Phe Glu Gln Glu Gly Asp His Tyr Glu Ala
                1640                1645                1650
```

```
Thr Ile Asp Val Gly Asp Ala Asn Val Met Pro Lys Ile Tyr Val
    1655                1660                1665

Lys Ala Lys Asp Gln Thr Ser Ile Ser Ile Val Pro Ala Val Thr
    1670                1675                1680

Ser Val Ser Thr Ala Lys Val Ile Ala Glu Asp Gly Asp Gly Lys
    1685                1690                1695

Lys Val Lys Val Tyr Ser Ile His Lys Ser Tyr Lys
    1700                1705                1710

<210> SEQ ID NO 3
<211> LENGTH: 3672
<212> TYPE: DNA
<213> ORGANISM: Artificial sequence
<220> FEATURE:
<223> OTHER INFORMATION: The sequence is synthesized

<400> SEQUENCE: 3
```

| | | | | | |
|---|---|---|---|---|---|
| atgaaaagca | cgacgagcgc | cgccggcaaa | agcgtcagct | ataacgacgg | cgaacgccgc | 60 |
| gtcaactttg | aaaactggcg | ctttcagcgc | gaaacgaacg | gcagcatcgc | cggcgcccag | 120 |
| aacccgggct | ttgacgacag | cagctggcgc | aaactgaacc | tgccgcatga | atggagcatc | 180 |
| gacctggact | taaacaaaaa | cagcctggcc | acgcatgaag | gcggctatct | ggacggcggc | 240 |
| atcggctgga | accgcaaaac | gtttacgatc | ccggaaagca | tgaaaggcaa | acgctttagc | 300 |
| ctggacatcg | acggcgtcta | tgtatagc | acgacgtatc | tgaacgcctt | tgtcctgggc | 360 |
| acgtatccgt | ttggctataa | cggcgaaagc | tatgacatca | gcgacaaact | gtataaagac | 420 |
| ggccgcgcca | acgtcctggt | cgtcaaagtc | aacacgaacc | agccgagcgg | ccgctggtat | 480 |
| agcggcagca | gcatctatcg | caacgtctat | ctgacggtca | cggacccgat | ccatgtcgcc | 540 |
| cgctatggca | cgtttgtcac | gacgccgaac | ctggaaaaaa | gcatcaaaga | agaccgcgac | 600 |
| gccgtcaaca | tcaaaacgaa | aatcagcaac | gccgaagcca | acaggtcaa | aatcgccgac | 660 |
| aaaagcacga | tctatgacgg | cgccggcaac | acggtccaga | cggtcgaaac | ggaagaaaaa | 720 |
| acggccgccg | cgccacggt | cacgccgttt | gaacagaaca | cggtcatcaa | acagccgaaa | 780 |
| ctgtggagca | tcgacaaacc | gtatcgctat | aacctggtca | cggaagtcat | cgtcggcggc | 840 |
| cagacggtcg | acacgtatga | aacgaaattt | ggcgtccgct | attttaaatt | tgacgaaaac | 900 |
| gaaggctata | gcctgaacgg | cgaatttatg | aaactgcatg | gcgtcagcat | gcatcatgac | 960 |
| ctggccggcg | cgccgcccct | gacgaacgcc | cgcggcgtcg | aacgccagat | gcagatcatg | 1020 |
| aaagacgtcg | cgtcaacgc | catccgcgtc | acgcataacc | cggccagccc | ggaactgggc | 1080 |
| ctggaatttg | ccgccaacaa | actgctgatc | atcgaagaag | cctttgacag | ctgggcccag | 1140 |
| agcaaaaaac | cgtatgacta | tggccgcttt | tttaacgcct | gggccgaaca | tgacatcaaa | 1200 |
| gaaatggtcg | accgcggcaa | aaacgaaccg | gccatcatca | tgtggagcat | cggcaacgaa | 1260 |
| atctatgaca | cgacgaacgc | cgccggcgtc | gaaacggccc | gcaacctggt | cggctgggtc | 1320 |
| aaagaaatcg | acacgacgcc | gcgcgccacg | atcggcgaag | acaaaacgcg | cggcgacaac | 1380 |
| gtcacgccga | tcaacagcta | tatcaaagaa | atctttaaca | tcgtcgacgt | cgtcggcctg | 1440 |
| aactatagcg | aaaacaacta | tgacggctat | cataaacaga | acccgagctg | aaactgtat | 1500 |
| ggcagcgaaa | cgagcagcgc | cacgcgcagc | cgcggcgtct | atacgcagcc | gtatcagtat | 1560 |
| aaccatgaca | cgaaatatgc | cgacctgcag | cagagcagct | atgacaacga | ctatgtcggc | 1620 |
| tggggccgca | cggcccagga | cgcctggaaa | tatgaccgcg | acctgaaaca | tatcgccggc | 1680 |

| | |
|---|---|
| cagtttatct ggacgggctt tgactatatc ggcgaaccga cgccgtatta taacagctat | 1740 |
| ccggccaaaa gcagctattt tggcgccgtc gacacggccg gctttccgaa agacatcttt | 1800 |
| tattattatc agagccagtg aaaaaagaa ccgatggtcc atctgctgcc gcattggaac | 1860 |
| tggaaagaag cgaaaaagt ccgcgtcctg gcctatacga acgccagcaa agtcgaactg | 1920 |
| gtcctgaacg gcgaaagcct gggcaacgaa aaatatgaca caaacagac gagctgggc | 1980 |
| gccccgtata agaaacgaa agacggcaaa acgtatctgg aatgggccgt caaaccgctg | 2040 |
| aaaccgggca aatttgacga agccgtcgcc gaaaacggca agtcatcgc ccgcgaccag | 2100 |
| gtcgtcacgg ccggcgaacc ggccagcgtc cgcctgacgg ccgaccgcaa agtcgtcaaa | 2160 |
| gccgacggca cggaccatag ctttatcacg gccgacatcg tcgacagcaa aggcatcgtc | 2220 |
| gtcccgacg ccgaccatct gatcacgttt aacgtcacgg gccagggcga actggccggc | 2280 |
| gtcgacaacg gcaacgccag cagcgtcgaa cgctataaag acaacaaacg caaagccttt | 2340 |
| agcggcaaag ccctggccat cgtccagagc agcaaactga gcggcaaaat cacggtccat | 2400 |
| gccagcgtcg ccgcctgag cagcgacagc acgagcgtct ttacggtcac gccggccgac | 2460 |
| catgacaaaa aaatcgtcgc cggcatcgac gacgtcaacc tgacggtcga cgtcaacgaa | 2520 |
| gccccgaaac tgccgagcga aatcaaagtc tattatagcg acgaaagcgc cgccgccaaa | 2580 |
| aacgtcacgt gggacgaagt cgaccccgaaa cagtatagca cggtcggcga atttacggtc | 2640 |
| gaaggcagcg tcgaaggcac gagcctgaaa gccaaagcct ttgtcatcgt caaaggcatc | 2700 |
| gtcgccgtca accgtatag cacggccacg aaagtcggcg tccagccggt cctgccggaa | 2760 |
| aaagccacgc tgctgtatag cgacggcacg acgaaaggcg ccacggtcac gtgggacgaa | 2820 |
| ctgccggaag acaaactggc caaagaaggc cgctttacgg tcgaaggcag cgtcgaaggc | 2880 |
| acggacctga agccaacgt ctatgtccgc gtcacgaacg aagtcaaaag cgtcaacatc | 2940 |
| atgctgcagg aacagggcag cgcctatccg aaactggaag ccacgtttac gaacccggcc | 3000 |
| gacaacctgc agcatctgaa cgacggcatc aaaagctata cgaacaacca ggtcaaccgc | 3060 |
| tggacgaact ggacgcgcac gccgcgcgac gccggcgaca gcatcacggt caactttggc | 3120 |
| aaaaaacatg tcatcaacaa cctggacctg tttgtcttta cggacagcgg cacggtcgtc | 3180 |
| ccggaaaaag ccgaagtcca gtattgggac ggcacggccg tcaaagacgt cgaaaacctg | 3240 |
| acgcagccga gccgtatgt cgtcgaaaaa aacgaactga cgtttgacgc cgtcgccacg | 3300 |
| gaaaaactga atttcatct gacgccgagc gtcaaggca aatttctggc cctgacggaa | 3360 |
| gccgaagtct atgccgacca gatcgtcgac ggcgaaacgg ccaaactgca gagcatcacg | 3420 |
| gtcaacggca agcccctgga aggctttgac catgccaaaa aaactatga actggtcctg | 3480 |
| ccgtatggca cgaactgcc gaaaatcgaa gccgccgccg ccgacaacgc cacggtcacg | 3540 |
| atcctgccgg cctttagcta tccgggcacg gccaaactgt tgtcacgag cgaagacggc | 3600 |
| aaagtcacga cggaatatag catcggcgtc agcacggaag aaccgaaact ggtcagcgcc | 3660 |
| gaactgagct aa | 3672 |

<210> SEQ ID NO 4
<211> LENGTH: 1223
<212> TYPE: PRT
<213> ORGANISM: Artificial sequence
<220> FEATURE:
<223> OTHER INFORMATION: The sequence is synthesized

<400> SEQUENCE: 4

Met Lys Ser Thr Thr Ser Ala Ala Gly Lys Ser Val Ser Tyr Asn Asp

-continued

```
  1               5                  10                 15
Gly Glu Arg Arg Val Asn Phe Glu Asn Trp Arg Phe Gln Arg Glu Thr
                 20                 25                 30
Asn Gly Ser Ile Ala Gly Ala Gln Asn Pro Gly Phe Asp Asp Ser Ser
                 35                 40                 45
Trp Arg Lys Leu Asn Leu Pro His Glu Trp Ser Ile Asp Leu Asp Phe
         50                 55                 60
Asn Lys Asn Ser Leu Ala Thr His Glu Gly Tyr Leu Asp Gly Gly
 65              70                 75                 80
Ile Gly Trp Asn Arg Lys Thr Phe Thr Ile Pro Glu Ser Met Lys Gly
                 85                 90                 95
Lys Arg Phe Ser Leu Asp Ile Asp Gly Val Tyr Met Tyr Ser Thr Thr
                100                105                110
Tyr Leu Asn Ala Phe Val Leu Gly Thr Tyr Pro Phe Gly Tyr Asn Gly
                115                120                125
Glu Ser Tyr Asp Ile Ser Asp Lys Leu Tyr Lys Asp Gly Arg Ala Asn
                130                135                140
Val Leu Val Val Lys Val Asn Thr Asn Gln Pro Ser Gly Arg Trp Tyr
145                150                155                160
Ser Gly Ser Ser Ile Tyr Arg Asn Val Tyr Leu Thr Val Thr Asp Pro
                165                170                175
Ile His Val Ala Arg Tyr Gly Thr Phe Val Thr Thr Pro Asn Leu Glu
                180                185                190
Lys Ser Ile Lys Glu Asp Arg Asp Ala Val Asn Ile Lys Thr Lys Ile
                195                200                205
Ser Asn Ala Glu Ala Lys Gln Val Lys Ile Ala Asp Lys Ser Thr Ile
                210                215                220
Tyr Asp Gly Ala Gly Asn Thr Val Gln Thr Val Glu Thr Glu Glu Lys
225                230                235                240
Thr Ala Ala Gly Ala Thr Val Thr Pro Phe Glu Gln Asn Thr Val Ile
                245                250                255
Lys Gln Pro Lys Leu Trp Ser Ile Asp Lys Pro Tyr Arg Tyr Asn Leu
                260                265                270
Val Thr Glu Val Ile Val Gly Gly Gln Thr Val Asp Thr Tyr Glu Thr
                275                280                285
Lys Phe Gly Val Arg Tyr Phe Lys Phe Asp Glu Asn Glu Gly Tyr Ser
                290                295                300
Leu Asn Gly Glu Phe Met Lys Leu His Gly Val Ser Met His His Asp
305                310                315                320
Leu Ala Gly Gly Ala Ala Leu Thr Asn Ala Arg Gly Val Glu Arg Gln
                325                330                335
Met Gln Ile Met Lys Asp Val Gly Val Asn Ala Ile Arg Val Thr His
                340                345                350
Asn Pro Ala Ser Pro Glu Leu Gly Leu Glu Phe Ala Ala Asn Lys Leu
                355                360                365
Leu Ile Ile Glu Glu Ala Phe Asp Ser Trp Ala Gln Ser Lys Lys Pro
                370                375                380
Tyr Asp Tyr Gly Arg Phe Phe Asn Ala Trp Ala Glu His Asp Ile Lys
385                390                395                400
Glu Met Val Asp Arg Gly Lys Asn Glu Pro Ala Ile Ile Met Trp Ser
                405                410                415
Ile Gly Asn Glu Ile Tyr Asp Thr Thr Asn Ala Ala Gly Val Glu Thr
                420                425                430
```

```
Ala Arg Asn Leu Val Gly Trp Val Lys Glu Ile Asp Thr Thr Pro Arg
        435                 440                 445

Ala Thr Ile Gly Glu Asp Lys Thr Arg Gly Asp Asn Val Thr Pro Ile
450                 455                 460

Asn Ser Tyr Ile Lys Glu Ile Phe Asn Ile Val Asp Val Val Gly Leu
465                 470                 475                 480

Asn Tyr Ser Glu Asn Asn Tyr Asp Gly Tyr His Lys Gln Asn Pro Ser
                485                 490                 495

Trp Lys Leu Tyr Gly Ser Glu Thr Ser Ser Ala Thr Arg Ser Arg Gly
                500                 505                 510

Val Tyr Thr Gln Pro Tyr Gln Tyr Asn His Asp Thr Lys Tyr Ala Asp
        515                 520                 525

Leu Gln Gln Ser Ser Tyr Asp Asn Asp Tyr Val Gly Trp Gly Arg Thr
        530                 535                 540

Ala Gln Asp Ala Trp Lys Tyr Asp Arg Asp Leu Lys His Ile Ala Gly
545                 550                 555                 560

Gln Phe Ile Trp Thr Gly Phe Asp Tyr Ile Gly Glu Pro Thr Pro Tyr
                565                 570                 575

Tyr Asn Ser Tyr Pro Ala Lys Ser Ser Tyr Phe Gly Ala Val Asp Thr
                580                 585                 590

Ala Gly Phe Pro Lys Asp Ile Phe Tyr Tyr Gln Ser Gln Trp Lys
        595                 600                 605

Lys Glu Pro Met Val His Leu Leu Pro His Trp Asn Trp Lys Glu Gly
        610                 615                 620

Glu Lys Val Arg Val Leu Ala Tyr Thr Asn Ala Ser Lys Val Glu Leu
625                 630                 635                 640

Val Leu Asn Gly Glu Ser Leu Gly Asn Glu Lys Tyr Asp Asn Lys Gln
                645                 650                 655

Thr Ser Trp Gly Ala Pro Tyr Lys Glu Thr Lys Asp Gly Lys Thr Tyr
                660                 665                 670

Leu Glu Trp Ala Val Lys Pro Leu Lys Pro Gly Lys Phe Asp Glu Ala
        675                 680                 685

Val Ala Glu Asn Gly Lys Val Ile Ala Arg Asp Gln Val Val Thr Ala
        690                 695                 700

Gly Glu Pro Ala Ser Val Arg Leu Thr Ala Asp Arg Lys Val Val Lys
705                 710                 715                 720

Ala Asp Gly Thr Asp His Ser Phe Ile Thr Ala Asp Ile Val Asp Ser
                725                 730                 735

Lys Gly Ile Val Val Pro Asp Ala Asp His Leu Ile Thr Phe Asn Val
                740                 745                 750

Thr Gly Gln Gly Glu Leu Ala Gly Val Asp Asn Gly Asn Ala Ser Ser
        755                 760                 765

Val Glu Arg Tyr Lys Asp Asn Lys Arg Lys Ala Phe Ser Gly Lys Ala
        770                 775                 780

Leu Ala Ile Val Gln Ser Ser Lys Leu Ser Gly Lys Ile Thr Val His
785                 790                 795                 800

Ala Ser Val Ala Gly Leu Ser Ser Asp Ser Thr Ser Val Phe Thr Val
                805                 810                 815

Thr Pro Ala Asp His Asp Lys Lys Ile Val Ala Gly Ile Asp Asp Val
                820                 825                 830

Asn Leu Thr Val Asp Val Asn Glu Ala Pro Lys Leu Pro Ser Glu Ile
        835                 840                 845
```

```
Lys Val Tyr Tyr Ser Asp Glu Ser Ala Ala Lys Asn Val Thr Trp
    850                 855                 860
Asp Glu Val Asp Pro Lys Gln Tyr Ser Thr Val Gly Glu Phe Thr Val
865                 870                 875                 880
Glu Gly Ser Val Glu Gly Thr Ser Leu Lys Ala Lys Ala Phe Val Ile
                885                 890                 895
Val Lys Gly Ile Val Ala Val Lys Pro Tyr Ser Thr Ala Thr Lys Val
            900                 905                 910
Gly Val Gln Pro Val Leu Pro Glu Lys Ala Thr Leu Leu Tyr Ser Asp
        915                 920                 925
Gly Thr Thr Lys Gly Ala Thr Val Thr Trp Asp Glu Leu Pro Glu Asp
    930                 935                 940
Lys Leu Ala Lys Glu Gly Arg Phe Thr Val Glu Gly Ser Val Glu Gly
945                 950                 955                 960
Thr Asp Leu Lys Ala Asn Val Tyr Val Arg Val Thr Asn Glu Val Lys
                965                 970                 975
Ser Val Asn Ile Met Leu Gln Glu Gln Gly Ser Ala Tyr Pro Lys Leu
            980                 985                 990
Glu Ala Thr Phe Thr Asn Pro Ala Asp Asn Leu Gln His Leu Asn Asp
        995                 1000                1005
Gly Ile Lys Ser Tyr Thr Asn Asn Gln Val Asn Arg Trp Thr Asn
    1010                1015                1020
Trp Thr Arg Thr Pro Arg Asp Ala Gly Asp Ser Ile Thr Val Asn
    1025                1030                1035
Phe Gly Lys Lys His Val Ile Asn Asn Leu Asp Leu Phe Val Phe
    1040                1045                1050
Thr Asp Ser Gly Thr Val Val Pro Glu Lys Ala Glu Val Gln Tyr
    1055                1060                1065
Trp Asp Gly Thr Ala Val Lys Asp Val Glu Asn Leu Thr Gln Pro
    1070                1075                1080
Ser Pro Tyr Val Val Glu Lys Asn Glu Leu Thr Phe Asp Ala Val
    1085                1090                1095
Ala Thr Glu Lys Leu Lys Phe His Leu Thr Pro Ser Val Lys Gly
    1100                1105                1110
Lys Phe Leu Ala Leu Thr Glu Ala Glu Val Tyr Ala Asp Gln Ile
    1115                1120                1125
Val Asp Gly Glu Thr Ala Lys Leu Gln Ser Ile Thr Val Asn Gly
    1130                1135                1140
Lys Ala Leu Glu Gly Phe Asp His Ala Lys Lys Asn Tyr Glu Leu
    1145                1150                1155
Val Leu Pro Tyr Gly Ser Glu Leu Pro Lys Ile Glu Ala Ala Ala
    1160                1165                1170
Ala Asp Asn Ala Thr Val Thr Ile Leu Pro Ala Phe Ser Tyr Pro
    1175                1180                1185
Gly Thr Ala Lys Leu Phe Val Thr Ser Glu Asp Gly Lys Val Thr
    1190                1195                1200
Thr Glu Tyr Ser Ile Gly Val Ser Thr Glu Glu Pro Lys Leu Val
    1205                1210                1215
Ser Ala Glu Leu Ser
    1220

<210> SEQ ID NO 5
<211> LENGTH: 2436
<212> TYPE: DNA
```

<213> ORGANISM: Artificial Sequence
<220> FEATURE:
<223> OTHER INFORMATION: The sequence is synthesized

<400> SEQUENCE: 5

| | | | | | |
|---|---|---|---|---|---|
| atgaaaagca | cgacgagcgc | cgccggcaaa | agcgtcagct | ataacgacgg | cgaacgccgc | 60 |
| gtcaactttg | aaaactggcg | ctttcagcgc | gaaacgaacg | gcagcatcgc | cggcgcccag | 120 |
| aacccgggct | ttgacgacag | cagctggcgc | aaactgaacc | tgccgcatga | atggagcatc | 180 |
| gacctggact | taacaaaaa | cagcctggcc | acgcatgaag | gcggctatct | ggacggcggc | 240 |
| atcggctgga | accgcaaaac | gtttacgatc | ccggaaagca | tgaaaggcaa | acgctttagc | 300 |
| ctggacatcg | acggcgtcta | tatgtatagc | acgacgtatc | tgaacgcctt | tgtcctgggc | 360 |
| acgtatccgt | ttggctataa | cggcgaaagc | tatgacatca | gcgacaaact | gtataaagac | 420 |
| ggccgcgcca | acgtcctggt | cgtcaaagtc | aacacgaacc | agccgagcgg | ccgctggtat | 480 |
| agcggcagca | gcatctatcg | caacgtctat | ctgacggtca | cggacccgat | ccatgtcgcc | 540 |
| cgctatggca | cgtttgtcac | gacgccgaac | ctggaaaaaa | gcatcaaaga | agaccgcgac | 600 |
| gccgtcaaca | tcaaaacgaa | aatcagcaac | gccgaagcca | acaggtcaa | atcgccgac | 660 |
| aaaagcacga | tctatgacgg | cgccggcaac | acggtccaga | cggtcgaaac | ggaagaaaaa | 720 |
| acggccgccg | cgccacggt | cacgccgttt | gaacagaaca | cggtcatcaa | acagccgaaa | 780 |
| ctgtggagca | tcgacaaacc | gtatcgctat | aacctggtca | cggaagtcat | cgtcggcggc | 840 |
| cagacggtcg | acacgtatga | acgaaattt | ggcgtccgct | attttaaatt | tgacgaaaac | 900 |
| gaaggctata | gcctgaacgg | cgaatttatg | aaactgcatg | gcgtcagcat | gcatcatgac | 960 |
| ctggccggcg | gcgccgccct | gacgaacgcc | gcggcgtcg | aacgccagat | gcagatcatg | 1020 |
| aaagacgtcg | gcgtcaacgc | catccgcgtc | acgcataacc | cggccagccc | ggaactgggc | 1080 |
| ctggaatttg | ccgccaacaa | actgctgatc | atcgaagaag | cctttgacag | ctgggcccag | 1140 |
| agcaaaaaac | gtatgacta | tggccgcttt | tttaacgcct | gggccgaaca | tgacatcaaa | 1200 |
| gaaatggtcg | accgcggcaa | aaacgaaccg | gccatcatca | tgtggagcat | cggcaacgaa | 1260 |
| atctatgaca | cgacgaacgc | cgccggcgtc | gaaacggccc | gcaacctggt | cggctgggtc | 1320 |
| aaagaaatcg | acacgacgcc | gcgcgccacg | atcggcgaag | acaaaacgcg | cggcgacaac | 1380 |
| gtcacgccga | tcaacagcta | tcaaagaa | atctttaaca | tcgtcgacgt | cgtcggcctg | 1440 |
| aactatagcg | aaaacaacta | tgacggctat | cataaacaga | acccgagctg | gaaactgtat | 1500 |
| ggcagcgaaa | cgagcagcgc | cacgcgcagc | cgcggcgtct | atacgcagcc | gtatcagtat | 1560 |
| aaccatgaca | cgaaatatgc | cgacctgcag | cagagcagct | atgacaacga | ctatgtcggc | 1620 |
| tggggccgca | cggcccagga | cgcctggaaa | tatgaccgcg | acctgaaaca | tatcgccggc | 1680 |
| cagtttatct | ggacgggctt | tgactatatc | ggcgaaccga | cgccgtatta | taacagctat | 1740 |
| ccggccaaaa | gcagctattt | tggcgccgtc | gacacggccg | gctttccgaa | agacatcttt | 1800 |
| tattattatc | agagccagtg | gaaaaaagaa | ccgatggtcc | atctgctgcc | gcattggaac | 1860 |
| tggaaagaag | gcgaaaaagt | ccgcgtcctg | gcctatacga | acgccagcaa | agtcgaactg | 1920 |
| gtcctgaacg | gcgaaagcct | gggcaacgaa | aaatatgaca | caaacagac | gagctggggc | 1980 |
| gccccgtata | agaaacgaa | agacggcaaa | acgtatctgg | aatgggccgt | caaaccgctg | 2040 |
| aaaccgggca | aatttgacga | agccgtcgcc | gaaacggca | aagtcatcgc | ccgcgaccag | 2100 |
| gtcgtcacgg | ccggcgaacc | ggccagcgtc | cgcctgacgg | ccgaccgcaa | agtcgtcaaa | 2160 |
| gccgacggca | cggaccatag | ctttatcacg | gccgacatcg | tcgacagcaa | aggcatcgtc | 2220 |

```
gtcccggacg ccgaccatct gatcacgttt aacgtcacgg gccagggcga actggccggc    2280
gtcgacaacg gcaacgccag cagcgtcgaa cgctataaag acaacaaacg caaagccttt    2340
agcggcaaag ccctggccat cgtccagagc agcaaactga gcggcaaaat cacggtccat    2400
gccagcgtcg ccggcctgag cagcgacagc acgtaa                              2436
```

<210> SEQ ID NO 6
<211> LENGTH: 811
<212> TYPE: PRT
<213> ORGANISM: Artificial Sequence
<220> FEATURE:
<223> OTHER INFORMATION: The sequence is synthesized

<400> SEQUENCE: 6

```
Met Lys Ser Thr Thr Ser Ala Ala Gly Lys Ser Val Ser Tyr Asn Asp
1               5                   10                  15

Gly Glu Arg Arg Val Asn Phe Glu Asn Trp Arg Phe Gln Arg Glu Thr
            20                  25                  30

Asn Gly Ser Ile Ala Gly Ala Gln Asn Pro Gly Phe Asp Asp Ser Ser
        35                  40                  45

Trp Arg Lys Leu Asn Leu Pro His Glu Trp Ser Ile Asp Leu Asp Phe
    50                  55                  60

Asn Lys Asn Ser Leu Ala Thr His Glu Gly Gly Tyr Leu Asp Gly Gly
65                  70                  75                  80

Ile Gly Trp Asn Arg Lys Thr Phe Thr Ile Pro Glu Ser Met Lys Gly
                85                  90                  95

Lys Arg Phe Ser Leu Asp Ile Asp Gly Val Tyr Met Tyr Ser Thr Thr
            100                 105                 110

Tyr Leu Asn Ala Phe Val Leu Gly Thr Tyr Pro Phe Gly Tyr Asn Gly
        115                 120                 125

Glu Ser Tyr Asp Ile Ser Asp Lys Leu Tyr Lys Asp Gly Arg Ala Asn
    130                 135                 140

Val Leu Val Val Lys Val Asn Thr Asn Gln Pro Ser Gly Arg Trp Tyr
145                 150                 155                 160

Ser Gly Ser Ser Ile Tyr Arg Asn Val Tyr Leu Thr Val Thr Asp Pro
                165                 170                 175

Ile His Val Ala Arg Tyr Gly Thr Phe Val Thr Thr Pro Asn Leu Glu
            180                 185                 190

Lys Ser Ile Lys Glu Asp Arg Asp Ala Val Asn Ile Lys Thr Lys Ile
        195                 200                 205

Ser Asn Ala Glu Ala Lys Gln Val Lys Ile Ala Asp Lys Ser Thr Ile
    210                 215                 220

Tyr Asp Gly Ala Gly Asn Thr Val Gln Thr Val Glu Thr Glu Glu Lys
225                 230                 235                 240

Thr Ala Ala Gly Ala Thr Val Thr Pro Phe Glu Gln Asn Thr Val Ile
                245                 250                 255

Lys Gln Pro Lys Leu Trp Ser Ile Asp Lys Pro Tyr Arg Tyr Asn Leu
            260                 265                 270

Val Thr Glu Val Ile Val Gly Gly Gln Thr Val Asp Thr Tyr Glu Thr
        275                 280                 285

Lys Phe Gly Val Arg Tyr Phe Lys Phe Asp Glu Asn Glu Gly Tyr Ser
    290                 295                 300

Leu Asn Gly Glu Phe Met Lys Leu His Gly Val Ser Met His His Asp
305                 310                 315                 320
```

-continued

Leu Ala Gly Gly Ala Leu Thr Asn Ala Arg Gly Val Glu Arg Gln
                325                 330                 335

Met Gln Ile Met Lys Asp Val Gly Val Asn Ala Ile Arg Val Thr His
            340                 345                 350

Asn Pro Ala Ser Pro Glu Leu Gly Leu Glu Phe Ala Ala Asn Lys Leu
        355                 360                 365

Leu Ile Ile Glu Glu Ala Phe Asp Ser Trp Ala Gln Ser Lys Lys Pro
370                 375                 380

Tyr Asp Tyr Gly Arg Phe Phe Asn Ala Trp Glu His Asp Ile Lys
385                 390                 395                 400

Glu Met Val Asp Arg Gly Lys Asn Glu Pro Ala Ile Ile Met Trp Ser
                405                 410                 415

Ile Gly Asn Glu Ile Tyr Asp Thr Thr Asn Ala Ala Gly Val Glu Thr
            420                 425                 430

Ala Arg Asn Leu Val Gly Trp Val Lys Glu Ile Asp Thr Thr Pro Arg
        435                 440                 445

Ala Thr Ile Gly Glu Asp Lys Thr Arg Gly Asp Asn Val Thr Pro Ile
    450                 455                 460

Asn Ser Tyr Ile Lys Glu Ile Phe Asn Ile Val Asp Val Val Gly Leu
465                 470                 475                 480

Asn Tyr Ser Glu Asn Asn Tyr Asp Gly Tyr His Lys Gln Asn Pro Ser
                485                 490                 495

Trp Lys Leu Tyr Gly Ser Glu Thr Ser Ser Ala Thr Arg Ser Arg Gly
            500                 505                 510

Val Tyr Thr Gln Pro Tyr Gln Tyr Asn His Asp Thr Lys Tyr Ala Asp
        515                 520                 525

Leu Gln Gln Ser Ser Tyr Asp Asn Asp Tyr Val Gly Trp Gly Arg Thr
    530                 535                 540

Ala Gln Asp Ala Trp Lys Tyr Asp Arg Asp Leu Lys His Ile Ala Gly
545                 550                 555                 560

Gln Phe Ile Trp Thr Gly Phe Asp Tyr Ile Gly Glu Pro Thr Pro Tyr
                565                 570                 575

Tyr Asn Ser Tyr Pro Ala Lys Ser Ser Tyr Phe Gly Ala Val Asp Thr
            580                 585                 590

Ala Gly Phe Pro Lys Asp Ile Phe Tyr Tyr Gln Ser Gln Trp Lys
        595                 600                 605

Lys Glu Pro Met Val His Leu Leu Pro His Trp Asn Trp Lys Glu Gly
    610                 615                 620

Glu Lys Val Arg Val Leu Ala Tyr Thr Asn Ala Ser Lys Val Glu Leu
625                 630                 635                 640

Val Leu Asn Gly Glu Ser Leu Gly Asn Glu Lys Tyr Asp Asn Lys Gln
                645                 650                 655

Thr Ser Trp Gly Ala Pro Tyr Lys Glu Thr Lys Asp Gly Lys Thr Tyr
            660                 665                 670

Leu Glu Trp Ala Val Lys Pro Leu Lys Pro Gly Lys Phe Asp Glu Ala
        675                 680                 685

Val Ala Glu Asn Gly Lys Val Ile Ala Arg Asp Gln Val Val Thr Ala
    690                 695                 700

Gly Glu Pro Ala Ser Val Arg Leu Thr Ala Asp Arg Lys Val Val Lys
705                 710                 715                 720

Ala Asp Gly Thr Asp His Ser Phe Ile Thr Ala Asp Ile Val Asp Ser
                725                 730                 735

Lys Gly Ile Val Val Pro Asp Ala Asp His Leu Ile Thr Phe Asn Val

```
                740                 745                 750
Thr Gly Gln Gly Glu Leu Ala Gly Val Asp Asn Gly Asn Ala Ser Ser
            755                 760                 765

Val Glu Arg Tyr Lys Asp Asn Lys Arg Lys Ala Phe Ser Gly Lys Ala
        770                 775                 780

Leu Ala Ile Val Gln Ser Ser Lys Leu Ser Gly Lys Ile Thr Val His
785                 790                 795                 800

Ala Ser Val Ala Gly Leu Ser Ser Asp Ser Thr
                805                 810

<210> SEQ ID NO 7
<211> LENGTH: 5133
<212> TYPE: DNA
<213> ORGANISM: B. circulans ATCC 31382

<400> SEQUENCE: 7
```

| | | | | |
|---|---|---|---|---|
| atgagcaaaa cgacgagcgc cgccggcaac agcgtcagct atgacggcga acgccgcgtc | 60 |
| aactttaacg aaaactggcg ctttcagcgc gaaacgaacg gcagcatcgc cggcgcccag | 120 |
| aacccaggct tgacgacag cagctggcg aaactgaacc tgccgcatga ctggagcatc | 180 |
| gaactggact ttaacaaaaa cagcctggcc acgcatgaag gcggctatct ggacggcggc | 240 |
| atcggctggt atcgcaaaac gtttacgatc ccggaaagca tgaaaggcaa acgcatcagc | 300 |
| ctggactttg acgcgtcta tatgaacagc acgacgtatc tgaacggcga agtcctgggc | 360 |
| acgtatccgt ttggctataa cgcctttagc tatgacatca gcgacaaact gtataaagac | 420 |
| ggccgcgcca acgtcctggt cgtcaaagtc aacaacacgc agccgagcag ccgctggtat | 480 |
| agcggcagcg gcatctatcg caacgtctat ctgacggtca cggacccgat ccatgtcgcc | 540 |
| cgctatggca cgtttgtcac gacgccgaac ctggaaaaaa gcatcaaaga agaccgcgcc | 600 |
| gacgtcaaca tcaaaacgaa aatcagcaac gacgccgccg aagccaaaca ggtcaaaatc | 660 |
| aaaagcacga tctatgacgg cgccggcaac acggtccaga cggtcgaaac ggaagaaaaa | 720 |
| acggccgccg ccggcacggt cacgccgttt gaacagaaca cggtcatcaa acagccgaaa | 780 |
| ctgtggagca tcgacaaacc gtatcgctat aacctggtca cggaagtcat cgtcggcggc | 840 |
| cagacggtcg acacgtatga acgaaatt ggcgtccgct atttaaatt tgacgaaaac | 900 |
| gaaggcttta gcctgaacgg cgaatatatg aaactgcatg gcgtcagcat gcatcatgac | 960 |
| ctgggcgccc tgggcgccgc cacgaacgcc cgcggcgtcg aacgccagat gcagatcatg | 1020 |
| aaagacatgg gcgtcaacgc catccgcgtc acgcataacc cggccagccc ggaactgctg | 1080 |
| gaagccgcca acaaactggg cctgtttatc atcgaagaag cctttgacag ctgggcccag | 1140 |
| agcaaaaaac cgtatgacta tggccgcttt tttaacgcct gggccgaaca tgacatcaaa | 1200 |
| gaaatggtcg accgcggcaa aaacgaaccg gccatcatca tgtggagcat cggcaacgaa | 1260 |
| atctatgaca cgacgaacgc cgccggcgtc gaaacggccc gcaacctggt cggctgggtc | 1320 |
| aaagaaatcg acacgacgcg cccgacgacg atcggcgaag acaaaacgcg cggcgacaaa | 1380 |
| gtcaacgtca cgccgatcaa cagctatatc aaagaaatct taacatcgt cgacgtcgtc | 1440 |
| ggcctgaact atagcgaaaa caactatgac ggctatcata acagaaccc gagctggaaa | 1500 |
| ctgtatggca gcgaaacgag cagcgccacg cgcagccgcg gcgtctatac gcatccgtat | 1560 |
| cagtataacc agagcacgaa atatgccgac ctgcagcaga gcagctatga caacgactat | 1620 |
| gtcggctggg gccgcacggc cgaagacgcc tggaaatatg accgcgacct gaaacatatc | 1680 |
| gccggccagt ttatctggac gggctttgac tatatcggcg aaccgacgcc gtattataac | 1740 |

```
agctatccgg ccaaaagcag ctatttggc gccgtcgaca cggccggctt tccgaaagac    1800
atcttttatt attatcagag ccagtggaaa aagaaccga tggtccatct gctgccgcat    1860
tggaactgga agaaggcga aaaagtccgc gtcctggcct atacgaacgc cagcaaagtc    1920
gaactggtcc tgaacggcga aagcctgggc gaaaaaaact atgacaacaa acagacgagc    1980
tggggcgccc cgtataaaga aacgaaagac ggcaaaacgt atctggaatg gccgtcccg    2040 tttaaaccgg gcaaactgga agccgtcgcc aaagacgaaa acggcaaagt catcgcccgc    2100
gaccaggtcg tcacggccgg cgaaccggcc agcgtccgcc tgacggccga ccgcaaagtc    2160
gtcaaagccg acggcacgga cctgagcttt atcacggccg acatcgtcga cagcaaaggc    2220
atcgtcgtcc cggacgccga ccatctgatc acgtttaacg tcacgggcca gggcgaactg    2280
gccggcgtcg acaacggcaa cgccagcagc gtcgaacgct ataaagacaa caaacgcaaa    2340
gcctttagcg gcaaagccct ggccatcgtc cagagcagca aactgagcgg caaaatcacg    2400
gtccatgcca gcgtcgccgg cctgagcagc gacagcacga gcgtctttac ggtcacgccg    2460
gccgaccatg acaaaaaaat cgtcgccggc atcgacgacg tcaacctgac ggtcgacgtc    2520
aacgaagccc cgaaactgcc gagcgaaatc aaagtctatt atagcgacga aagcgccgcc    2580
gccaaaaacg tcacgtggga cgaagtcgac ccgaaacagt atagcacggt cggcgaattt    2640
acggtcgaag gcagcgtcga aggcacgagc ctgaaagcca agcctttgt catcgtcaaa    2700 ggcatcgtcg ccgtcaaacc gtatagcacg gccacgaaag tcggcgtcca gccggtcctg    2760
ccggaaaaag ccacgctgct gtatagcgac ggcacgacga aaggcgccac ggtcacgtgg    2820
gacgaaatcc cggaagacaa actggccaaa gaaggccgct ttacggtcga aggcagcgtc    2880
gaaggcacgg acctgaaagc caacgtctat gtccgcgtca cgaacgaagt caaaagcgtc    2940
aacatcatgc tgcaggaaca gggcagcgcc tatccgaaac tggaagccac gtttacgaac    3000
ccggccgaca acctgcagca tctgaacgac ggcatcaaaa gctatacgaa caacccggtc    3060
aaccgctgga cgaactggac gcgcacgccg cgcgacgccg gcgacagcat cacggtcaac    3120
tttggcaaaa acatgtcat caacaacctg gacctgtttg tctttacgga cagcggcacg    3180
gtcgtcccgg aaaagccga agtccagtat tgggacggca cggcctggaa agacgtcgaa    3240
aacctgacgc agccgagccc gtatgtcgtc gaaaaaaacg aactgacgtt tgacgccgtc    3300
gccacggaaa aactgaaatt tcatctgacg ccgagcgtca aggcaaatt tctgccctg    3360 acggaagccg aagtctatgc cgaccagatc gtcatgggcg aaacggccaa actgcagagc    3420
atcacggtca acggcaaagc cctggaaggc tttgaccatg ccaaaaaaaa ctatgaactg    3480
gtcctgccgt atggcagcga actgccgaaa atcgaagccg ccgccgccga caacgccacg    3540
gtcacgatcc tgccggcctt tagctatccg ggcacggcca aactgtttgt cacgagcgaa    3600
gacggcaaag tcacgacgga atatagcatc ggcgtcagca cggaagaacc gaaactggtc    3660
agcgccgaac tgagcgccga caaaacgaac gtcatggaag acgacatcat cgacctgaaa    3720
gtcatcggcc tgtttgaaag caagaaaaa atcgacgtca cggacagcca gccgacgtat    3780
gaatttgacc agcagatcat caaaatcgaa ggcaacaaac tgtatgccct ggaaacgggc    3840
aacgtcaaag tcaaagtcac ggtcacgtat aaaggcgtca cgtcacgac gccggccctg    3900 gaatttacga tcgccaaaaa cccggccccg aaatatatca cgagcctgga accggtcacg    3960
gtcgtcgtca aaaaaggcga agccccggaa ctgccggcca cggtcgtcgc ccattataac    4020
cgcggcatcc cgcgcgacgt caaagtcaaa tgggaacgca tcaacccgag caaatatcag    4080
```

-continued

```
cagctgggcg aatttacggt cagcggcatg gtcgaaggca cggacatcaa agcccaggcc    4140
aaagtcatcg tcaaaggcgc cgtcgccgtc gaagacatcc gcatggccgt cctgctgaaa    4200
cagatgccgc agctgccggg caaagtcacg gtctattata gcgacggcgc cgaagaacag    4260
cgcgccgtca atgggaaga aatcccgcag gaagaactgg aaaacgtcgg cgaatttaaa     4320
gtcaaaggcg acgtcaacgg cgtcaaactg aaagccacgg ccacgatccg cgtcacggac    4380
gaagtcggcg cgaacagaa catcagccgc gccaaaaacg gctatgaata tccgaaagcc    4440
gaagccagct ttacgaacaa cggcccaggc agcagcgacc gcatcgaagc catcaacgac    4500
gacgtcatca gctatgaagc caacccgcat aaccgctgga cgaactggca gccggtcccg    4560
cgcgccggcg actgggtcag catcacgttt ggcgactatg aaccgacgga atatgacgtc    4620
gacagcatgg aaatccattg gtttgccgac catggcacga gctatccgga acgctttcag    4680
atcgaatata aagcggcga cagctggaaa gaagtcacga gcctgaaaag cgacccggcc    4740
agcccggccc tgggcaaagc caacgtctat agctttgacc gcgtcaaaac gagcgccatc    4800
cgcgtcaaaa tgacggccca ggccggcaaa agcctggcca tcacggaact gaaagtctt   4860 agcaaatggc cgaaagccgg cacggaaccg gaagtcacgg acatcaaagt cggcggcaaa    4920
agcatcctgg aagactttga acagaaaggc gaccattatg aagtcacgat cgacgccggc    4980
gacgccaacg tcatgccgaa aatcaacgtc aaagccaaag accagacgag catcacgatc    5040
gtcccggccg tcacgagccc gagcacggcc aagtcatcg ccaaaagcga agacggcaaa    5100
aaagtcaaag tctatagcat ccattataaa taa                                 5133
```

<210> SEQ ID NO 8
<211> LENGTH: 1710
<212> TYPE: PRT
<213> ORGANISM: B. circulans ATCC 31382

<400> SEQUENCE: 8

```
Met Ser Lys Thr Thr Ser Ala Ala Gly Asn Ser Val Ser Tyr Asp Gly
  1               5                  10                  15

Glu Arg Arg Val Asn Phe Asn Glu Asn Trp Arg Phe Gln Arg Glu Thr
             20                  25                  30

Asn Gly Ser Ile Ala Gly Ala Gln Asn Pro Gly Phe Asp Asp Ser Ser
         35                  40                  45

Trp Arg Lys Leu Asn Leu Pro His Asp Trp Ser Ile Glu Leu Asp Phe
     50                  55                  60

Asn Lys Asn Ser Leu Ala Thr His Glu Gly Gly Tyr Leu Asp Gly Gly
 65                  70                  75                  80

Ile Gly Trp Tyr Arg Lys Thr Phe Thr Ile Pro Glu Ser Met Lys Gly
                 85                  90                  95

Lys Arg Ile Ser Leu Asp Phe Asp Gly Val Tyr Met Asn Ser Thr Thr
            100                 105                 110

Tyr Leu Asn Gly Glu Val Leu Gly Thr Tyr Pro Phe Gly Tyr Asn Ala
        115                 120                 125

Phe Ser Tyr Asp Ile Ser Asp Lys Leu Tyr Lys Asp Gly Arg Ala Asn
    130                 135                 140

Val Leu Val Val Lys Val Asn Asn Thr Gln Pro Ser Ser Arg Trp Tyr
145                 150                 155                 160

Ser Gly Ser Gly Ile Tyr Arg Asn Val Tyr Leu Thr Val Thr Asp Pro
                165                 170                 175

Ile His Val Ala Arg Tyr Gly Thr Phe Val Thr Thr Pro Asn Leu Glu
            180                 185                 190
```

```
        Lys Ser Ile Lys Glu Asp Arg Ala Asp Val Asn Ile Lys Thr Lys Ile
                    195                 200                 205

Ser Asn Asp Ala Ala Glu Ala Lys Gln Val Lys Ile Lys Ser Thr Ile
                    210                 215                 220

Tyr Asp Gly Ala Gly Asn Thr Val Gln Thr Val Glu Thr Glu Lys
        225                 230                 235                 240

Thr Ala Ala Ala Gly Thr Val Thr Pro Phe Glu Gln Asn Thr Val Ile
                        245                 250                 255

Lys Gln Pro Lys Leu Trp Ser Ile Asp Lys Pro Tyr Arg Tyr Asn Leu
                    260                 265                 270

Val Thr Glu Val Ile Val Gly Gly Gln Thr Val Asp Thr Tyr Glu Thr
                    275                 280                 285

Lys Phe Gly Val Arg Tyr Phe Lys Phe Asp Glu Asn Glu Gly Phe Ser
                    290                 295                 300

Leu Asn Gly Glu Tyr Met Lys Leu His Gly Val Ser Met His His Asp
        305                 310                 315                 320

Leu Gly Ala Leu Gly Ala Ala Thr Asn Ala Arg Gly Val Glu Arg Gln
                        325                 330                 335

Met Gln Ile Met Lys Asp Met Gly Val Asn Ala Ile Arg Val Thr His
                    340                 345                 350

Asn Pro Ala Ser Pro Glu Leu Leu Glu Ala Ala Asn Lys Leu Gly Leu
                    355                 360                 365

Phe Ile Ile Glu Glu Ala Phe Asp Ser Trp Ala Gln Ser Lys Lys Pro
                    370                 375                 380

Tyr Asp Tyr Gly Arg Phe Phe Asn Ala Trp Ala Glu His Asp Ile Lys
        385                 390                 395                 400

Glu Met Val Asp Arg Gly Lys Asn Glu Pro Ala Ile Ile Met Trp Ser
                        405                 410                 415

Ile Gly Asn Glu Ile Tyr Asp Thr Thr Asn Ala Ala Gly Val Glu Thr
                    420                 425                 430

Ala Arg Asn Leu Val Gly Trp Val Lys Glu Ile Asp Thr Thr Arg Pro
                    435                 440                 445

Thr Thr Ile Gly Glu Asp Lys Thr Arg Gly Asp Lys Val Asn Val Thr
                    450                 455                 460

Pro Ile Asn Ser Tyr Ile Lys Glu Ile Phe Asn Ile Val Asp Val Val
        465                 470                 475                 480

Gly Leu Asn Tyr Ser Glu Asn Asn Tyr Asp Gly Tyr His Lys Gln Asn
                        485                 490                 495

Pro Ser Trp Lys Leu Tyr Gly Ser Glu Thr Ser Ser Ala Thr Arg Ser
                    500                 505                 510

Arg Gly Val Tyr Thr His Pro Tyr Gln Tyr Asn Gln Ser Thr Lys Tyr
                    515                 520                 525

Ala Asp Leu Gln Gln Ser Ser Tyr Asp Asn Asp Tyr Val Gly Trp Gly
                    530                 535                 540

Arg Thr Ala Glu Asp Ala Trp Lys Tyr Asp Arg Asp Leu Lys His Ile
        545                 550                 555                 560

Ala Gly Gln Phe Ile Trp Thr Gly Phe Asp Tyr Ile Gly Glu Pro Thr
                        565                 570                 575

Pro Tyr Tyr Asn Ser Tyr Pro Ala Lys Ser Ser Tyr Phe Gly Ala Val
                    580                 585                 590

Asp Thr Ala Gly Phe Pro Lys Asp Ile Phe Tyr Tyr Gln Ser Gln
                    595                 600                 605
```

-continued

```
Trp Lys Lys Glu Pro Met Val His Leu Leu Pro His Trp Asn Trp Lys
610                 615                 620
Glu Gly Glu Lys Val Arg Val Leu Ala Tyr Thr Asn Ala Ser Lys Val
625                 630                 635                 640
Glu Leu Val Leu Asn Gly Glu Ser Leu Gly Glu Lys Asn Tyr Asp Asn
            645                 650                 655
Lys Gln Thr Ser Trp Gly Ala Pro Tyr Lys Glu Thr Lys Asp Gly Lys
            660                 665                 670
Thr Tyr Leu Glu Trp Ala Val Pro Phe Lys Pro Gly Lys Leu Glu Ala
        675                 680                 685
Val Ala Lys Asp Glu Asn Gly Lys Val Ile Ala Arg Asp Gln Val Val
690                 695                 700
Thr Ala Gly Glu Pro Ala Ser Val Arg Leu Thr Ala Asp Arg Lys Val
705                 710                 715                 720
Val Lys Ala Asp Gly Thr Asp Leu Ser Phe Ile Thr Ala Asp Ile Val
                725                 730                 735
Asp Ser Lys Gly Ile Val Val Pro Asp Ala Asp His Leu Ile Thr Phe
            740                 745                 750
Asn Val Thr Gly Gln Gly Glu Leu Ala Gly Val Asp Asn Gly Asn Ala
        755                 760                 765
Ser Ser Val Glu Arg Tyr Lys Asp Asn Lys Arg Lys Ala Phe Ser Gly
770                 775                 780
Lys Ala Leu Ala Ile Val Gln Ser Ser Lys Leu Ser Gly Lys Ile Thr
785                 790                 795                 800
Val His Ala Ser Val Ala Gly Leu Ser Ser Asp Ser Thr Ser Val Phe
                805                 810                 815
Thr Val Thr Pro Ala Asp His Asp Lys Lys Ile Val Ala Gly Ile Asp
            820                 825                 830
Asp Val Asn Leu Thr Val Asp Val Asn Glu Ala Pro Lys Leu Pro Ser
        835                 840                 845
Glu Ile Lys Val Tyr Tyr Ser Asp Glu Ser Ala Ala Lys Asn Val
850                 855                 860
Thr Trp Asp Glu Val Asp Pro Lys Gln Tyr Ser Thr Val Gly Glu Phe
865                 870                 875                 880
Thr Val Glu Gly Ser Val Glu Gly Thr Ser Leu Lys Ala Lys Ala Phe
                885                 890                 895
Val Ile Val Lys Gly Ile Val Ala Val Lys Pro Tyr Ser Thr Ala Thr
            900                 905                 910
Lys Val Gly Val Gln Pro Val Leu Pro Glu Lys Ala Thr Leu Leu Tyr
        915                 920                 925
Ser Asp Gly Thr Thr Lys Gly Ala Thr Val Thr Trp Asp Glu Ile Pro
930                 935                 940
Glu Asp Lys Leu Ala Lys Glu Gly Arg Phe Thr Val Glu Gly Ser Val
945                 950                 955                 960
Glu Gly Thr Asp Leu Lys Ala Asn Val Tyr Val Arg Val Thr Asn Glu
                965                 970                 975
Val Lys Ser Val Asn Ile Met Leu Gln Glu Gln Gly Ser Ala Tyr Pro
            980                 985                 990
Lys Leu Glu Ala Thr Phe Thr Asn Pro Ala Asp Asn Leu Gln His Leu
        995                 1000                1005
Asn Asp Gly Ile Lys Ser Tyr Thr Asn Asn Pro Val Asn Arg Trp
        1010                1015                1020
Thr Asn Trp Thr Arg Thr Pro Arg Asp Ala Gly Asp Ser Ile Thr
```

-continued

```
            1025                1030                1035
Val Asn Phe Gly Lys Lys His Val Ile Asn Asn Leu Asp Leu Phe
            1040                1045                1050
Val Phe Thr Asp Ser Gly Thr Val Val Pro Glu Lys Ala Glu Val
            1055                1060                1065
Gln Tyr Trp Asp Gly Thr Ala Trp Lys Asp Val Glu Asn Leu Thr
            1070                1075                1080
Gln Pro Ser Pro Tyr Val Val Glu Lys Asn Glu Leu Thr Phe Asp
            1085                1090                1095
Ala Val Ala Thr Glu Lys Leu Lys Phe His Leu Thr Pro Ser Val
            1100                1105                1110
Lys Gly Lys Phe Leu Ala Leu Thr Glu Ala Glu Val Tyr Ala Asp
            1115                1120                1125
Gln Ile Val Met Gly Glu Thr Ala Lys Leu Gln Ser Ile Thr Val
            1130                1135                1140
Asn Gly Lys Ala Leu Glu Gly Phe Asp His Ala Lys Lys Asn Tyr
            1145                1150                1155
Glu Leu Val Leu Pro Tyr Gly Ser Glu Leu Pro Lys Ile Glu Ala
            1160                1165                1170
Ala Ala Ala Asp Asn Ala Thr Val Thr Ile Leu Pro Ala Phe Ser
            1175                1180                1185
Tyr Pro Gly Thr Ala Lys Leu Phe Val Thr Ser Glu Asp Gly Lys
            1190                1195                1200
Val Thr Thr Glu Tyr Ser Ile Gly Val Ser Thr Glu Glu Pro Lys
            1205                1210                1215
Leu Val Ser Ala Glu Leu Ser Ala Asp Lys Thr Asn Val Met Glu
            1220                1225                1230
Asp Asp Ile Ile Asp Leu Lys Val Ile Gly Leu Phe Glu Ser Lys
            1235                1240                1245
Glu Lys Ile Asp Val Thr Asp Ser Gln Pro Thr Tyr Glu Phe Asp
            1250                1255                1260
Gln Gln Ile Ile Lys Ile Glu Gly Asn Lys Leu Tyr Ala Leu Glu
            1265                1270                1275
Thr Gly Asn Val Lys Val Lys Val Thr Val Thr Tyr Lys Gly Val
            1280                1285                1290
Ser Val Thr Thr Pro Ala Leu Glu Phe Thr Ile Ala Lys Asn Pro
            1295                1300                1305
Ala Pro Lys Tyr Ile Thr Ser Leu Glu Pro Val Thr Val Val Val
            1310                1315                1320
Lys Lys Gly Glu Ala Pro Glu Leu Pro Ala Thr Val Val Ala His
            1325                1330                1335
Tyr Asn Arg Gly Ile Pro Arg Asp Val Lys Val Lys Trp Glu Arg
            1340                1345                1350
Ile Asn Pro Ser Lys Tyr Gln Gln Leu Gly Glu Phe Thr Val Ser
            1355                1360                1365
Gly Met Val Glu Gly Thr Asp Ile Lys Ala Gln Ala Lys Val Ile
            1370                1375                1380
Val Lys Gly Ala Val Ala Val Glu Asp Ile Arg Met Ala Val Leu
            1385                1390                1395
Leu Lys Gln Met Pro Gln Leu Pro Gly Lys Val Thr Val Tyr Tyr
            1400                1405                1410
Ser Asp Gly Ala Glu Glu Gln Arg Ala Val Lys Trp Glu Glu Ile
            1415                1420                1425
```

```
Pro Gln Glu Glu Leu Glu Asn Val Gly Glu Phe Lys Val Lys Gly
    1430                1435                1440

Asp Val Asn Gly Val Lys Leu Lys Ala Thr Ala Thr Ile Arg Val
    1445                1450                1455

Thr Asp Glu Val Gly Gly Glu Gln Asn Ile Ser Arg Ala Lys Asn
    1460                1465                1470

Gly Tyr Glu Tyr Pro Lys Ala Glu Ala Ser Phe Thr Asn Asn Gly
    1475                1480                1485

Pro Gly Ser Ser Asp Arg Ile Glu Ala Ile Asn Asp Asp Val Ile
    1490                1495                1500

Ser Tyr Glu Ala Asn Pro His Asn Arg Trp Thr Asn Trp Gln Pro
    1505                1510                1515

Val Pro Arg Ala Gly Asp Trp Val Ser Ile Thr Phe Gly Asp Tyr
    1520                1525                1530

Glu Pro Thr Glu Tyr Asp Val Asp Ser Met Glu Ile His Trp Phe
    1535                1540                1545

Ala Asp His Gly Thr Ser Tyr Pro Glu Arg Phe Gln Ile Glu Tyr
    1550                1555                1560

Lys Ser Gly Asp Ser Trp Lys Glu Val Thr Ser Leu Lys Ser Asp
    1565                1570                1575

Pro Ala Ser Pro Ala Leu Gly Lys Ala Asn Val Tyr Ser Phe Asp
    1580                1585                1590

Arg Val Lys Thr Ser Ala Ile Arg Val Lys Met Thr Ala Gln Ala
    1595                1600                1605

Gly Lys Ser Leu Ala Ile Thr Glu Leu Lys Val Phe Ser Lys Trp
    1610                1615                1620

Pro Lys Ala Gly Thr Glu Pro Glu Val Thr Asp Ile Lys Val Gly
    1625                1630                1635

Gly Lys Ser Ile Leu Glu Asp Phe Glu Gln Lys Gly Asp His Tyr
    1640                1645                1650

Glu Val Thr Ile Asp Ala Gly Asp Ala Asn Val Met Pro Lys Ile
    1655                1660                1665

Asn Val Lys Ala Lys Asp Gln Thr Ser Ile Thr Ile Val Pro Ala
    1670                1675                1680

Val Thr Ser Pro Ser Thr Ala Lys Val Ile Ala Lys Ser Glu Asp
    1685                1690                1695

Gly Lys Lys Val Lys Val Tyr Ser Ile His Tyr Lys
    1700                1705                1710

<210> SEQ ID NO 9
<211> LENGTH: 3669
<212> TYPE: DNA
<213> ORGANISM: Artificial Sequence
<220> FEATURE:
<223> OTHER INFORMATION: The sequence is synthesized

<400> SEQUENCE: 9
atgagcaaaa cgacgagcgc cgccggcaac agcgtcagct atgacggcga acgccgcgtc      60
aactttaacg aaaactggcg ctttcagcgc gaaacgaacg gcagcatcgc cggcgcccag     120
aacccaggct tgacgacag cagctggcgc aaactgaacc tgccgcatga ctggagcatc      180
gaactggact ttaacaaaaa cagcctggcc acgcatgaag cggctatcct ggacggcggc     240
atcggctggt atcgcaaaac gtttacgatc ccggaaagca tgaaaggcaa acgcatcagc     300
ctggactttg acggcgtcta tatgaacagc acgacgtatc tgaacggcga agtcctgggc     360
```

```
acgtatccgt tggctataa cgcctttagc tatgacatca gcgacaaact gtataaagac    420
ggccgcgcca acgtcctggt cgtcaaagtc aacaacacgc agccgagcag ccgctggtat    480
agcggcagcg gcatctatcg caacgtctat ctgacggtca cggacccgat ccatgtcgcc    540
cgctatggca cgtttgtcac gacgccgaac ctggaaaaaa gcatcaaaga agaccgcgcc    600
gacgtcaaca tcaaaacgaa aatcagcaac gacgccgccg aagccaaaca ggtcaaaatc    660
aaaagcacga tctatgacgg cgccggcaac acggtccaga cggtcgaaac ggaagaaaaa    720
acggccgccg ccggcacggt cacgccgttt gaacagaaca cggtcatcaa acagccgaaa    780
ctgtggagca tcgacaaacc gtatcgctat aacctggtca cggaagtcat cgtcggcggc    840
cagacggtcg acacgtatga acgaaatttt ggcgtccgct attttaaatt tgacgaaaac    900
gaaggcttta gcctgaacgg cgaatatatg aaactgcatg gcgtcagcat gcatcatgac    960
ctgggcgccc tgggcgccgc cacgaacgcc cgcggcgtcg aacgccagat gcagatcatg   1020
aaagacatgg gcgtcaacgc catccgcgtc acgcataacc cggccagccc ggaactgctg   1080
gaagccgcca acaaactggg cctgtttatc atcgaagaag cctttgacag ctgggcccag   1140
agcaaaaaac cgtatgacta tggccgcttt tttaacgcct gggccgaaca tgacatcaaa   1200
gaaatggtcg accgcggcaa aaacgaaccg gccatcatca tgtggagcat cggcaacgaa   1260
atctatgaca cgacgaacgc cgccggcgtc gaaacggccc gcaacctggt cggctgggtc   1320
aaagaaatcg acacgacgcg cccgacgacg atcggcgaag acaaaacgcg cggcgacaaa   1380
gtcaacgtca cgccgatcaa cagctatatc aaagaaatct ttaacatcgt cgacgtcgtc   1440
ggcctgaact atagcgaaaa caactatgac ggctatcata acagaacccc gagctggaaa   1500
ctgtatggca cgaaacgag cagcgccacg cgcagccgcg cgtctatac gcatccgtat   1560 cagtataacc agagcacgaa atatgccgac ctgcagcaga gcagctatga caacgactat   1620
gtcggctggg gccgcacggc cgaagacgcc tggaaatatg accgcgacct gaaacatatc   1680
gccggccagt ttatctggac gggctttgac tatatcggcg aaccgacgcc gtattataac   1740
agctatccgg ccaaaagcag ctattttggc ccgtcgaca cggccggctt tccgaaaagac   1800 atctttatt attatcagag ccagtggaaa aagaaccga tggtccatct gctgccgcat   1860
tggaactgga agaaggcga aaagtccgc gtcctggcct atacgaacgc cagcaaagtc   1920
gaactggtcc tgaacggcga aagcctgggc gaaaaaaact atgacaacaa acagacgagc   1980
tggggcgccc cgtataaaga aacgaaagac ggcaaaacgt atctggaatg gccgtcccg   2040 tttaaaccgg gcaaactgga agccgtcgcc aaagacgaaa acggcaaagt catcgcccgc   2100
gaccaggtcg tcacggccgg cgaaccggcc agcgtccgcc tgacggccga ccgcaaagtc   2160
gtcaaagccc acggcacgga cctgagcttt atcacggccg acatcgtcga cagcaaaggc   2220
atcgtcgtcc cggacgccga ccatctgatc acgtttaacg tcacgggcca gggcgaactg   2280
gccggcgtcg acaacggcaa cgccagcagc gtcgaacgct ataaagacaa caaacgcaaa   2340
gcctttagcg gcaaagccct ggccatcgtc cagagcagca aactgagcgg caaaatcacg   2400
gtccatgcca gcgtcgccgg cctgagcagc gacagcacga gcgtctttac ggtcacgccg   2460
gccgaccatg acaaaaaaat cgtcgccggc atcgacgacg tcaacctgac ggtcgacgtc   2520
aacgaagccc cgaaactgcc gagcgaaatc aaagtctatt atagcgacga aagcgccgcc   2580
gccaaaaacg tcacgtggga cgaagtcgac ccgaaacagt atagcacggt cggcgaattt   2640
acggtcgaag gcagcgtcga aggcacgagc ctgaaagcca aagcctttgt catcgtcaaa   2700
```

```
ggcatcgtcg ccgtcaaacc gtatagcacg gccacgaaag tcggcgtcca gccggtcctg    2760
ccggaaaaag ccacgctgct gtatagcgac ggcacgacga aaggcgccac ggtcacgtgg    2820
gacgaaatcc cggaagacaa actggccaaa gaaggccgct ttacggtcga aggcagcgtc    2880
gaaggcacgg acctgaaagc caacgtctat gtccgcgtca cgaacgaagt caaaagcgtc    2940
aacatcatgc tgcaggaaca gggcagcgcc tatccgaaac tggaagccac gtttacgaac    3000
ccggccgaca acctgcagca tctgaacgac ggcatcaaaa gctatacgaa caacccggtc    3060
aaccgctgga cgaactggac gcgcacgccg cgcgacgccg gcgacagcat cacggtcaac    3120
tttggcaaaa acatgtcat caacaacctg gacctgtttg tctttacgga cagcggcacg    3180
gtcgtcccgg aaaagccga agtccagtat tgggacggca cggcctggaa agacgtcgaa    3240
aacctgacgc agccgagccc gtatgtcgtc gaaaaaaacg aactgacgtt tgacgccgtc    3300
gccacggaaa aactgaaatt tcatctgacg ccgagcgtca aaggcaaatt tctggccctg    3360
acggaagccg aagtctatgc cgaccagatc gtcatgggcg aaacggccaa actgcagagc    3420
atcacggtca acggcaaagc cctggaaggc tttgaccatg ccaaaaaaaa ctatgaactg    3480
gtcctgccgt atggcagcga actgccgaaa atcgaagccg ccgccgccga caacgccacg    3540
gtcacgatcc tgccggcctt tagctatccg ggcacggcca aactgtttgt cacgagcgaa    3600
gacggcaaag tcacgacgga atatagcatc ggcgtcagca cggaagaacc gaaactggtc    3660
agcgcctaa                                                           3669
```

<210> SEQ ID NO 10
<211> LENGTH: 1222
<212> TYPE: PRT
<213> ORGANISM: Artificial Sequence
<220> FEATURE:
<223> OTHER INFORMATION: The sequence is synthesized

<400> SEQUENCE: 10

```
Met Ser Lys Thr Thr Ser Ala Ala Gly Asn Ser Val Ser Tyr Asp Gly
1               5                   10                  15

Glu Arg Arg Val Asn Phe Asn Glu Asn Trp Arg Phe Gln Arg Glu Thr
            20                  25                  30

Asn Gly Ser Ile Ala Gly Ala Gln Asn Pro Gly Phe Asp Asp Ser Ser
        35                  40                  45

Trp Arg Lys Leu Asn Leu Pro His Asp Trp Ser Ile Glu Leu Asp Phe
    50                  55                  60

Asn Lys Asn Ser Leu Ala Thr His Glu Gly Gly Tyr Leu Asp Gly Gly
65                  70                  75                  80

Ile Gly Trp Tyr Arg Lys Thr Phe Thr Ile Pro Glu Ser Met Lys Gly
                85                  90                  95

Lys Arg Ile Ser Leu Asp Phe Asp Gly Val Tyr Met Asn Ser Thr Thr
            100                 105                 110

Tyr Leu Asn Gly Glu Val Leu Gly Thr Tyr Pro Phe Gly Tyr Asn Ala
        115                 120                 125

Phe Ser Tyr Asp Ile Ser Asp Lys Leu Tyr Lys Asp Gly Arg Ala Asn
    130                 135                 140

Val Leu Val Val Lys Val Asn Asn Thr Gln Pro Ser Ser Arg Trp Tyr
145                 150                 155                 160

Ser Gly Ser Gly Ile Tyr Arg Asn Val Tyr Leu Thr Val Thr Asp Pro
                165                 170                 175

Ile His Val Ala Arg Tyr Gly Thr Phe Val Thr Thr Pro Asn Leu Glu
            180                 185                 190
```

-continued

```
Lys Ser Ile Lys Glu Asp Arg Ala Asp Val Asn Ile Lys Thr Lys Ile
            195                 200                 205
Ser Asn Asp Ala Ala Glu Ala Lys Gln Val Lys Ile Lys Ser Thr Ile
        210                 215                 220
Tyr Asp Gly Ala Gly Asn Thr Val Gln Thr Val Glu Thr Glu Lys
225                 230                 235                 240
Thr Ala Ala Ala Gly Thr Val Thr Pro Phe Glu Gln Asn Thr Val Ile
                245                 250                 255
Lys Gln Pro Lys Leu Trp Ser Ile Asp Lys Pro Tyr Arg Tyr Asn Leu
            260                 265                 270
Val Thr Glu Val Ile Val Gly Gly Gln Thr Val Asp Thr Tyr Glu Thr
            275                 280                 285
Lys Phe Gly Val Arg Tyr Phe Lys Phe Asp Glu Asn Glu Gly Phe Ser
        290                 295                 300
Leu Asn Gly Glu Tyr Met Lys Leu His Gly Val Ser Met His His Asp
305                 310                 315                 320
Leu Gly Ala Leu Gly Ala Ala Thr Asn Ala Arg Gly Val Glu Arg Gln
                325                 330                 335
Met Gln Ile Met Lys Asp Met Gly Val Asn Ala Ile Arg Val Thr His
            340                 345                 350
Asn Pro Ala Ser Pro Glu Leu Leu Glu Ala Ala Asn Lys Leu Gly Leu
        355                 360                 365
Phe Ile Ile Glu Glu Ala Phe Asp Ser Trp Ala Gln Ser Lys Lys Pro
    370                 375                 380
Tyr Asp Tyr Gly Arg Phe Phe Asn Ala Trp Ala Glu His Asp Ile Lys
385                 390                 395                 400
Glu Met Val Asp Arg Gly Lys Asn Glu Pro Ala Ile Ile Met Trp Ser
                405                 410                 415
Ile Gly Asn Glu Ile Tyr Asp Thr Thr Asn Ala Ala Gly Val Glu Thr
            420                 425                 430
Ala Arg Asn Leu Val Gly Trp Val Lys Glu Ile Asp Thr Thr Arg Pro
        435                 440                 445
Thr Thr Ile Gly Glu Asp Lys Thr Arg Gly Asp Lys Val Asn Val Thr
    450                 455                 460
Pro Ile Asn Ser Tyr Ile Lys Glu Ile Phe Asn Ile Val Asp Val Val
465                 470                 475                 480
Gly Leu Asn Tyr Ser Glu Asn Asn Tyr Asp Gly Tyr His Lys Gln Asn
                485                 490                 495
Pro Ser Trp Lys Leu Tyr Gly Ser Glu Thr Ser Ser Ala Thr Arg Ser
            500                 505                 510
Arg Gly Val Tyr Thr His Pro Tyr Gln Tyr Asn Gln Ser Thr Lys Tyr
        515                 520                 525
Ala Asp Leu Gln Gln Ser Ser Tyr Asp Asn Asp Tyr Val Gly Trp Gly
    530                 535                 540
Arg Thr Ala Glu Asp Ala Trp Lys Tyr Asp Arg Asp Leu Lys His Ile
545                 550                 555                 560
Ala Gly Gln Phe Ile Trp Thr Gly Phe Asp Tyr Ile Gly Glu Pro Thr
                565                 570                 575
Pro Tyr Tyr Asn Ser Tyr Pro Ala Lys Ser Ser Tyr Phe Gly Ala Val
            580                 585                 590
Asp Thr Ala Gly Phe Pro Lys Asp Ile Phe Tyr Tyr Gln Ser Gln
        595                 600                 605
```

```
Trp Lys Lys Glu Pro Met Val His Leu Leu Pro His Trp Asn Trp Lys
    610                 615                 620
Glu Gly Glu Lys Val Arg Val Leu Ala Tyr Thr Asn Ala Ser Lys Val
625                 630                 635                 640
Glu Leu Val Leu Asn Gly Glu Ser Leu Gly Glu Lys Asn Tyr Asp Asn
                    645                 650                 655
Lys Gln Thr Ser Trp Gly Ala Pro Tyr Lys Glu Thr Lys Asp Gly Lys
                660                 665                 670
Thr Tyr Leu Glu Trp Ala Val Pro Phe Lys Pro Gly Lys Leu Glu Ala
            675                 680                 685
Val Ala Lys Asp Glu Asn Gly Lys Val Ile Ala Arg Asp Gln Val Val
        690                 695                 700
Thr Ala Gly Glu Pro Ala Ser Val Arg Leu Thr Ala Asp Arg Lys Val
705                 710                 715                 720
Val Lys Ala Asp Gly Thr Asp Leu Ser Phe Ile Thr Ala Asp Ile Val
                    725                 730                 735
Asp Ser Lys Gly Ile Val Val Pro Asp Ala Asp His Leu Ile Thr Phe
                740                 745                 750
Asn Val Thr Gly Gln Gly Glu Leu Ala Gly Val Asp Asn Gly Asn Ala
            755                 760                 765
Ser Ser Val Glu Arg Tyr Lys Asp Asn Lys Arg Lys Ala Phe Ser Gly
        770                 775                 780
Lys Ala Leu Ala Ile Val Gln Ser Ser Lys Leu Ser Gly Lys Ile Thr
785                 790                 795                 800
Val His Ala Ser Val Ala Gly Leu Ser Ser Asp Ser Thr Ser Val Phe
                    805                 810                 815
Thr Val Thr Pro Ala Asp His Asp Lys Lys Ile Val Ala Gly Ile Asp
                820                 825                 830
Asp Val Asn Leu Thr Val Asp Val Asn Glu Ala Pro Lys Leu Pro Ser
            835                 840                 845
Glu Ile Lys Val Tyr Tyr Ser Asp Glu Ser Ala Ala Lys Asn Val
        850                 855                 860
Thr Trp Asp Glu Val Asp Pro Lys Gln Tyr Ser Thr Val Gly Glu Phe
865                 870                 875                 880
Thr Val Glu Gly Ser Val Glu Gly Thr Ser Leu Lys Ala Lys Ala Phe
                    885                 890                 895
Val Ile Val Lys Gly Ile Val Ala Val Lys Pro Tyr Ser Thr Ala Thr
                900                 905                 910
Lys Val Gly Val Gln Pro Val Leu Pro Glu Lys Ala Thr Leu Leu Tyr
            915                 920                 925
Ser Asp Gly Thr Thr Lys Gly Ala Thr Val Thr Trp Asp Glu Ile Pro
        930                 935                 940
Glu Asp Lys Leu Ala Lys Glu Gly Arg Phe Thr Val Glu Gly Ser Val
945                 950                 955                 960
Glu Gly Thr Asp Leu Lys Ala Asn Val Tyr Val Arg Val Thr Asn Glu
                    965                 970                 975
Val Lys Ser Val Asn Ile Met Leu Gln Glu Gln Gly Ser Ala Tyr Pro
                980                 985                 990
Lys Leu Glu Ala Thr Phe Thr Asn  Pro Ala Asp Asn Leu  Gln His Leu
            995                 1000                1005
Asn Asp  Gly Ile Lys Ser Tyr  Thr Asn Asn Pro Val  Asn Arg Trp
         1010                 1015                1020
Thr Asn  Trp Thr Arg Thr Pro  Arg Asp Ala Gly Asp  Ser Ile Thr
```

Val Asn Phe Gly Lys Lys His Val Ile Asn Asn Leu Asp Leu Phe
1040              1045                  1050

Val Phe Thr Asp Ser Gly Thr Val Val Pro Glu Lys Ala Glu Val
1055              1060                  1065

Gln Tyr Trp Asp Gly Thr Ala Trp Lys Asp Val Glu Asn Leu Thr
1070              1075                  1080

Gln Pro Ser Pro Tyr Val Val Glu Lys Asn Glu Leu Thr Phe Asp
1085              1090                  1095

Ala Val Ala Thr Glu Lys Leu Lys Phe His Leu Thr Pro Ser Val
1100              1105                  1110

Lys Gly Lys Phe Leu Ala Leu Thr Glu Ala Glu Val Tyr Ala Asp
1115              1120                  1125

Gln Ile Val Met Gly Glu Thr Ala Lys Leu Gln Ser Ile Thr Val
1130              1135                  1140

Asn Gly Lys Ala Leu Glu Gly Phe Asp His Ala Lys Lys Asn Tyr
1145              1150                  1155

Glu Leu Val Leu Pro Tyr Gly Ser Glu Leu Pro Lys Ile Glu Ala
1160              1165                  1170

Ala Ala Ala Asp Asn Ala Thr Val Thr Ile Leu Pro Ala Phe Ser
1175              1180                  1185

Tyr Pro Gly Thr Ala Lys Leu Phe Val Thr Ser Glu Asp Gly Lys
1190              1195                  1200

Val Thr Thr Glu Tyr Ser Ile Gly Val Ser Thr Glu Glu Pro Lys
1205              1210                  1215

Leu Val Ser Ala
1220

<210> SEQ ID NO 11
<211> LENGTH: 2463
<212> TYPE: DNA
<213> ORGANISM: Artificial Sequence
<220> FEATURE:
<223> OTHER INFORMATION: The sequence is synthesized

<400> SEQUENCE: 11
atgagcaaaa cgacgagcgc cgccggcaac agcgtcagct atgacggcga acgccgcgtc       60
aactttaacg aaaactggcg cttttcagcgc gaaacgaacg gcagcatcgc cggcgcccag     120
aacccaggct tgacgacag cagctggcgc aaactgaacc tgccgcatga ctggagcatc       180
gaactggact ttaacaaaaa cagcctggcc acgcatgaag gcggctatct ggacggcggc     240
atcggctggt atcgcaaaac gtttacgatc ccggaaagca tgaaaggcaa acgcatcagc     300
ctggactttg acggcgtcta tatgaacagc acgacgtatc tgaacggcga agtcctgggc     360
acgtatccgt ttggctataa cgcctttagc tatgacatca gcgacaaact gtataaagac     420
ggccgcgcca cgtcctggt cgtcaaagtc aacaacacgc agccgagcag ccgctggtat     480
agcggcagcg gcatctatcg caacgtctat ctgacggtca cggacccgat ccatgtcgcc     540
cgctatggca cgtttgtcac gacgccgaac ctggaaaaaa gcatcaaaga agaccgcgcc     600
gacgtcaaca tcaaaacgaa aatcagcaac gacgccgccg aagccaaaca ggtcaaaatc     660
aaaagcacga tctatgacgg cgccggcaac acggtccaga cggtcgaaac ggaagaaaaa     720
acggccgccg ccggcacggt cacgccgttt gaacagaaca cggtcatcaa acagccgaaa     780
ctgtggagca tcgacaaacc gtatcgctat aacctggtca cggaagtcat cgtcggcggc     840

-continued

| | |
|---|---|
| cagacggtcg acacgtatga aacgaaattt ggcgtccgct attttaaatt tgacgaaaac | 900 |
| gaaggcttta gcctgaacgg cgaatatatg aaactgcatg gcgtcagcat gcatcatgac | 960 |
| ctgggcgccc tgggcgccgc cacgaacgcc cgcggcgtcg aacgccagat gcagatcatg | 1020 |
| aaagacatgg gcgtcaacgc catccgcgtc acgcataacc cggccagccc ggaactgctg | 1080 |
| gaagccgcca acaaactggg cctgtttatc atcgaagaag cctttgacag ctgggcccag | 1140 |
| agcaaaaaac cgtatgacta tggccgcttt tttaacgcct gggccgaaca tgacatcaaa | 1200 |
| gaaatggtcg accgcggcaa aaacgaaccg gccatcatca tgtggagcat cggcaacgaa | 1260 |
| atctatgaca cgacgaacgc cgccggcgtc gaaacggccc gcaacctggt cggctgggtc | 1320 |
| aaagaaatcg acacgacgcg cccgacgacg atcggcgaag acaaaacgcg cggcgacaaa | 1380 |
| gtcaacgtca cgccgatcaa cagctatatc aaagaaatct taacatcgt cgacgtcgtc | 1440 |
| ggcctgaact atagcgaaaa caactatgac ggctatcata acagaaccc gagctggaaa | 1500 |
| ctgtatggca cgaaacgag cagcgccacg cgcagccgcg cgtctatac gcatccgtat | 1560 |
| cagtataacc agagcacgaa atatgccgac ctgcagcaga gcagctatga caacgactat | 1620 |
| gtcggctggg gccgcacggc cgaagacgcc tggaaatatg accgcgacct gaaacatatc | 1680 |
| gccgccagt ttatctggac gggctttgac tatatcggcg aaccgacgcc gtattataac | 1740 |
| agctatccgg ccaaaagcag ctattttggc gccgtcgaca cggccggctt tccgaaagac | 1800 |
| atcttttatt attatcagag ccagtggaaa aagaaccga tggtccatct gctgccgcat | 1860 |
| tggaactgga agaaggcga aaaagtccgc gtcctggcct atacgaacgc cagcaaagtc | 1920 |
| gaactggtcc tgaacggcga aagcctgggc gaaaaaaact atgacaacaa acagacgagc | 1980 |
| tggggcgccc cgtataaaga aacgaaagac ggcaaaacgt atctggaatg gccgtcccg | 2040 |
| tttaaaccgg gcaaactgga agccgtcgcc aaagacgaaa acggcaaagt catcgcccgc | 2100 |
| gaccaggtcg tcacggccgg cgaaccggcc agcgtccgcc tgacggccga ccgcaaagtc | 2160 |
| gtcaaagccg acggcacgga cctgagcttt atcacggccg acatcgtcga cagcaaaggc | 2220 |
| atcgtcgtcc cggacgccga ccatctgatc acgtttaacg tcacgggcca gggcgaactg | 2280 |
| gccggcgtcg acaacggcaa cgccagcagc gtcgaacgct ataaagacaa caaacgcaaa | 2340 |
| gcctttagcg gcaaagccct ggccatcgtc cagagcagca aactgagcgg caaaatcacg | 2400 |
| gtccatgcca gcgtcgccgg cctgagcagc gacagcacga gcgtctttac ggtcacgccg | 2460 |
| taa | 2463 |

<210> SEQ ID NO 12
<211> LENGTH: 820
<212> TYPE: PRT
<213> ORGANISM: Artificial Sequence
<220> FEATURE:
<223> OTHER INFORMATION: The sequence is synthesized

<400> SEQUENCE: 12

Met Ser Lys Thr Thr Ser Ala Ala Gly Asn Ser Val Ser Tyr Asp Gly
1               5                   10                  15

Glu Arg Arg Val Asn Phe Asn Glu Asn Trp Arg Phe Gln Arg Glu Thr
            20                  25                  30

Asn Gly Ser Ile Ala Gly Ala Gln Asn Pro Gly Phe Asp Asp Ser Ser
        35                  40                  45

Trp Arg Lys Leu Asn Leu Pro His Asp Trp Ser Ile Glu Leu Asp Phe
    50                  55                  60

Asn Lys Asn Ser Leu Ala Thr His Glu Gly Gly Tyr Leu Asp Gly Gly

-continued

```
                65                  70                  75                  80

Ile Gly Trp Tyr Arg Lys Thr Phe Thr Ile Pro Glu Ser Met Lys Gly
                    85                  90                  95

Lys Arg Ile Ser Leu Asp Phe Asp Gly Val Tyr Met Asn Ser Thr Thr
                100                 105                 110

Tyr Leu Asn Gly Glu Val Leu Gly Thr Tyr Pro Phe Gly Tyr Asn Ala
            115                 120                 125

Phe Ser Tyr Asp Ile Ser Asp Lys Leu Tyr Lys Asp Gly Arg Ala Asn
        130                 135                 140

Val Leu Val Val Lys Val Asn Asn Thr Gln Pro Ser Ser Arg Trp Tyr
145                 150                 155                 160

Ser Gly Ser Gly Ile Tyr Arg Asn Val Tyr Leu Thr Val Thr Asp Pro
                165                 170                 175

Ile His Val Ala Arg Tyr Gly Thr Phe Val Thr Thr Pro Asn Leu Glu
                180                 185                 190

Lys Ser Ile Lys Glu Asp Arg Ala Asp Val Asn Ile Lys Thr Lys Ile
            195                 200                 205

Ser Asn Asp Ala Ala Glu Ala Lys Gln Val Lys Ile Lys Ser Thr Ile
        210                 215                 220

Tyr Asp Gly Ala Gly Asn Thr Val Gln Thr Val Glu Thr Glu Glu Lys
225                 230                 235                 240

Thr Ala Ala Gly Thr Val Thr Pro Phe Glu Gln Asn Thr Val Ile
                245                 250                 255

Lys Gln Pro Lys Leu Trp Ser Ile Asp Lys Pro Tyr Arg Tyr Asn Leu
                260                 265                 270

Val Thr Glu Val Ile Val Gly Gly Gln Thr Val Asp Thr Tyr Glu Thr
            275                 280                 285

Lys Phe Gly Val Arg Tyr Phe Lys Phe Asp Glu Asn Glu Gly Phe Ser
        290                 295                 300

Leu Asn Gly Glu Tyr Met Lys Leu His Gly Val Ser Met His His Asp
305                 310                 315                 320

Leu Gly Ala Leu Gly Ala Ala Thr Asn Ala Arg Gly Val Glu Arg Gln
                325                 330                 335

Met Gln Ile Met Lys Asp Met Gly Val Asn Ala Ile Arg Val Thr His
            340                 345                 350

Asn Pro Ala Ser Pro Glu Leu Leu Glu Ala Ala Asn Lys Leu Gly Leu
        355                 360                 365

Phe Ile Ile Glu Glu Ala Phe Asp Ser Trp Ala Gln Ser Lys Lys Pro
370                 375                 380

Tyr Asp Tyr Gly Arg Phe Phe Asn Ala Trp Ala Glu His Asp Ile Lys
385                 390                 395                 400

Glu Met Val Asp Arg Gly Lys Asn Glu Pro Ala Ile Ile Met Trp Ser
                405                 410                 415

Ile Gly Asn Glu Ile Tyr Asp Thr Thr Asn Ala Ala Gly Val Glu Thr
            420                 425                 430

Ala Arg Asn Leu Val Gly Trp Val Lys Glu Ile Asp Thr Thr Arg Pro
        435                 440                 445

Thr Thr Ile Gly Glu Asp Lys Thr Arg Gly Asp Lys Val Asn Val Thr
450                 455                 460

Pro Ile Asn Ser Tyr Ile Lys Glu Ile Phe Asn Ile Val Asp Val Val
465                 470                 475                 480

Gly Leu Asn Tyr Ser Glu Asn Asn Tyr Asp Gly Tyr His Lys Gln Asn
                485                 490                 495
```

Pro Ser Trp Lys Leu Tyr Gly Ser Glu Thr Ser Ser Ala Thr Arg Ser
            500                 505                 510

Arg Gly Val Tyr Thr His Pro Tyr Gln Tyr Asn Gln Ser Thr Lys Tyr
        515                 520                 525

Ala Asp Leu Gln Gln Ser Ser Tyr Asp Asn Asp Tyr Val Gly Trp Gly
    530                 535                 540

Arg Thr Ala Glu Asp Ala Trp Lys Tyr Asp Arg Asp Leu Lys His Ile
545                 550                 555                 560

Ala Gly Gln Phe Ile Trp Thr Gly Phe Asp Tyr Ile Gly Glu Pro Thr
                565                 570                 575

Pro Tyr Tyr Asn Ser Tyr Pro Ala Lys Ser Ser Tyr Phe Gly Ala Val
                580                 585                 590

Asp Thr Ala Gly Phe Pro Lys Asp Ile Phe Tyr Tyr Tyr Gln Ser Gln
            595                 600                 605

Trp Lys Lys Glu Pro Met Val His Leu Leu Pro His Trp Asn Trp Lys
        610                 615                 620

Glu Gly Glu Lys Val Arg Val Leu Ala Tyr Thr Asn Ala Ser Lys Val
625                 630                 635                 640

Glu Leu Val Leu Asn Gly Glu Ser Leu Gly Glu Lys Asn Tyr Asp Asn
                645                 650                 655

Lys Gln Thr Ser Trp Gly Ala Pro Tyr Lys Glu Thr Lys Asp Gly Lys
            660                 665                 670

Thr Tyr Leu Glu Trp Ala Val Pro Phe Lys Pro Gly Lys Leu Glu Ala
        675                 680                 685

Val Ala Lys Asp Glu Asn Gly Lys Val Ile Ala Arg Asp Gln Val Val
    690                 695                 700

Thr Ala Gly Glu Pro Ala Ser Val Arg Leu Thr Ala Asp Arg Lys Val
705                 710                 715                 720

Val Lys Ala Asp Gly Thr Asp Leu Ser Phe Ile Thr Ala Asp Ile Val
                725                 730                 735

Asp Ser Lys Gly Ile Val Val Pro Asp Ala Asp His Leu Ile Thr Phe
            740                 745                 750

Asn Val Thr Gly Gln Gly Glu Leu Ala Gly Val Asp Asn Gly Asn Ala
        755                 760                 765

Ser Ser Val Glu Arg Tyr Lys Asp Asn Lys Arg Lys Ala Phe Ser Gly
    770                 775                 780

Lys Ala Leu Ala Ile Val Gln Ser Ser Lys Leu Ser Gly Lys Ile Thr
785                 790                 795                 800

Val His Ala Ser Val Ala Gly Leu Ser Ser Asp Ser Thr Ser Val Phe
                805                 810                 815

Thr Val Thr Pro
            820

<210> SEQ ID NO 13
<211> LENGTH: 5132
<212> TYPE: DNA
<213> ORGANISM: Artificial Sequence
<220> FEATURE:
<223> OTHER INFORMATION: The sequence is synthesized

<400> SEQUENCE: 13
atgaaaagta caaccagtgc agccggtaaa tccgttagtt ataacgacgg agagcgtaga      60
gtgaattttg agaattggcg gttccaacgc gagacgaatg gcagtattgc aggtgcgcag     120
aacccaggtt ttgatgattc atcatggaga aaacttaatc tgccgcatga atggtctatc     180

```
gatttagact ttaataaaaa cagtttggct acgcatgaag gaggttacct tgatggggga      240
attggctgga atagaaaaac gtttacaatt ccggagtcga tgaaagggaa gcggttttct      300
ttggactttg atggtgtcta catgaactcc actacctacc ttaacggtga agttttgggt      360
acttacccat tcggatacaa cgccttctct tacgacattt ccgacaagtt gtacaaagat      420
ggcagagcaa acgtgttggt cgtcaaagtt aacacgaatc agcctagcgg acgctggtat      480
agcggatcat caatttatag aaacgtctat cttacggtga ccgacccgat ccatgtggcg      540
agatacggca cgtttgtaac aacaccaaat ctggaaaaaa gtatcaagga agaccgggat      600
gcagttaaca ttaaaacgaa gatcagcaac gcagaagcca agcaagtcaa aatcgctatt      660
aagtctacta tctacgatgg tgctggtaac accgtccaaa ctgttgaaac cgaggaaaag      720
acagcagctg ctggtacagt cactccattc gagcagaaca ccgttattaa gcaacctaag      780
ttgtggtcca tcgacaaacc atacagatac aacttggtca ctgaagttat tgtaggaggt      840
cagacggtcg atacatatga gacgaagttt ggagtccggt acttcaaatt tgatgaaaac      900
gaaggctatt cattgaacgg tgaatttatg aaactccacg gagtctcgat gcatcacgat      960
ttggctggag gtgcggcgct tacaaatgca agaggcgtcg aaagacaaat gcaaattatg     1020
aaggatgttg gagtcaacgc gattagagtt acgcataacc ctgcttcacc agaattaggc     1080
ttagaatttg cggccaacaa attattaatc attgaggagg catttgattc ttgggcgcag     1140
tctaaaaaac cgtatgacta tggccgcttt tttaatgctt gggctgagca tgatattaag     1200
gaaatggtcg atagaggtaa aaacgaacct gcgatcataa tgtggagcat aggaaacgag     1260
atatatgaca ctactaatgc agctggagtt gagactgctc gaaatctcgt tggctgggta     1320
aaagaaatcg acacaacgcc gagagccaca attggggaag ataaaacccg aggagataat     1380
gtgacaccga ttaactcata tattaaagaa atcttcaaca ttgtggacgt cgttggtctc     1440
aactactccg aaaacaacta cgatggatac cacaagcaga acccatcttg aagttgtac     1500 ggttccgaga ccagttccgc tactagatcc agaggtgtct acacccatcc ttaccaatac     1560
aaccatgata caaaatatgc ggatttgcag cagtcttcgt atgacaatga ttatgttgga     1620
tggggtagaa cagcacagga tgcttggaaa tatgatcgtg atcttaaaca tattgcaggt     1680
caatttattt ggacaggctt cgattatatt ggagaaccaa caccgtatta taactcatac     1740
ccggcaaaaa gctcatattt cggagcagtt gacacgcgcg ggttccctaa agacattttc     1800
tattattacc aaagccagtg gaaaaagaa cctatggttc accttttgcc gcactggaac     1860
tggaaagagg gagagaaggt tcgggtattg gcgtatacca atgcgagcaa agttgaactt     1920
gtgctgaatg gagaatcact cggcaacgaa aagtatgata caagcaaac tagttggggt     1980 gcgccgtaca aagaaacaaa agatggtaaa acatacttag aatgggcagt cccattcaag     2040
cctggaaagt tggaagctgt tgccaaggat gagaatggta aggtcattgc aagagatcaa     2100
gttgtcaccg ctggtgaacc agcctccgtt agattgactg ctgacagaaa ggtcgttaag     2160
gctgatggta ctgacttgtc gttcatcact gctgacattg tcgactccaa aggcatcgtc     2220
gtcccggacg cagatcatct gattacgttt aacgtgacag gacagggtga acttgcgggg     2280
gttgataatg gtaatgcgtc ttcagttgaa cgctacaaag ataataaaag aaaggcattt     2340
tcggggaaag cgttggccat cgtgcagagc tcaaaactga gcggcaagat aaccgtacat     2400
gcatctgtgg ctggcttaag ctccgatagc acatccgtgt tcactgtaac ccctgccgat     2460
cacgataaga aaatcgtggc cggaattgat gacgtgaatc tgacggttga tgtcaatgaa     2520
```

```
gcccctaagc ttccgagcga gattaaggtc tattactccg atgaatcagc cgcggctaaa    2580
aacgttacat gggatgaagt tgatcctaag caatatagca ccgtcggcga gtttacagtc    2640
gaagggtctg tcgaaggtac aagcttaaaa gctaaagcat tcgtaattgt taagggaatt    2700
gtcgctgtca agccgtactc gactgccaca aaggtaggag tccagccggt cttacctgaa    2760
aaagcgaccc tgctttattc agacggcaca accaaaggcg cgacagtgac atgggacgag    2820
ctgcctgagg ataagcttgc taaagagggt cggttcaccg tggaaggctc ggtagaaggc    2880
accgatttaa aagcaaatgt ctacgttcgc gtgactaacg aagttaaatc agtcaatatt    2940
atgcttcaag aacaaggatc agcttatcca aagttagagg ctacatttac gaatcctgcg    3000
gataaccttc aacatctgaa cgacggcatt aagagttata cgaataacca ggtgaaccgc    3060
tggacaaatt ggactagaac cccaagagac gctggtgaca gcatcacagt gaattttggc    3120
aagaagcacg tcattaacaa cttggacttg ttcgttttca ccgactctgg tactgtcgtt    3180
cctgagaagg ctgaagtcca gtactgggat ggtactgcct ggaaagacgt tgagaacttg    3240
actcaaccat ccccatacgt cgttgaaaag aacgagttga ccttcgatgc tgtcgctact    3300
gaaaagttga agttccactt gacaccttct gttaagggaa agttcctcgc cctgaccgaa    3360
gccgaggtgt atgcggacca gatcgttgat ggggaaacag cgaaacttca atctattacc    3420
gtgaacggca aagccttgga gggttttgat catgcaaaga aaaactatga attggtcctc    3480
ccgtacggat cggagctccc gaagatagaa gcagcggctg ccgataatgc gaccgtgaca    3540
attttgccag cattcagcta tccgggcacg gctaaattat ttgtcacgag tgaagatgga    3600
aaggtgacca ctgaatattc tatcggggta tctactgaag aaccaaaatt agtgagcgcg    3660
gaattaagtg cggataaaac gaacgttatg gaagacgata ttattgatct taaggtgatt    3720 ggtcttttg aatctaagga aaaaattgat gtgacagact cacaaccaac atacgaattt    3780
gatcagcaga ttattaagat tgaaggaaac aaactgtatg ctttggagac cggcaatgtg    3840
aaagtcaagg ttacagttac atataaaggc gtctcagtta caacgccggc tcttgagttt    3900
acaatagcta aacaccctgc gccaaaatat atcacatcac tggaacctgt tacggtggtt    3960
gttaaaaaag gtgaggcgcc agaactgcct gctactgtcg tagcgcacta taatcggggc    4020
attccgcgcg acgtaaaagt gaaatgggag cgtattcatc cttcaaaata tcaacaactg    4080
ggggagttca cagtatcagg aatggtcgaa ggtactgaca ttaaagctca agccaaagta    4140
gcggtcaaag gagcggtcat cgtagaagat attagaatgg cagttctttt gaaacagatg    4200
ccacaattac cggaaaagt tactgtctat tactctgacg gagccgagga gcaacgggcc    4260
gttaaatggg aagaaattcc acaggaagag ctggagaaag taggagagtt caaagtcaat    4320
ggtgatgtta atggcgttaa attaaaggcc actgctacaa tacgggtgac tgacgaggtc    4380
ggagctgaac aaaacataag ccgggcgaaa aacggctatg aatacccgaa agccgaagca    4440
tcctttacga atgatggtcc gggctcctcc gatagaatcg aggccattaa cgacgacgtc    4500
atctcttacg aagccaaccc acacaacaga tggaccaact ggcaacctgt tccaagagct    4560
ggtgactggg tatccattac cttcggtgac tacgagccaa ccgaatacga cgttgactct    4620
atggagatcc actggttcgc tgaccacggt acttcctacc ctgaacgttt tcaaattgaa    4680
tataaatcag gagactcctg gaaagaagta acaagcctga aaagtgaccc agcttcccca    4740
gctttaggga aagctaatgt gtactcgttt gatcgcgtta agacgtcagc cattcgggta    4800
aaaatgacag cgcaggcagg taaagtctg gccattaccg aacttaaagt ttttagcaaa    4860
tggccgaaag ccggaacaga acctgatgtt acagatatta agtgggtgg aaaatccata    4920
```

```
ctggaagagt tcgaacaaga aggagaccat tatgaagcaa cgatagatgt gggcgacgcg    4980
aacgtgatgc ctaaaattta tgttaaggcg aaagaccaaa caagcatctc aatcgttccg    5040
gctgtaacga gcgtcagcac cgctaaggtg atcgcagagg acggagacgg taaaaaagtg    5100
aaggtttatt cgatccataa gagctacaat aa                                  5132
```

<210> SEQ ID NO 14
<211> LENGTH: 1709
<212> TYPE: PRT
<213> ORGANISM: Artificial Sequence
<220> FEATURE:
<223> OTHER INFORMATION: The sequence is synthesized

<400> SEQUENCE: 14

```
Met Lys Ser Thr Thr Ser Ala Ala Gly Lys Ser Val Ser Tyr Asn Asp
1               5                   10                  15

Gly Glu Arg Arg Val Asn Phe Glu Asn Trp Arg Phe Gln Arg Glu Thr
            20                  25                  30

Asn Gly Ser Ile Ala Gly Ala Gln Asn Pro Gly Phe Asp Asp Ser Ser
        35                  40                  45

Trp Arg Lys Leu Asn Leu Pro His Glu Trp Ser Ile Asp Leu Asp Phe
    50                  55                  60

Asn Lys Asn Ser Leu Ala Thr His Glu Gly Gly Tyr Leu Asp Gly Gly
65                  70                  75                  80

Ile Gly Trp Asn Arg Lys Thr Phe Thr Ile Pro Glu Ser Met Lys Gly
                85                  90                  95

Lys Arg Phe Ser Leu Asp Phe Asp Gly Val Tyr Met Asn Ser Thr Thr
            100                 105                 110

Tyr Leu Asn Gly Glu Val Leu Gly Thr Tyr Pro Phe Gly Tyr Asn Ala
        115                 120                 125

Phe Ser Tyr Asp Ile Ser Asp Lys Leu Tyr Lys Asp Gly Arg Ala Asn
    130                 135                 140

Val Leu Val Val Lys Val Asn Thr Asn Gln Pro Ser Gly Arg Trp Tyr
145                 150                 155                 160

Ser Gly Ser Ser Ile Tyr Arg Asn Val Tyr Leu Thr Val Thr Asp Pro
                165                 170                 175

Ile His Val Ala Arg Tyr Gly Thr Phe Val Thr Thr Pro Asn Leu Glu
            180                 185                 190

Lys Ser Ile Lys Glu Asp Arg Asp Ala Val Asn Ile Lys Thr Lys Ile
        195                 200                 205

Ser Asn Ala Glu Ala Lys Gln Val Lys Ile Ala Ile Lys Ser Thr Ile
    210                 215                 220

Tyr Asp Gly Ala Gly Asn Thr Val Gln Thr Val Glu Thr Glu Glu Lys
225                 230                 235                 240

Thr Ala Ala Ala Gly Thr Val Thr Pro Phe Glu Gln Asn Thr Val Ile
                245                 250                 255

Lys Gln Pro Lys Leu Trp Ser Ile Asp Lys Pro Tyr Arg Tyr Asn Leu
            260                 265                 270

Val Thr Glu Val Ile Val Gly Gly Gln Thr Val Asp Thr Tyr Glu Thr
        275                 280                 285

Lys Phe Gly Val Arg Tyr Phe Lys Phe Asp Glu Asn Glu Gly Tyr Ser
    290                 295                 300

Leu Asn Gly Glu Phe Met Lys Leu His Gly Val Ser Met His His Asp
305                 310                 315                 320
```

-continued

Leu Ala Gly Gly Ala Ala Leu Thr Asn Ala Arg Gly Val Glu Arg Gln
            325                 330                 335

Met Gln Ile Met Lys Asp Val Gly Val Asn Ala Ile Arg Val Thr His
            340                 345                 350

Asn Pro Ala Ser Pro Glu Leu Gly Leu Glu Phe Ala Ala Asn Lys Leu
            355                 360                 365

Leu Ile Ile Glu Glu Ala Phe Asp Ser Trp Ala Gln Ser Lys Lys Pro
        370                 375                 380

Tyr Asp Tyr Gly Arg Phe Phe Asn Ala Trp Ala Glu His Asp Ile Lys
385                 390                 395                 400

Glu Met Val Asp Arg Gly Lys Asn Glu Pro Ala Ile Ile Met Trp Ser
                405                 410                 415

Ile Gly Asn Glu Ile Tyr Asp Thr Thr Asn Ala Ala Gly Val Glu Thr
            420                 425                 430

Ala Arg Asn Leu Val Gly Trp Val Lys Glu Ile Asp Thr Thr Pro Arg
        435                 440                 445

Ala Thr Ile Gly Glu Asp Lys Thr Arg Gly Asp Asn Val Thr Pro Ile
    450                 455                 460

Asn Ser Tyr Ile Lys Glu Ile Phe Asn Ile Val Asp Val Val Gly Leu
465                 470                 475                 480

Asn Tyr Ser Glu Asn Asn Tyr Asp Gly Tyr His Lys Gln Asn Pro Ser
                485                 490                 495

Trp Lys Leu Tyr Gly Ser Glu Thr Ser Ala Thr Arg Ser Arg Gly
            500                 505                 510

Val Tyr Thr His Pro Tyr Gln Tyr Asn His Asp Thr Lys Tyr Ala Asp
        515                 520                 525

Leu Gln Gln Ser Ser Tyr Asp Asn Asp Tyr Val Gly Trp Gly Arg Thr
    530                 535                 540

Ala Gln Asp Ala Trp Lys Tyr Asp Arg Asp Leu Lys His Ile Ala Gly
545                 550                 555                 560

Gln Phe Ile Trp Thr Gly Phe Asp Tyr Ile Gly Glu Pro Thr Pro Tyr
                565                 570                 575

Tyr Asn Ser Tyr Pro Ala Lys Ser Ser Tyr Phe Gly Ala Val Asp Thr
            580                 585                 590

Ala Gly Phe Pro Lys Asp Ile Phe Tyr Tyr Tyr Gln Ser Gln Trp Lys
        595                 600                 605

Lys Glu Pro Met Val His Leu Leu Pro His Trp Asn Trp Lys Glu Gly
    610                 615                 620

Glu Lys Val Arg Val Leu Ala Tyr Thr Asn Ala Ser Lys Val Glu Leu
625                 630                 635                 640

Val Leu Asn Gly Glu Ser Leu Gly Asn Glu Lys Tyr Asp Asn Lys Gln
                645                 650                 655

Thr Ser Trp Gly Ala Pro Tyr Lys Glu Thr Lys Asp Gly Lys Thr Tyr
            660                 665                 670

Leu Glu Trp Ala Val Pro Phe Lys Pro Gly Lys Leu Glu Ala Val Ala
        675                 680                 685

Lys Asp Glu Asn Gly Lys Val Ile Ala Arg Asp Gln Val Val Thr Ala
    690                 695                 700

Gly Glu Pro Ala Ser Val Arg Leu Thr Ala Asp Arg Lys Val Val Lys
705                 710                 715                 720

Ala Asp Gly Thr Asp Leu Ser Phe Ile Thr Ala Asp Ile Val Asp Ser
                725                 730                 735

Lys Gly Ile Val Val Pro Asp Ala Asp His Leu Ile Thr Phe Asn Val

-continued

```
                740                 745                 750
Thr Gly Gln Gly Glu Leu Ala Gly Val Asp Asn Gly Asn Ala Ser Ser
                755                 760                 765
Val Glu Arg Tyr Lys Asp Asn Lys Arg Lys Ala Phe Ser Gly Lys Ala
                770                 775                 780
Leu Ala Ile Val Gln Ser Ser Lys Leu Ser Gly Lys Ile Thr Val His
785                 790                 795                 800
Ala Ser Val Ala Gly Leu Ser Ser Asp Ser Thr Ser Val Phe Thr Val
                805                 810                 815
Thr Pro Ala Asp His Asp Lys Lys Ile Val Ala Gly Ile Asp Asp Val
                820                 825                 830
Asn Leu Thr Val Asp Val Asn Glu Ala Pro Lys Leu Pro Ser Glu Ile
                835                 840                 845
Lys Val Tyr Tyr Ser Asp Glu Ser Ala Ala Ala Lys Asn Val Thr Trp
                850                 855                 860
Asp Glu Val Asp Pro Lys Gln Tyr Ser Thr Val Gly Glu Phe Thr Val
865                 870                 875                 880
Glu Gly Ser Val Glu Gly Thr Ser Leu Lys Ala Lys Ala Phe Val Ile
                885                 890                 895
Val Lys Gly Ile Val Ala Val Lys Pro Tyr Ser Thr Ala Thr Lys Val
                900                 905                 910
Gly Val Gln Pro Val Leu Pro Glu Lys Ala Thr Leu Leu Tyr Ser Asp
                915                 920                 925
Gly Thr Thr Lys Gly Ala Thr Val Thr Trp Asp Glu Leu Pro Glu Asp
                930                 935                 940
Lys Leu Ala Lys Glu Gly Arg Phe Thr Val Glu Gly Ser Val Glu Gly
945                 950                 955                 960
Thr Asp Leu Lys Ala Asn Val Tyr Val Arg Val Thr Asn Glu Val Lys
                965                 970                 975
Ser Val Asn Ile Met Leu Gln Glu Gln Gly Ser Ala Tyr Pro Lys Leu
                980                 985                 990
Glu Ala Thr Phe Thr Asn Pro Ala Asp Asn Leu Gln His Leu Asn Asp
                995                1000                1005
Gly Ile Lys Ser Tyr Thr Asn Asn Gln Val Asn Arg Trp Thr Asn
                1010                1015                1020
Trp Thr Arg Thr Pro Arg Asp Ala Gly Asp Ser Ile Thr Val Asn
                1025                1030                1035
Phe Gly Lys Lys His Val Ile Asn Asn Leu Asp Leu Phe Val Phe
                1040                1045                1050
Thr Asp Ser Gly Thr Val Val Pro Glu Lys Ala Glu Val Gln Tyr
                1055                1060                1065
Trp Asp Gly Thr Ala Trp Lys Asp Val Glu Asn Leu Thr Gln Pro
                1070                1075                1080
Ser Pro Tyr Val Val Glu Lys Asn Glu Leu Thr Phe Asp Ala Val
                1085                1090                1095
Ala Thr Glu Lys Leu Lys Phe His Leu Thr Pro Ser Val Lys Gly
                1100                1105                1110
Lys Phe Leu Ala Leu Thr Glu Ala Glu Val Tyr Ala Asp Gln Ile
                1115                1120                1125
Val Asp Gly Glu Thr Ala Lys Leu Gln Ser Ile Thr Val Asn Gly
                1130                1135                1140
Lys Ala Leu Glu Gly Phe Asp His Ala Lys Lys Asn Tyr Glu Leu
                1145                1150                1155
```

-continued

Val Leu Pro Tyr Gly Ser Glu Leu Pro Lys Ile Glu Ala Ala Ala
1160            1165            1170

Ala Asp Asn Ala Thr Val Thr Ile Leu Pro Ala Phe Ser Tyr Pro
1175            1180            1185

Gly Thr Ala Lys Leu Phe Val Thr Ser Glu Asp Gly Lys Val Thr
1190            1195            1200

Thr Glu Tyr Ser Ile Gly Val Ser Thr Glu Glu Pro Lys Leu Val
1205            1210            1215

Ser Ala Glu Leu Ser Ala Asp Lys Thr Asn Val Met Glu Asp Asp
1220            1225            1230

Ile Ile Asp Leu Lys Val Ile Gly Leu Phe Glu Ser Lys Glu Lys
1235            1240            1245

Ile Asp Val Thr Asp Ser Gln Pro Thr Tyr Glu Phe Asp Gln Gln
1250            1255            1260

Ile Ile Lys Ile Glu Gly Asn Lys Leu Tyr Ala Leu Glu Thr Gly
1265            1270            1275

Asn Val Lys Val Lys Val Thr Val Thr Tyr Lys Gly Val Ser Val
1280            1285            1290

Thr Thr Pro Ala Leu Glu Phe Thr Ile Ala Lys His Pro Ala Pro
1295            1300            1305

Lys Tyr Ile Thr Ser Leu Glu Pro Val Thr Val Val Lys Lys
1310            1315            1320

Gly Glu Ala Pro Glu Leu Pro Ala Thr Val Val Ala His Tyr Asn
1325            1330            1335

Arg Gly Ile Pro Arg Asp Val Lys Val Lys Trp Glu Arg Ile His
1340            1345            1350

Pro Ser Lys Tyr Gln Gln Leu Gly Glu Phe Thr Val Ser Gly Met
1355            1360            1365

Val Glu Gly Thr Asp Ile Lys Ala Gln Ala Lys Val Ala Val Lys
1370            1375            1380

Gly Ala Val Ile Val Glu Asp Ile Arg Met Ala Val Leu Leu Lys
1385            1390            1395

Gln Met Pro Gln Leu Pro Gly Lys Val Thr Val Tyr Tyr Ser Asp
1400            1405            1410

Gly Ala Glu Glu Gln Arg Ala Val Lys Trp Glu Ile Pro Gln
1415            1420            1425

Glu Glu Leu Glu Lys Val Gly Glu Phe Lys Val Asn Gly Asp Val
1430            1435            1440

Asn Gly Val Lys Leu Lys Ala Thr Ala Thr Ile Arg Val Thr Asp
1445            1450            1455

Glu Val Gly Ala Glu Gln Asn Ile Ser Arg Ala Lys Asn Gly Tyr
1460            1465            1470

Glu Tyr Pro Lys Ala Glu Ala Ser Phe Thr Asn Asp Gly Pro Gly
1475            1480            1485

Ser Ser Asp Arg Ile Glu Ala Ile Asn Asp Asp Val Ile Ser Tyr
1490            1495            1500

Glu Ala Asn Pro His Asn Arg Trp Thr Asn Trp Gln Pro Val Pro
1505            1510            1515

Arg Ala Gly Asp Trp Val Ser Ile Thr Phe Gly Asp Tyr Glu Pro
1520            1525            1530

Thr Glu Tyr Asp Val Asp Ser Met Glu Ile His Trp Phe Ala Asp
1535            1540            1545

| His | Gly | Thr | Ser | Tyr | Pro | Glu | Arg | Phe | Gln | Ile | Glu | Tyr | Lys | Ser |
|---|---|---|---|---|---|---|---|---|---|---|---|---|---|---|
| 1550 | | | | | 1555 | | | | | 1560 | | | | |

| Gly | Asp | Ser | Trp | Lys | Glu | Val | Thr | Ser | Leu | Lys | Ser | Asp | Pro | Ala |
|---|---|---|---|---|---|---|---|---|---|---|---|---|---|---|
| 1565 | | | | | 1570 | | | | | 1575 | | | | |

| Ser | Pro | Ala | Leu | Gly | Lys | Ala | Asn | Val | Tyr | Ser | Phe | Asp | Arg | Val |
|---|---|---|---|---|---|---|---|---|---|---|---|---|---|---|
| 1580 | | | | | 1585 | | | | | 1590 | | | | |

| Lys | Thr | Ser | Ala | Ile | Arg | Val | Lys | Met | Thr | Ala | Gln | Ala | Gly | Lys |
|---|---|---|---|---|---|---|---|---|---|---|---|---|---|---|
| 1595 | | | | | 1600 | | | | | 1605 | | | | |

| Ser | Leu | Ala | Ile | Thr | Glu | Leu | Lys | Val | Phe | Ser | Lys | Trp | Pro | Lys |
|---|---|---|---|---|---|---|---|---|---|---|---|---|---|---|
| 1610 | | | | | 1615 | | | | | 1620 | | | | |

| Ala | Gly | Thr | Glu | Pro | Asp | Val | Thr | Asp | Ile | Lys | Val | Gly | Gly | Lys |
|---|---|---|---|---|---|---|---|---|---|---|---|---|---|---|
| 1625 | | | | | 1630 | | | | | 1635 | | | | |

| Ser | Ile | Leu | Glu | Glu | Phe | Glu | Gln | Glu | Gly | Asp | His | Tyr | Glu | Ala |
|---|---|---|---|---|---|---|---|---|---|---|---|---|---|---|
| 1640 | | | | | 1645 | | | | | 1650 | | | | |

| Thr | Ile | Asp | Val | Gly | Asp | Ala | Asn | Val | Met | Pro | Lys | Ile | Tyr | Val |
|---|---|---|---|---|---|---|---|---|---|---|---|---|---|---|
| 1655 | | | | | 1660 | | | | | 1665 | | | | |

| Lys | Ala | Lys | Asp | Gln | Thr | Ser | Ile | Ser | Ile | Val | Pro | Ala | Val | Thr |
|---|---|---|---|---|---|---|---|---|---|---|---|---|---|---|
| 1670 | | | | | 1675 | | | | | 1680 | | | | |

| Ser | Val | Ser | Thr | Ala | Lys | Val | Ile | Ala | Glu | Asp | Gly | Asp | Gly | Lys |
|---|---|---|---|---|---|---|---|---|---|---|---|---|---|---|
| 1685 | | | | | 1690 | | | | | 1695 | | | | |

| Lys | Val | Lys | Val | Tyr | Ser | Ile | His | Lys | Ser | Tyr |
|---|---|---|---|---|---|---|---|---|---|---|
| 1700 | | | | | 1705 | | | | | |

<210> SEQ ID NO 15
<211> LENGTH: 3669
<212> TYPE: DNA
<213> ORGANISM: Artificial Sequence
<220> FEATURE:
<223> OTHER INFORMATION: The sequence is synthesized

<400> SEQUENCE: 15

```
atgaaaagca cgacgagcgc cgccggcaaa agcgtcagct ataacgacgg cgaacgccgc      60
gtcaactttg aaaactggcg cttttcagcgc gaaacgaacg gcagcatcgc cggcgcccag    120
aacccaggct tgacgacag cagctggcgc aaactgaacc tgccgcatga atggagcatc      180
gacctggact taacaaaaa cagcctggcc acgcatgaag gcggctatct ggacggcggc      240
atcggctgga accgcaaaac gtttacgatc ccggaaagca tgaaaggcaa cgctttagc     300
ctggactttg acgcgtctta tatgaacagc acgacgtatc tgaacggcga agtcctgggc    360
acgtatccgt ttggctataa cgcctttagc tatgacatca gcacaaaact gtataaagac    420
ggccgcgcca acgtcctggt cgtcaaagtc aacacgaacc agccgagcgg ccgctggtat    480
agcggcagca gcatctatcg caacgtctat ctgacggtca cggacccgat ccatgtcgcc    540
cgctatggca cgtttgtcac gacgccgaac ctggaaaaaa gcatcaaaga agaccgcgac    600
gccgtcaaca tcaaaacgaa atcagcaac gccgaagcca acaggtcaa atcgccatc      660
aaaagcacga tctatgacgg cgccggcaac acggtccaga cggtcgaaac ggaagaaaaa    720
acggccgccg ccggcacggt cacgccgttt gaacagaaca cggtcatcaa acagccgaaa    780
ctgtggagca tcgacaaacc gtatcgctat aacctggtca cggaagtcat cgtcggcggc    840
cagacggtcg acacgtatga acgaaatt ggcgtccgct attttaaatt tgacgaaaac     900
gaaggctata gcctgaacgg cgaatttatg aaactgcatg gcgtcagcat gcatcatgac    960
ctggccggcg cgccgcccct gacgaacgcc gcggcgtcg aacgccagat gcagatcatg   1020
aaagacgtcg gcgtcaacgc catccgcgtc acgcataacc cggccagccc ggaactgggc   1080
```

```
ctggaatttg ccgccaacaa actgctgatc atcgaagaag cctttgacag ctgggcccag    1140
agcaaaaaac cgtatgacta tggccgcttt tttaacgcct gggccgaaca tgacatcaaa    1200
gaaatggtcg accgcggcaa aaacgaaccg gccatcatca tgtggagcat cggcaacgaa    1260
atctatgaca cgacgaacgc cgccggcgtc gaaacggccc gcaacctggt cggctgggtc    1320
aaagaaatcg acacgacgcc gcgcgccacg atcggcgaag acaaaacgcg cggcgacaac    1380
gtcacgccga tcaacagcta tatcaaagaa atctttaaca tcgtcgacgt cgtcggcctg    1440
aactatagcg aaaacaacta tgacggctat cataaacaga acccgagctg gaaactgtat    1500
ggcagcgaaa cgagcagcgc cacgcgcagc cgcggcgtct atacgcatcc gtatcagtat    1560
aaccatgaca cgaaatatgc cgacctgcag cagagcagct atgacaacga ctatgtcggc    1620
tggggccgca cggcccagga cgcctggaaa tatgaccgcg acctgaaaca tatcgccggc    1680
cagtttatct ggacgggctt tgactatatc ggcgaaccga cgccgtatta taacagctat    1740
ccggccaaaa gcagctattt tggcgccgtc gacacggccg gctttccgaa agacatcttt    1800
tattattatc agagccagtg gaaaaaagaa ccgatggtcc atctgctgcc gcattggaac    1860
tggaaagaag cgaaaaaagt ccgcgtcctg gcctatacga acgccagcaa agtcgaactg    1920
gtcctgaacg gcgaaagcct gggcaacgaa aaatatgaca caaacagac gagctggggc    1980 gccccgtata agaaacgaa agacggcaaa acgtatctgg aatgggccgt cccgtttaaa    2040
ccgggcaaac tggaagccgt cgccaaagac gaaaacggca agtcatcgc ccgcgaccag    2100 gtcgtcacgg ccggcgaacc ggccagcgtc cgcctgacgg ccgaccgcaa agtcgtcaaa    2160
gccgacggca cggacctgag ctttatcacg gccgacatcg tcgacagcaa aggcatcgtc    2220
gtcccggacg ccgaccatct gatcacgttt aacgtcacgg ccagggcga actggccggc    2280 gtcgacaacg gcaacgccag cagcgtcgaa cgctataaag acaacaaacg caaagccttt    2340
agcggcaaag ccctggccat cgtccagagc agcaaactga gcggcaaaat cacggtccat    2400
gccagcgtcg ccggcctgag cagcgacagc acgagcgtct ttacggtcac gccggccgac    2460
catgacaaaa aaatcgtcgc cggcatcgac gacgtcaacc tgacggtcga cgtcaacgaa    2520
gccccgaaac tgccgagcga aatcaaagtc tattatagcg acgaaagcgc cgccgccaaa    2580
aacgtcacgt gggacgaagt cgacccgaaa cagtatagca cggtcggcga atttacggtc    2640
gaaggcagcg tcgaaggcac gagcctgaaa gccaaagcct tgtcatcgt caaaggcatc    2700 gtcgccgtca accgtatag cacggccacg aaagtcggcg tccagccggt cctgccggaa    2760
aaagccacgc tgctgtatag cgacggcacg acgaaaggcg ccacggtcac gtgggacgaa    2820
ctgccggaag acaaactggc caaagaaggc cgctttacgg tcgaaggcag cgtcgaaggc    2880
acggacctga agccaacgt ctatgtccgc gtcacgaacg aagtcaaaag cgtcaacatc    2940
atgctgcagg aacagggcag cgcctatccg aaactggaag ccacgtttac gaacccggcc    3000
gacaacctgc agcatctgaa cgacggcatc aaaagctata cgaacaacca ggtcaaccgc    3060
tggacgaact ggacgcgcac gccgcgcgac ccggcgaca gcatcacggt caactttggc    3120
aaaaaacatg tcatcaacaa cctggacctg tttgtcttta cggacagcgg cacggtcgtc    3180
ccggaaaaag ccgaagtcca gtattgggac ggcacggcct ggaaagacgt cgaaaacctg    3240
acgcagccga gcccgtatgt cgtcgaaaaa aacgaactga cgtttgacgc cgtcgccacg    3300
gaaaaactga atttcatct gacgccgagc gtcaaaggca atttctggc cctgacggaa    3360 gccgaagtct atgccgacca gatcgtcgac ggcgaaacgg ccaaactgca gagcatcacg    3420
gtcaacggca agcccctgga aggctttgac catgccaaaa aaaactatga actggtcctg    3480
```

```
ccgtatggca gcgaactgcc gaaaatcgaa gccgccgccg ccgacaacgc cacggtcacg    3540
atcctgccgg cctttagcta tccgggcacg gccaaactgt tgtcacgag cgaagacggc    3600 aaagtcacga cggaatatag catcggcgtc agcacggaag aaccgaaact ggtcagcgcc    3660
gaactgtaa                                                           3669
```

<210> SEQ ID NO 16
<211> LENGTH: 1222
<212> TYPE: PRT
<213> ORGANISM: Artificial Sequence
<220> FEATURE:
<223> OTHER INFORMATION: The sequence is synthesized

<400> SEQUENCE: 16

```
Met Lys Ser Thr Thr Ser Ala Ala Gly Lys Ser Val Ser Tyr Asn Asp
1               5                   10                  15

Gly Glu Arg Arg Val Asn Phe Glu Asn Trp Arg Phe Gln Arg Glu Thr
            20                  25                  30

Asn Gly Ser Ile Ala Gly Ala Gln Asn Pro Gly Phe Asp Asp Ser Ser
        35                  40                  45

Trp Arg Lys Leu Asn Leu Pro His Glu Trp Ser Ile Asp Leu Asp Phe
    50                  55                  60

Asn Lys Asn Ser Leu Ala Thr His Glu Gly Gly Tyr Leu Asp Gly Gly
65                  70                  75                  80

Ile Gly Trp Asn Arg Lys Thr Phe Thr Ile Pro Glu Ser Met Lys Gly
                85                  90                  95

Lys Arg Phe Ser Leu Asp Phe Asp Gly Val Tyr Met Asn Ser Thr Thr
            100                 105                 110

Tyr Leu Asn Gly Glu Val Leu Gly Thr Tyr Pro Phe Gly Tyr Asn Ala
        115                 120                 125

Phe Ser Tyr Asp Ile Ser Asp Lys Leu Tyr Lys Asp Gly Arg Ala Asn
    130                 135                 140

Val Leu Val Val Lys Val Asn Thr Asn Gln Pro Ser Gly Arg Trp Tyr
145                 150                 155                 160

Ser Gly Ser Ser Ile Tyr Arg Asn Val Tyr Leu Thr Val Thr Asp Pro
                165                 170                 175

Ile His Val Ala Arg Tyr Gly Thr Phe Val Thr Thr Pro Asn Leu Glu
            180                 185                 190

Lys Ser Ile Lys Glu Asp Arg Asp Ala Val Asn Ile Lys Thr Lys Ile
        195                 200                 205

Ser Asn Ala Glu Ala Lys Gln Val Lys Ile Ala Ile Lys Ser Thr Ile
    210                 215                 220

Tyr Asp Gly Ala Gly Asn Thr Val Gln Thr Val Glu Thr Glu Glu Lys
225                 230                 235                 240

Thr Ala Ala Ala Gly Thr Val Thr Pro Phe Glu Gln Asn Thr Val Ile
                245                 250                 255

Lys Gln Pro Lys Leu Trp Ser Ile Asp Lys Pro Tyr Arg Tyr Asn Leu
            260                 265                 270

Val Thr Glu Val Ile Val Gly Gly Gln Thr Val Asp Thr Tyr Glu Thr
        275                 280                 285

Lys Phe Gly Val Arg Tyr Phe Lys Phe Asp Glu Asn Glu Gly Tyr Ser
    290                 295                 300

Leu Asn Gly Glu Phe Met Lys Leu His Gly Val Ser Met His His Asp
305                 310                 315                 320
```

-continued

Leu Ala Gly Gly Ala Ala Leu Thr Asn Ala Arg Gly Val Glu Arg Gln
             325                 330                 335

Met Gln Ile Met Lys Asp Val Gly Val Asn Ala Ile Arg Val Thr His
         340                 345                 350

Asn Pro Ala Ser Pro Glu Leu Gly Leu Glu Phe Ala Ala Asn Lys Leu
     355                 360                 365

Leu Ile Ile Glu Glu Ala Phe Asp Ser Trp Ala Gln Ser Lys Lys Pro
 370                 375                 380

Tyr Asp Tyr Gly Arg Phe Phe Asn Ala Trp Ala Glu His Asp Ile Lys
385                 390                 395                 400

Glu Met Val Asp Arg Gly Lys Asn Glu Pro Ala Ile Ile Met Trp Ser
             405                 410                 415

Ile Gly Asn Glu Ile Tyr Asp Thr Thr Asn Ala Ala Gly Val Glu Thr
         420                 425                 430

Ala Arg Asn Leu Val Gly Trp Val Lys Glu Ile Asp Thr Thr Pro Arg
     435                 440                 445

Ala Thr Ile Gly Glu Asp Lys Thr Arg Gly Asp Asn Val Thr Pro Ile
 450                 455                 460

Asn Ser Tyr Ile Lys Glu Ile Phe Asn Ile Val Asp Val Val Gly Leu
465                 470                 475                 480

Asn Tyr Ser Glu Asn Asn Tyr Asp Gly Tyr His Lys Gln Asn Pro Ser
             485                 490                 495

Trp Lys Leu Tyr Gly Ser Glu Thr Ser Ser Ala Thr Arg Ser Arg Gly
         500                 505                 510

Val Tyr Thr His Pro Tyr Gln Tyr Asn His Asp Thr Lys Tyr Ala Asp
     515                 520                 525

Leu Gln Gln Ser Ser Tyr Asp Asn Asp Tyr Val Gly Trp Gly Arg Thr
 530                 535                 540

Ala Gln Asp Ala Trp Lys Tyr Asp Arg Asp Leu Lys His Ile Ala Gly
545                 550                 555                 560

Gln Phe Ile Trp Thr Gly Phe Asp Tyr Ile Gly Glu Pro Thr Pro Tyr
             565                 570                 575

Tyr Asn Ser Tyr Pro Ala Lys Ser Ser Tyr Phe Gly Ala Val Asp Thr
         580                 585                 590

Ala Gly Phe Pro Lys Asp Ile Phe Tyr Tyr Gln Ser Gln Trp Lys
     595                 600                 605

Lys Glu Pro Met Val His Leu Leu Pro His Trp Asn Trp Lys Glu Gly
 610                 615                 620

Glu Lys Val Arg Val Leu Ala Tyr Thr Asn Ala Ser Lys Val Glu Leu
625                 630                 635                 640

Val Leu Asn Gly Glu Ser Leu Gly Asn Glu Lys Tyr Asp Asn Lys Gln
             645                 650                 655

Thr Ser Trp Gly Ala Pro Tyr Lys Glu Thr Lys Asp Gly Lys Thr Tyr
         660                 665                 670

Leu Glu Trp Ala Val Pro Phe Lys Pro Gly Lys Leu Glu Ala Val Ala
     675                 680                 685

Lys Asp Glu Asn Gly Lys Val Ile Ala Arg Asp Gln Val Thr Ala
 690                 695                 700

Gly Glu Pro Ala Ser Val Arg Leu Thr Ala Arg Lys Val Val Lys
705                 710                 715                 720

Ala Asp Gly Thr Asp Leu Ser Phe Ile Thr Ala Asp Ile Val Asp Ser
             725                 730                 735

Lys Gly Ile Val Val Pro Asp Ala Asp His Leu Ile Thr Phe Asn Val

```
                740                 745                 750
Thr Gly Gln Gly Glu Leu Ala Gly Val Asp Asn Gly Asn Ala Ser Ser
            755                 760                 765

Val Glu Arg Tyr Lys Asp Asn Lys Arg Lys Ala Phe Ser Gly Lys Ala
            770                 775                 780

Leu Ala Ile Val Gln Ser Ser Lys Leu Ser Gly Lys Ile Thr Val His
785                 790                 795                 800

Ala Ser Val Ala Gly Leu Ser Ser Asp Ser Thr Ser Val Phe Thr Val
            805                 810                 815

Thr Pro Ala Asp His Asp Lys Lys Ile Val Ala Gly Ile Asp Asp Val
            820                 825                 830

Asn Leu Thr Val Asp Val Asn Glu Ala Pro Lys Leu Pro Ser Glu Ile
            835                 840                 845

Lys Val Tyr Tyr Ser Asp Glu Ser Ala Ala Ala Lys Asn Val Thr Trp
            850                 855                 860

Asp Glu Val Asp Pro Lys Gln Tyr Ser Thr Val Gly Glu Phe Thr Val
865                 870                 875                 880

Glu Gly Ser Val Glu Gly Thr Ser Leu Lys Ala Lys Ala Phe Val Ile
            885                 890                 895

Val Lys Gly Ile Val Ala Val Lys Pro Tyr Ser Thr Ala Thr Lys Val
            900                 905                 910

Gly Val Gln Pro Val Leu Pro Glu Lys Ala Thr Leu Leu Tyr Ser Asp
            915                 920                 925

Gly Thr Thr Lys Gly Ala Thr Val Thr Trp Asp Glu Leu Pro Glu Asp
            930                 935                 940

Lys Leu Ala Lys Glu Gly Arg Phe Thr Val Glu Gly Ser Val Glu Gly
945                 950                 955                 960

Thr Asp Leu Lys Ala Asn Val Tyr Val Arg Val Thr Asn Glu Val Lys
            965                 970                 975

Ser Val Asn Ile Met Leu Gln Glu Gln Gly Ser Ala Tyr Pro Lys Leu
            980                 985                 990

Glu Ala Thr Phe Thr Asn Pro Ala Asp Asn Leu Gln His Leu Asn Asp
            995                 1000                1005

Gly Ile Lys Ser Tyr Thr Asn Asn Gln Val Asn Arg Trp Thr Asn
        1010                1015                1020

Trp Thr Arg Thr Pro Arg Asp Ala Gly Asp Ser Ile Thr Val Asn
        1025                1030                1035

Phe Gly Lys Lys His Val Ile Asn Asn Leu Asp Leu Phe Val Phe
        1040                1045                1050

Thr Asp Ser Gly Thr Val Val Pro Glu Lys Ala Glu Val Gln Tyr
        1055                1060                1065

Trp Asp Gly Thr Ala Trp Lys Asp Val Glu Asn Leu Thr Gln Pro
        1070                1075                1080

Ser Pro Tyr Val Val Glu Lys Asn Glu Leu Thr Phe Asp Ala Val
        1085                1090                1095

Ala Thr Glu Lys Leu Lys Phe His Leu Thr Pro Ser Val Lys Gly
        1100                1105                1110

Lys Phe Leu Ala Leu Thr Glu Ala Glu Val Tyr Ala Asp Gln Ile
        1115                1120                1125

Val Asp Gly Glu Thr Ala Lys Leu Gln Ser Ile Thr Val Asn Gly
        1130                1135                1140

Lys Ala Leu Glu Gly Phe Asp His Ala Lys Lys Asn Tyr Glu Leu
        1145                1150                1155
```

| Val | Leu | Pro | Tyr | Gly | Ser | Glu | Leu | Pro | Lys | Ile | Glu | Ala | Ala | Ala |
|---|---|---|---|---|---|---|---|---|---|---|---|---|---|---|
| | 1160 | | | | 1165 | | | | 1170 | | | | | |

| Ala | Asp | Asn | Ala | Thr | Val | Thr | Ile | Leu | Pro | Ala | Phe | Ser | Tyr | Pro |
|---|---|---|---|---|---|---|---|---|---|---|---|---|---|---|
| 1175 | | | | | 1180 | | | | | 1185 | | | | |

| Gly | Thr | Ala | Lys | Leu | Phe | Val | Thr | Ser | Glu | Asp | Gly | Lys | Val | Thr |
|---|---|---|---|---|---|---|---|---|---|---|---|---|---|---|
| 1190 | | | | | 1195 | | | | | 1200 | | | | |

| Thr | Glu | Tyr | Ser | Ile | Gly | Val | Ser | Thr | Glu | Glu | Pro | Lys | Leu | Val |
|---|---|---|---|---|---|---|---|---|---|---|---|---|---|---|
| 1205 | | | | | 1210 | | | | | 1215 | | | | |

| Ser | Ala | Glu | Leu |
|---|---|---|---|
| 1220 | | | |

<210> SEQ ID NO 17
<211> LENGTH: 2463
<212> TYPE: DNA
<213> ORGANISM: Artificial Sequence
<220> FEATURE:
<223> OTHER INFORMATION: The sequence is synthesized

<400> SEQUENCE: 17

| | | |
|---|---|---|
| atgaaaagca cgacgagcgc cgccggcaaa agcgtcagct ataacgacgg cgaacgccgc | 60 |
| gtcaactttg aaaactggcg cttcagcgc gaaacgaacg gcagcatcgc cggcgcccag | 120 |
| aacccaggct tgacgacag cagctggcgc aaactgaacc tgccgcatga atggagcatc | 180 |
| gacctggact ttaacaaaaa cagcctggcc acgcatgaag cggctatct ggacggcggc | 240 |
| atcggctgga accgcaaaac gtttacgatc ccggaaagca tgaaaggcaa cgctttagc | 300 |
| ctggactttg acgcgtcta tatgaacagc acgacgtatc tgaacggcga agtcctgggc | 360 |
| acgtatccgt ttggctataa cgcctttagc tatgacatca gcgacaaact gtataaagac | 420 |
| ggccgcgcca acgtcctggt cgtcaaagtc aacacgaacc agccgagcgg ccgctggtat | 480 |
| agcggcagca gcatctatcg caacgtctat ctgacggtca cggacccgat ccatgtcgcc | 540 |
| cgctatggca cgtttgtcac gacgccgaac ctggaaaaaa gcatcaaaga agaccgcgac | 600 |
| gccgtcaaca tcaaaacgaa atcagcaac gccgaagcca acaggtcaa atcgccatc | 660 |
| aaaagcacga tctatgacgg cgccggcaac acggtccaga cggtcgaaac ggaagaaaaa | 720 |
| acggccgccg ccggcacggt cacgccgttt gaacagaaca cggtcatcaa acagccgaaa | 780 |
| ctgtggagca tcgacaaacc gtatcgctat aacctggtca cggaagtcat cgtcggcggc | 840 |
| cagacggtcg acacgtatga acgaaatt ggcgtccgct atttaaatt tgacgaaaac | 900 |
| gaaggctata gcctgaacgg cgaattatg aaactgcatg gcgtcagcat gcatcatgac | 960 |
| ctggccggcg gcgccgccct gacgaacgcc cgcggcgtcg aacgccagat gcagatcatg | 1020 |
| aaagacgtcg gcgtcaacgc catccgcgtc acgcataacc cggccagccc ggaactgggc | 1080 |
| ctggaatttg ccgccaacaa actgctgatc atcgaagaag cctttgacag ctgggcccag | 1140 |
| agcaaaaaac cgtatgacta tggccgcttt tttaacgcct gggccgaaca tgacatcaaa | 1200 |
| gaaatggtcg accgcggcaa aaacgaaccg gccatcatca tgtggagcat cggcaacgaa | 1260 |
| atctatgaca cgacgaacgc ccgccggcgtc gaaacggccc gcaacctggt cggctgggtc | 1320 |
| aaagaaatcg acacgacgcc gcgcgccacg atcggcgaag acaaaaacgcg cggcgacaac | 1380 |
| gtcacgccga tcaacagcta tatcaaagaa atctttaaca tcgtcgacgt cgtcggcctg | 1440 |
| aactatagcg aaaacaacta tgacggctat cataaacaga cccgagctg gaaactgtat | 1500 |
| ggcagcgaaa cgagcagcgc cacgcgcagc cgcggcgtct atacgcatcc gtatcagtat | 1560 |
| aaccatgaca cgaaatatgc cgacctgcag cagagcagct atgacaacga ctatgtcggc | 1620 |

```
tggggccgca cggcccagga cgcctggaaa tatgaccgcg acctgaaaca tatcgccggc  1680
cagtttatct ggacgggctt tgactatatc ggcgaaccga cgccgtatta taacagctat  1740
ccggccaaaa gcagctattt tggcgccgtc gacacggccg gctttccgaa agacatcttt  1800
tattattatc agagccagtg gaaaaaagaa ccgatggtcc atctgctgcc gcattggaac  1860 tggaagaag gcgaaaaagt ccgcgtcctg gcctatacga acgccagcaa agtcgaactg  1920
gtcctgaacg gcgaaagcct gggcaacgaa aaatatgaca caaacagac gagctggggc  1980 gccccgtata agaaacgaa agacggcaaa acgtatctgg aatgggccgt cccgtttaaa  2040
ccgggcaaac tggaagccgt cgccaaagac gaaaacggca agtcatcgc ccgcgaccag  2100 gtcgtcacgg ccggcgaacc ggccagcgtc cgcctgacgg ccgaccgcaa agtcgtcaaa  2160
gccgacggca cggacctgag ctttatcacg gccgacatcg tcgacagcaa aggcatcgtc  2220
gtcccggacg ccgaccatct gatcacgttt aacgtcacgg gccagggcga actggccggc  2280
gtcgacaacg gcaacgccag cagcgtcgaa cgctataaag acaacaaacg caaagccttt  2340
agcggcaaag ccctggccat cgtccagagc agcaaactga gcggcaaaat cacggtccat  2400
gccagcgtcg ccggcctgag cagcgacagc acgagcgtct ttacggtcac gccggccgac  2460
taa                                                                2463
```

<210> SEQ ID NO 18
<211> LENGTH: 820
<212> TYPE: PRT
<213> ORGANISM: Artificial Sequence
<220> FEATURE:
<223> OTHER INFORMATION: The sequence is synthesized

<400> SEQUENCE: 18

```
Met Lys Ser Thr Thr Ser Ala Ala Gly Lys Ser Val Ser Tyr Asn Asp
1               5                   10                  15

Gly Glu Arg Arg Val Asn Phe Glu Asn Trp Arg Phe Gln Arg Glu Thr
            20                  25                  30

Asn Gly Ser Ile Ala Gly Ala Gln Asn Pro Gly Phe Asp Asp Ser Ser
        35                  40                  45

Trp Arg Lys Leu Asn Leu Pro His Glu Trp Ser Ile Asp Leu Asp Phe
    50                  55                  60

Asn Lys Asn Ser Leu Ala Thr His Glu Gly Gly Tyr Leu Asp Gly Gly
65                  70                  75                  80

Ile Gly Trp Asn Arg Lys Thr Phe Thr Ile Pro Glu Ser Met Lys Gly
                85                  90                  95

Lys Arg Phe Ser Leu Asp Phe Asp Gly Val Tyr Met Asn Ser Thr Thr
            100                 105                 110

Tyr Leu Asn Gly Glu Val Leu Gly Thr Tyr Pro Phe Gly Tyr Asn Ala
        115                 120                 125

Phe Ser Tyr Asp Ile Ser Asp Lys Leu Tyr Lys Asp Gly Arg Ala Asn
    130                 135                 140

Val Leu Val Val Lys Val Asn Thr Asn Gln Pro Ser Gly Arg Trp Tyr
145                 150                 155                 160

Ser Gly Ser Ser Ile Tyr Arg Asn Val Tyr Leu Thr Val Thr Asp Pro
                165                 170                 175

Ile His Val Ala Arg Tyr Gly Thr Phe Val Thr Thr Pro Asn Leu Glu
            180                 185                 190

Lys Ser Ile Lys Glu Asp Arg Asp Ala Val Asn Ile Lys Thr Lys Ile
        195                 200                 205
```

```
Ser Asn Ala Glu Ala Lys Gln Val Lys Ile Ala Ile Lys Ser Thr Ile
    210                 215                 220
Tyr Asp Gly Ala Gly Asn Thr Val Gln Thr Val Glu Thr Glu Glu Lys
225                 230                 235                 240
Thr Ala Ala Ala Gly Thr Val Thr Pro Phe Glu Gln Asn Thr Val Ile
                245                 250                 255
Lys Gln Pro Lys Leu Trp Ser Ile Asp Lys Pro Tyr Arg Tyr Asn Leu
                260                 265                 270
Val Thr Glu Val Ile Val Gly Gly Gln Thr Val Asp Thr Tyr Glu Thr
            275                 280                 285
Lys Phe Gly Val Arg Tyr Phe Lys Phe Asp Glu Asn Glu Gly Tyr Ser
    290                 295                 300
Leu Asn Gly Glu Phe Met Lys Leu His Gly Val Ser Met His His Asp
305                 310                 315                 320
Leu Ala Gly Gly Ala Ala Leu Thr Asn Ala Arg Gly Val Glu Arg Gln
                325                 330                 335
Met Gln Ile Met Lys Asp Val Gly Val Asn Ala Ile Arg Val Thr His
                340                 345                 350
Asn Pro Ala Ser Pro Glu Leu Gly Leu Glu Phe Ala Ala Asn Lys Leu
            355                 360                 365
Leu Ile Ile Glu Glu Ala Phe Asp Ser Trp Ala Gln Ser Lys Lys Pro
370                 375                 380
Tyr Asp Tyr Gly Arg Phe Phe Asn Ala Trp Ala Glu His Asp Ile Lys
385                 390                 395                 400
Glu Met Val Asp Arg Gly Lys Asn Glu Pro Ala Ile Ile Met Trp Ser
                405                 410                 415
Ile Gly Asn Glu Ile Tyr Asp Thr Thr Asn Ala Ala Gly Val Glu Thr
            420                 425                 430
Ala Arg Asn Leu Val Gly Trp Val Lys Glu Ile Asp Thr Thr Pro Arg
    435                 440                 445
Ala Thr Ile Gly Glu Asp Lys Thr Arg Gly Asp Asn Val Thr Pro Ile
450                 455                 460
Asn Ser Tyr Ile Lys Glu Ile Phe Asn Ile Val Asp Val Val Gly Leu
465                 470                 475                 480
Asn Tyr Ser Glu Asn Asn Tyr Asp Gly Tyr His Lys Gln Asn Pro Ser
                485                 490                 495
Trp Lys Leu Tyr Gly Ser Glu Thr Ser Ser Ala Thr Arg Ser Arg Gly
            500                 505                 510
Val Tyr Thr His Pro Tyr Gln Tyr Asn His Asp Thr Lys Tyr Ala Asp
    515                 520                 525
Leu Gln Gln Ser Ser Tyr Asp Asn Asp Tyr Val Gly Trp Gly Arg Thr
530                 535                 540
Ala Gln Asp Ala Trp Lys Tyr Asp Arg Asp Leu Lys His Ile Ala Gly
545                 550                 555                 560
Gln Phe Ile Trp Thr Gly Phe Asp Tyr Ile Gly Glu Pro Thr Pro Tyr
                565                 570                 575
Tyr Asn Ser Tyr Pro Ala Lys Ser Ser Tyr Phe Gly Ala Val Asp Thr
            580                 585                 590
Ala Gly Phe Pro Lys Asp Ile Phe Tyr Tyr Gln Ser Gln Trp Lys
    595                 600                 605
Lys Glu Pro Met Val His Leu Leu Pro His Trp Asn Trp Lys Glu Gly
    610                 615                 620
```

```
Glu Lys Val Arg Val Leu Ala Tyr Thr Asn Ala Ser Lys Val Glu Leu
625                 630                 635                 640

Val Leu Asn Gly Glu Ser Leu Gly Asn Glu Lys Tyr Asp Asn Lys Gln
            645                 650                 655

Thr Ser Trp Gly Ala Pro Tyr Lys Glu Thr Lys Asp Gly Lys Thr Tyr
            660                 665                 670

Leu Glu Trp Ala Val Pro Phe Lys Pro Gly Lys Leu Glu Ala Val Ala
        675                 680                 685

Lys Asp Glu Asn Gly Lys Val Ile Ala Arg Asp Gln Val Val Thr Ala
    690                 695                 700

Gly Glu Pro Ala Ser Val Arg Leu Thr Ala Asp Arg Lys Val Val Lys
705                 710                 715                 720

Ala Asp Gly Thr Asp Leu Ser Phe Ile Thr Ala Asp Ile Val Asp Ser
            725                 730                 735

Lys Gly Ile Val Val Pro Asp Ala Asp His Leu Ile Thr Phe Asn Val
            740                 745                 750

Thr Gly Gln Gly Glu Leu Ala Gly Val Asp Asn Gly Asn Ala Ser Ser
            755                 760                 765

Val Glu Arg Tyr Lys Asp Asn Lys Arg Lys Ala Phe Ser Gly Lys Ala
770                 775                 780

Leu Ala Ile Val Gln Ser Ser Lys Leu Ser Gly Lys Ile Thr Val His
785                 790                 795                 800

Ala Ser Val Ala Gly Leu Ser Ser Asp Ser Thr Ser Val Phe Thr Val
            805                 810                 815

Thr Pro Ala Asp
            820

<210> SEQ ID NO 19
<211> LENGTH: 628
<212> TYPE: DNA
<213> ORGANISM: Bacillus thuringiensis

<400> SEQUENCE: 19
gaaacgtaag atgaaacctt agataaaagt gctttttttg ttgcaattga agaattatta      60
atgttaagct taattaaaga taatatcttt gaattgtaac gccccctcaaa agtaagaact   120 acaaaaaaag aatacgttat atagaaatat gtttgaacct tcttcagatt acaaatatat    180
tcggacggac tctacctcaa atgcttatct aactatagaa tgacatacaa gcacaacctt   240
gaaaatttga aaatataact accaatgaac ttgttcatgt gaattatcgc tgtatttaat   300
tttctcaatt caatatataa tatgccaata cattgttaca agtagaaatt aagacaccct   360
tgatagcctt actataccta acatgatgta gtattaaatg aatatgtaaa tatatttatg   420
ataagaagcg acttatttat aatcattaca tattttcta ttggaatgat taagattcca    480
atagaatagt gtataaatta tttatcttga aaggagggat gcctaaaaac gaagaacatt   540
aaaaacatat atttgcaccg tctaatggat ttatgaaaaa tcattttatc agtttgaaaa   600
ttatgtatta tgataagaaa gggaggaa                                        628

<210> SEQ ID NO 20
<211> LENGTH: 180
<212> TYPE: DNA
<213> ORGANISM: Bacillus licheniformis

<400> SEQUENCE: 20 ttttttata ggaacattga tttgtattca ctctgccaag ttgttttgat agagtgattg      60
```

```
tgataattt  aaatgtaagc  gttaacaaaa  ttctccagtc  ttcacatcgg  tttgaaagga      120
ggaagcggaa  gaatgaagta  agagggattt  tgactccga   agtaagtctt  caaaaaatca    180
```

<210> SEQ ID NO 21
<211> LENGTH: 426
<212> TYPE: DNA
<213> ORGANISM: Bacillus subtilis

<400> SEQUENCE: 21

```
tgtcgacgtg  catgcaggcc  ggggcatatg  ggaaacagcg  cggacggagc  ggaatttcca    60
atttcatgcc  gcagccgcct  gcgctgttct  catttgcggc  ttccttgtag  agctcagcat    120
tattgagtgg  atgattatat  tccttttgat  aggtggtatg  ttttcgcttg  aacttttaaa    180
tacagccatt  gaacatacgg  ttgatttaat  aactgacaaa  catcaccctc  ttgctaaagc    240
ggccaaggac  gctgccgccg  gggctgtttg  cgttttacc   gtgatttcgt  gtatcattgg    300
tttacttatt  tttttgccaa  agctgtaatg  gctgaaaatt  cttacattta  ttttacattt    360
ttagaaatgg  gcgtgaaaaa  aagcgcgcga  ttatgtaaaa  tataaagtga  tagcggtacc    420
attata                                                                   426
```

<210> SEQ ID NO 22
<211> LENGTH: 87
<212> TYPE: DNA
<213> ORGANISM: Bacillus licheniformis

<400> SEQUENCE: 22

```
atgaaacaac  aaaaacggct  ttacgcccga  ttgctgccgc  tgttatttgc  gctcatcttc    60
ttgctgcctc  attctgcagc  agcggcg                                          87
```

<210> SEQ ID NO 23
<211> LENGTH: 87
<212> TYPE: DNA
<213> ORGANISM: Bacillus licheniformis

<400> SEQUENCE: 23

```
atgatgagga  aaaagagttt  ttggcttggg  atgctgacgg  ccttaatgct  cgtgttcacg    60
atggccttca  gcgattccgc  gtctgct                                          87
```

<210> SEQ ID NO 24
<211> LENGTH: 93
<212> TYPE: DNA
<213> ORGANISM: Bacillus amyloliquefaciens

<400> SEQUENCE: 24

```
atgattcaaa  aacgaaagcg  gacagtttcg  ttcagacttg  tgcttatgtg  cacgctgtta    60
tttgtcagtt  tgccgattac  aaaaacatca  gcc                                  93
```

<210> SEQ ID NO 25
<211> LENGTH: 99
<212> TYPE: DNA
<213> ORGANISM: Bacillus subtilis

<400> SEQUENCE: 25

```
atgtttgcaa  aacgattcaa  aacctctta   ctgccgttat  tcgctggatt  tttattgctg    60
tttcatttgg  ttctggcagg  accggcggct  gcgagtgct                            99
```

<210> SEQ ID NO 26
<211> LENGTH: 81

-continued

```
<212> TYPE: DNA
<213> ORGANISM: Bacillus licheniformis

<400> SEQUENCE: 26
gtgggtttag gtaagaaatt gtctgttgct gtcgctgctt cgtttatgag tttatcaatc    60
agcctgccag gtgttcaggc t                                              81

<210> SEQ ID NO 27
<211> LENGTH: 97
<212> TYPE: DNA
<213> ORGANISM: Bacillus licheniformis

<400> SEQUENCE: 27
atgttgatca acaaaagcaa aaagttttc gttttttctt tcattttgt tatgatgctg     60 agcctctcat ttgtgaatgg ggaagttgca aaagccg                             97

<210> SEQ ID NO 28
<211> LENGTH: 33
<212> TYPE: DNA
<213> ORGANISM: Artificial Sequence
<220> FEATURE:
<223> OTHER INFORMATION: The sequence is synthesized

<400> SEQUENCE: 28
ggatcccggg actagttcta gagcggccgc cac                                 33

<210> SEQ ID NO 29
<211> LENGTH: 25
<212> TYPE: DNA
<213> ORGANISM: Artificial Sequence
<220> FEATURE:
<223> OTHER INFORMATION: The sequence is synthesized

<400> SEQUENCE: 29
gttaagggat gcataaactg catcc                                          25

<210> SEQ ID NO 30
<211> LENGTH: 26
<212> TYPE: DNA
<213> ORGANISM: Artificial Sequence
<220> FEATURE:
<223> OTHER INFORMATION: The sequence is synthesized

<400> SEQUENCE: 30
gctctagatc aaggcaccga acgatt                                         26

<210> SEQ ID NO 31
<211> LENGTH: 40
<212> TYPE: DNA
<213> ORGANISM: Artificial Sequence
<220> FEATURE:
<223> OTHER INFORMATION: The sequence is synthesized

<400> SEQUENCE: 31
ctttcgtctt ctccatttac gcgctgcaca gtttgtattt                          40

<210> SEQ ID NO 32
<211> LENGTH: 42
<212> TYPE: DNA
<213> ORGANISM: Artificial Sequence
<220> FEATURE:
<223> OTHER INFORMATION: The sequence is synthesized

<400> SEQUENCE: 32
```
aaatacaaac tgtgcagcgc gtaaatggag aagacgcgaa ag        42

<210> SEQ ID NO 33
<211> LENGTH: 26
<212> TYPE: DNA
<213> ORGANISM: Artificial Sequence
<220> FEATURE:
<223> OTHER INFORMATION: The sequence is synthesized

<400> SEQUENCE: 33
cgggatccta tgcctggtgc ctgacg        26

<210> SEQ ID NO 34
<211> LENGTH: 26
<212> TYPE: DNA
<213> ORGANISM: Artificial Sequence
<220> FEATURE:
<223> OTHER INFORMATION: The sequence is synthesized

<400> SEQUENCE: 34
gctctagatc aaggcaccga acgatt        26

<210> SEQ ID NO 35
<211> LENGTH: 26
<212> TYPE: DNA
<213> ORGANISM: Artificial Sequence
<220> FEATURE:
<223> OTHER INFORMATION: The sequence is synthesized

<400> SEQUENCE: 35
cgggatccta tgcctggtgc ctgacg        26

<210> SEQ ID NO 36
<211> LENGTH: 24
<212> TYPE: DNA
<213> ORGANISM: Artificial Sequence
<220> FEATURE:
<223> OTHER INFORMATION: The sequence is synthesized

<400> SEQUENCE: 36
ctgcagatta ttatgccgct atcc        24

<210> SEQ ID NO 37
<211> LENGTH: 50
<212> TYPE: DNA
<213> ORGANISM: Artificial Sequence
<220> FEATURE:
<223> OTHER INFORMATION: The sequence is synthesized

<400> SEQUENCE: 37
tcatcctgtc tgacttgaac ggcccgggaa atgtattcgt atgggcaagc        50

<210> SEQ ID NO 38
<211> LENGTH: 50
<212> TYPE: DNA
<213> ORGANISM: Artificial Sequence
<220> FEATURE:
<223> OTHER INFORMATION: The sequence is synthesized

<400> SEQUENCE: 38
gcttgcccat acgaatacat ttcccgggcc gttcaagtca gacaggatga        50

<210> SEQ ID NO 39
<211> LENGTH: 30
<212> TYPE: DNA
<213> ORGANISM: Artificial Sequence

```
<220> FEATURE:
<223> OTHER INFORMATION: The sequence is synthesized

<400> SEQUENCE: 39
acgtctagat cttccaaagc gatgatgctc                                              30

<210> SEQ ID NO 40
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 40
cagatgcttg gaatgatgaa cag                                                     23

<210> SEQ ID NO 41
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 41
gacataattg acgcctgctt c                                                       21

<210> SEQ ID NO 42
<211> LENGTH: 29
<212> TYPE: DNA
<213> ORGANISM: Artificial Sequence
<220> FEATURE:
<223> OTHER INFORMATION: The sequence is synthesized

<400> SEQUENCE: 42
atttctagaa gttcccgtgt aaagagttg                                               29

<210> SEQ ID NO 43
<211> LENGTH: 44
<212> TYPE: DNA
<213> ORGANISM: Artificial Sequence
<220> FEATURE:
<223> OTHER INFORMATION: The sequence is synthesized

<400> SEQUENCE: 43
gcgttacaat ggatgaagcc cgggtggttt gtatccgctg aatc                              44

<210> SEQ ID NO 44
<211> LENGTH: 44
<212> TYPE: DNA
<213> ORGANISM: Artificial Sequence
<220> FEATURE:
<223> OTHER INFORMATION: The sequence is synthesized

<400> SEQUENCE: 44
gattcagcgg atacaaacca cccgggcttc atccattgta acgc                              44

<210> SEQ ID NO 45
<211> LENGTH: 28
<212> TYPE: DNA
<213> ORGANISM: Artificial Sequence
<220> FEATURE:
<223> OTHER INFORMATION: The sequence is synthesized

<400> SEQUENCE: 45
agaggatcca gattgatagc ctttgccc                                                28
```

<210> SEQ ID NO 46
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 46
cacccacttc ccattatgag          20

<210> SEQ ID NO 47
<211> LENGTH: 18
<212> TYPE: DNA
<213> ORGANISM: Artificial Sequence
<220> FEATURE:
<223> OTHER INFORMATION: The sequence is synthesized

<400> SEQUENCE: 47
aaagcggtaa acagccag          18

<210> SEQ ID NO 48
<211> LENGTH: 31
<212> TYPE: DNA
<213> ORGANISM: Artificial Sequence
<220> FEATURE:
<223> OTHER INFORMATION: The sequence is synthesized

<400> SEQUENCE: 48
atttctagac ggctttatcc tttgctgtta c          31

<210> SEQ ID NO 49
<211> LENGTH: 46
<212> TYPE: DNA
<213> ORGANISM: Artificial Sequence
<220> FEATURE:
<223> OTHER INFORMATION: The sequence is synthesized

<400> SEQUENCE: 49
gaataacgaa accacaattg acccgggcgg aaacctcgct cagaac          46

<210> SEQ ID NO 50
<211> LENGTH: 45
<212> TYPE: DNA
<213> ORGANISM: Artificial Sequence
<220> FEATURE:
<223> OTHER INFORMATION: The sequence is synthesized

<400> SEQUENCE: 50
gttctgagcg aggtttccgc ccgggtcaat gtggtttcgt tattc          45

<210> SEQ ID NO 51
<211> LENGTH: 29
<212> TYPE: DNA
<213> ORGANISM: Artificial Sequence
<220> FEATURE:
<223> OTHER INFORMATION: The sequence is synthesized

<400> SEQUENCE: 51
agaggatcca gaagagcaaa tcaagcaac          29

<210> SEQ ID NO 52
<211> LENGTH: 18
<212> TYPE: DNA
<213> ORGANISM: Artificial Sequence
<220> FEATURE:
<223> OTHER INFORMATION: The sequence is synthesized

```
<400> SEQUENCE: 52
atcatcggaa tggtttgcg                                                      18

<210> SEQ ID NO 53
<211> LENGTH: 22
<212> TYPE: DNA
<213> ORGANISM: Artificial Sequence
<220> FEATURE:
<223> OTHER INFORMATION: The sequence is synthesized

<400> SEQUENCE: 53
actttatcgg attgcggaga tg                                                  22

<210> SEQ ID NO 54
<211> LENGTH: 27
<212> TYPE: DNA
<213> ORGANISM: Artificial Sequence
<220> FEATURE:
<223> OTHER INFORMATION: The sequence is synthesized

<400> SEQUENCE: 54
gctctagaat aatccgtgtg ttcgccg                                             27

<210> SEQ ID NO 55
<211> LENGTH: 39
<212> TYPE: DNA
<213> ORGANISM: Artificial Sequence
<220> FEATURE:
<223> OTHER INFORMATION: The sequence is synthesized

<400> SEQUENCE: 55
tgatgatgct gactctgccc gggaaaccgt tgagatgga                                39

<210> SEQ ID NO 56
<211> LENGTH: 39
<212> TYPE: DNA
<213> ORGANISM: Artificial Sequence
<220> FEATURE:
<223> OTHER INFORMATION: The sequence is synthesized

<400> SEQUENCE: 56
tccatctcaa cggtttcccg ggcagagtca gcatcatca                                39

<210> SEQ ID NO 57
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 57
ttcccagacc acgagttcct                                                     20

<210> SEQ ID NO 58
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 58
actggtcaaa ggctaaatcg c                                                   21

<210> SEQ ID NO 59
```

```
<211> LENGTH: 19
<212> TYPE: DNA
<213> ORGANISM: Artificial Sequence
<220> FEATURE:
<223> OTHER INFORMATION: The sequence is synthesized

<400> SEQUENCE: 59
atccatccgc aagtcttcg                                                      19

<210> SEQ ID NO 60
<211> LENGTH: 28
<212> TYPE: DNA
<213> ORGANISM: Artificial Sequence
<220> FEATURE:
<223> OTHER INFORMATION: The sequence is synthesized

<400> SEQUENCE: 60
atttctagag attgatttcc gccatctc                                            28

<210> SEQ ID NO 61
<211> LENGTH: 44
<212> TYPE: DNA
<213> ORGANISM: Artificial Sequence
<220> FEATURE:
<223> OTHER INFORMATION: The sequence is synthesized

<400> SEQUENCE: 61
tcccgcactc ttcaatgagc ccgggtcttc cttcttcagg ctcg                          44

<210> SEQ ID NO 62
<211> LENGTH: 44
<212> TYPE: DNA
<213> ORGANISM: Artificial Sequence
<220> FEATURE:
<223> OTHER INFORMATION: The sequence is synthesized

<400> SEQUENCE: 62
cgagcctgaa gaaggaagac ccgggctcat tgaagagtgc ggga                          44

<210> SEQ ID NO 63
<211> LENGTH: 19
<212> TYPE: DNA
<213> ORGANISM: Artificial Sequence
<220> FEATURE:
<223> OTHER INFORMATION: The sequence is synthesized

<400> SEQUENCE: 63
aacgagccaa ataacgacg                                                      19

<210> SEQ ID NO 64
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 64
cgtcaatgaa aagggctgt c                                                    21

<210> SEQ ID NO 65
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 65
```
acggcgaaaa tacggaaaat                                              20

<210> SEQ ID NO 66
<211> LENGTH: 28
<212> TYPE: DNA
<213> ORGANISM: Artificial Sequence
<220> FEATURE:
<223> OTHER INFORMATION: The sequence is synthesized

<400> SEQUENCE: 66
atttctagag ccgcttctca tcacacct                                     28

<210> SEQ ID NO 67
<211> LENGTH: 41
<212> TYPE: DNA
<213> ORGANISM: Artificial Sequence
<220> FEATURE:
<223> OTHER INFORMATION: The sequence is synthesized

<400> SEQUENCE: 67
tatggtgctc tgttcttccg cattcacatg cattctttcc g                      41

<210> SEQ ID NO 68
<211> LENGTH: 41
<212> TYPE: DNA
<213> ORGANISM: Artificial Sequence
<220> FEATURE:
<223> OTHER INFORMATION: The sequence is synthesized

<400> SEQUENCE: 68
cggaaagaat gcatgtgaat gcggaagaac agagcaccat a                      41

<210> SEQ ID NO 69
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 69
cggcgattca tttattctct g                                            21

<210> SEQ ID NO 70
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 70
atgacaatca gcatctattt ggc                                          23

<210> SEQ ID NO 71
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 71
cctcctttct gttcaaccga                                              20

<210> SEQ ID NO 72
<211> LENGTH: 6702
<212> TYPE: DNA

<213> ORGANISM: Artificial Sequence
<220> FEATURE:
<223> OTHER INFORMATION: The sequence is synthesized

<400> SEQUENCE: 72

```
aggatccatt ggtaactgta tctcagcttg aagaagtgaa gaagcagaga ggctattgaa      60
taaatgagta gaaagcgcca tatcggcgct tttcttttgg aagaaaatat agggaaaatg     120
gtacttgtta aaaattcgga atatttatac aatatcatat gtttcacatt gaaaggggag     180
gagaatcatg aaacaacaaa aacggcttta cgcccgattg ctgacgctgt tatttgcgct     240
catcttcttg ctgcctcatt ctgcagcagc ggcggcaaat ctagaattcg agctcccggg     300
taccatggca tgctaattag atagagcaga gaggacggat ttcctgaagg aaatccgttt     360
ttttattttg cccgtcttat aagacaaggg aaaacgcaag cgcaaagaga agcaggtag      420
cttgcagtgg gcttacatgg cgatagctag actgggcggt tttatggaca gcaagcgaac     480
cggaattgcc agctggggcg ccctctggta aggttgggaa gccctgcaaa gtaaactgga     540
tggctttctt gccgccaagg atctgatggc gcagggatc aagatctgat caagagacag      600
gatgaggatc gtttcgcatg attgaacaag atggattgca cgcaggttct ccggccgctt     660
gggtggagag gctattcggc tatgactggg cacaacagac aatcggctgc tctgatgccg     720
ccgtgttccg gctgtcagcg caggggcgcc cggttctttt tgtcaagacc gacctgtccg     780
gtgccctgaa tgaactgcag gacgaggcag cgcggctatc gtggctggcc acgacgggcg     840
ttccttgcgc agctgtgctc gacgttgtca ctgaagcggg aagggactgg ctgctattgg     900
gcgaagtgcc ggggcaggat ctcctgtcat ctcaccttgc tcctgccgag aaagtatcca     960
tcatggctga tgcaatgcgg cggctgcata cgcttgatcc ggctacctgc ccattcgacc    1020
accaagcgaa acatcgcatc gagcgagcac gtactcggat ggaagccggt cttgtcgatc    1080
aggatgatct ggacgaagag catcaggggc tcgcgccagc cgaactgttc gccaggctca    1140
aggcgcgcat gcccgacggc gaggatctcg tcgtgaccca tggcgatgcc tgcttgccga    1200
atatcatggt ggaaaatggc cgcttttctg gattcatcga ctgtggccgg ctgggtgtgg    1260
cggaccgcta tcaggacata gcgttggcta cccgtgatat tgctgaagag cttggcggcg    1320
aatgggctga ccgcttcctc gtgctttacg gtatcgccgc tcccgattcg cagcgcatcg    1380
ccttctatcg ccttcttgac gagttcttct aataagggga tcttgaagtt cctattccga    1440
agttcctatt ctctagaaag tataggaact tcgaagcagc tccagcctac actggtctta    1500
tgacttgggc gcgctggaaa actatttgaa caaaacaaat tttaatcatt cagtgtttga    1560
cgtgccgctt cattatcagt tccatgctgc atcgacacag ggaggcggct atgatatgag    1620
gaaattgctg aacggtacgg tcgttttcaa gcatccgttg aaatcggtta catttgtcga    1680
taaccatgat acacagccgg ggcaatcgct tgagtcgact gtccaaacat ggtttaagcc    1740
gcttgcttac gcttttattc tcacaaggga atctggatac cctcaggttt tctacgggga    1800
tatgtacggg acgaaaggag actcccagcg cgaaattcct gccttgaaac acaaaattga    1860
acagatctca attcctgtta taaaaaaagg atcaattttg aactctctcc caaagttgat    1920
cccttaacga tttagaaatc cctttgagaa tgtttatata cattcaaggt aaccagccaa    1980
ctaatgacaa tgattcctga aaaagtaat aacaaattac tatacagata agttgactga     2040
tcaacttcca taggtaacaa cctttgatca agtaagggta tggataataa accacctaca    2100
attgcaatac ctgttccctc tgataaaaag ctggtaaagt taagcaaact cattccagca    2160
ccagcttcct gctgtttcaa gctacttgaa acaattgttg atataactgt tttggtgaac    2220
```

```
gaaagcccac ctaaaacaaa tacgattata attgtcatga accatgatgt tgtttctaaa    2280
agaaaggaag cagttaaaaa gctaacagaa agaaatgtaa ctccgatgtt taacacgtat    2340
aaaggacctc ttctatcaac aagtatccca ccaatgtagc cgaaaataat gacactcatt    2400
gttccaggga aaataattac acttccgatt tcggcagtac ttagctggtg aacatctttc    2460
atcatataag gaaccataga gacaaaccct gctactgttc caaatataat tcccccacaa    2520
agaactccaa tcataaaagg tatattttc cctaatccgg gatcaacaaa aggatctgtt    2580
actttcctga tatgttttac aaatatcagg aatgacagca cgctaacgat aagaaaagaa    2640
atgctatatg atgttgtaaa caacataaaa aatacaatgc ctacagacat tagtataatt    2700
cctttgatat caaaatgacc ttttatcctt acttctttct ttaataattt cataagaaac    2760
ggaacagtga taattgttat cataggaatg agtagaagat aggaccaatg aatataatgg    2820
gctatcattc caccaatcgc tggaccgact ccttctccca tggctactat cgatccaata    2880
agaccaaatg ctttaccccct attttccttt ggaatatagc gcgcaactac aaccattacg    2940
agtgctggaa atgcagctgc accagcccct tgaataaaac gagccataat aagtaaggaa    3000
aagaaagaat ggccaacaaa cccaattacc gacccgaaac aatttattat aattccaaat    3060
aggagtaacc ttttgatgcc taattgatca gatagctttc catatacagc tgttccaatg    3120
gaaaaggtta acataaaggc tgtgttcacc cagtttgtac tcgcaggtgg tttattaaaa    3180
tcatttgcaa tatcaggtaa tgagacgttc aaaaccattt catttaatac gctaaaaaaa    3240
gataaaatgc aaagccaaat taaaatttgg ttgtgtcgta aattcgattg tgaataggat    3300
gtattcacat ttcaccctcc aataatgagg gcagacgtag tttatagggt taatgatacg    3360
cttccctctt ttaattgaac cctgttacat tcattattca ttacacttca taattaattc    3420
ctcctaaact tgattaaaac attttaccac atataaacta agttttaaat tcagtatttc    3480
atcacttata caacaatatg gcccgtttgt tgaactactc tttaataaaa taatttttcc    3540
gttcccaatt ccacattgca ataatagaaa atccatcttc atcggctttt tcgtcatcat    3600
ctgtatgaat caaatcgcct tcttctgtgt catcaaggtt taatttttta tgtatttctt    3660
ttaacaaacc accataggag attaaccttt tacggtgtaa accttcctcc aaatcagaca    3720
aacgtttcaa attcttttct tcatcatcgg tcataaaatc cgtatccttt acaggatatt    3780
ttgcagtttc gtcaattgcc gattgtatat ccgatttata tttatttttc ggtcgaatca    3840
tttgaacttt tacatttgga tcatagtcta atttcattgc cttttttccaa aattgaatcc    3900 attgtttttg attcacgtag ttttctgtat tcttaaaata agttggttcc acacatacca    3960
atacatgcat gtgctgatta taagaattat ctttattatt tattgtcact tccgttgcac    4020
gcataaaacc aacaagattt ttattaattt ttttatattg catcattcgg cgaaatcctt    4080
gagccatatc tgacaaactc ttatttaatt cttcgccatc ataaacattt ttaactgtta    4140
atgtgagaaa caaccaacga actgttggct tttgtttaat aacttcagca acaacctttt    4200
gtgactgaat gccatgtttc attgctctcc tccagttgca cattggacaa agcctggatt    4260
tacaaaacca cactcgatac aactttcttt cgcctgtttc acgatttgt ttatactcta    4320 atatttcagc acaatctttt actctttcag ccttttttaaa ttcaagaata tgcagaagtt    4380
caaagtaatc aacattagcg atttctttt ctctccatgg tctcactttt ccacttttg    4440 tcttgtccac taaaacccctt gatttttcat ctgaataaat gctactatta ggacacataa    4500
tattaaaaga aaccccccatc tatttagtta tttgtttggt cacttataac tttaacagat    4560
```

```
ggggttttc  tgtgcaacca  attttaaggg  ttttccaata  ctttaaaaca  catacatacc    4620
aacacttcaa  cgcaccttc   agcaactaaa  ataaaaatga  cgttatttct  atatgtatca    4680
agataagaaa  gaacaagttc  aaaaccatca  aaaaaagaca  ccttttcagg  tgcttttttt    4740
attttataaa  ctcattccct  gatctcgact  tcgttctttt  tttacctctc  ggttatgagt    4800
tagttcaaat  tcgttctttt  taggttctaa  atcgtgtttt  tcttggaatt  gtgctgtttt    4860
atcctttacc  ttgtctacaa  acccttaaa   aacgtttta   aaggctttta  agcgtctgta    4920
cgttccttaa  ggaattattc  cttagtgctt  tctaggttaa  tgtcatgata  ataatggttt    4980
cttagacgtc  aggtggcact  tttcggggaa  atgtccgcgg  aaccctatt   tgtttatttt    5040 tctaaataca  ttcaaatatg  tatccgctca  tgagacaata  accctgataa  atgcttcaat    5100
aatattgaaa  aaggaagagt  atgagtattc  aacatttccg  tgtcgccctt  attcccttt     5160 ttgcggcatt  ttgccttcct  gtttttgctc  acccagaaac  gctggtgaaa  gtaaaagatg    5220
ctgaagatca  gttgggtgca  cgagtgggtt  acatcgaact  ggatctcaac  agcggtaaga    5280
tccttgagag  ttttcgcccc  gaagaacgtt  ttccaatgat  gagcactttt  aaagttctgc    5340
tatgtggcgc  ggtattatcc  cgtgttgacg  ccgggcaaga  gcaactcggt  cgccgcatac    5400
actattctca  gaatgacttg  gttgagtact  caccagtcac  agaaaagcat  cttacggatg    5460
gcatgacagt  aagagaatta  tgcagtgctg  ccataaccat  gagtgataac  actgcggcca    5520
acttacttct  gacaacgatc  ggaggaccga  aggagctaac  cgcttttttg  cacaacatgg    5580
gggatcatgt  aactcgcctt  gatcgttggg  aaccggagct  gaatgaagcc  ataccaaacg    5640
acgagcgtga  caccacgatg  cctgcagcaa  tggcaacaac  gttgcgcaaa  ctattaactg    5700
gcgaactact  tactctagct  tcccggcaac  aattaataga  ctggatggag  gcggataaag    5760
ttgcaggacc  acttctgcgc  tcggccctc   cggctggctg  gtttattgct  gataaatctg    5820
gagccggtga  gcgtgggtct  cgcggtatca  ttgcagcact  ggggccagat  ggtaagccct    5880
cccgtatcgt  agttatctac  acgacgggga  gtcaggcaac  tatggatgaa  cgaaatagac    5940
agatcgctga  gataggtgcc  tcactgatta  agcattggta  actgtcagac  caagtttact    6000
catatatact  ttagattgat  ttaaaacttc  attttaatt   taaaaggatc  taggtgaaga    6060 tccttttga   taatctcatg  accaaaatcc  cttaacgtga  gttttcgttc  cactgagcgt    6120
cagacccctt  aataagatga  tcttcttgag  atcgttttgg  tctgcgcgta  atctcttgct    6180
ctgaaaacga  aaaaccgcc   ttgcagggag  gttttcgaa   ggttctctga  gctaccaact    6240
ctttgaaccg  aggtaactgg  cttgcaggag  cgcagtcacc  aaaacttgtc  ctttcagttt    6300
agccttaacc  ggcgcatgac  ttcaagacta  actcctctaa  atcaattacc  agtggctgct    6360
gccagtggtg  cttttgcatg  tctttccggg  ttggactcaa  gacgatagtt  accggataag    6420
gcgcagcggt  cggactgaac  gggggggttcg  tgcatacagt  ccagcttgga  gcgaactgcc    6480
tacccggaac  tgagtgtcag  gcgtggaatg  agacaaacgc  ggccataaca  gcggaatgac    6540
accggtaaac  cgaaaggcag  gaacaggaga  gcgcacgagg  agccgccag   ggggaaacgc    6600 ctggtatctt  tatagtcctg  tcgggtttcg  ccaccactga  tttgagcgtc  agatttcgtg    6660
atgcttgtca  ggggcggag   cctatggaaa  aacgctttgc  cc                       6702
```